(12) United States Patent
Nomoto et al.

(10) Patent No.: US 7,524,659 B2
(45) Date of Patent: Apr. 28, 2009

(54) ISOGENIC STRAIN LINE OF BACTERIUM FOR PRODUCING POLYHYDROXYALKANOATE IN WHICH POLYHYDROXYALKANOATE SYNTHASE GENE IS DISRUPTED AND METHOD FOR PRODUCING POLYHYDROXYALKANOATE USING THE SAME

(75) Inventors: Tsuyoshi Nomoto, Tokyo (JP); Tetsuya Yano, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 349 days.

(21) Appl. No.: 11/341,495

(22) Filed: Jan. 30, 2006

(65) Prior Publication Data

US 2006/0172398 A1 Aug. 3, 2006

(30) Foreign Application Priority Data

Jan. 31, 2005 (JP) .............................. 2005-023976

(51) Int. Cl.
*C12P 7/62* (2006.01)
*C12N 9/00* (2006.01)
*C12N 1/20* (2006.01)
*C07H 21/04* (2006.01)

(52) U.S. Cl. ........................ 435/135; 435/183; 435/193; 435/252.3; 435/252.34; 536/23.2

(58) Field of Classification Search ........................ None
See application file for complete search history.

(56) References Cited

U.S. PATENT DOCUMENTS

| | | | | |
|---|---|---|---|---|
| 5,653,675 A | 8/1997 | Kanno et al. | ................. | 588/249 |
| 5,665,597 A | 9/1997 | Imamura et al. | ......... | 435/253.3 |
| 5,670,315 A | 9/1997 | Yamamoto et al. | ............. | 435/6 |
| 5,679,568 A | 10/1997 | Imamura et al. | ......... | 435/262.5 |
| 5,753,466 A | 5/1998 | Yano et al. | ................. | 435/91.1 |
| 5,803,664 A | 9/1998 | Kawabata et al. | ............ | 405/128 |
| 5,807,736 A | 9/1998 | Kozaki et al. | ............. | 435/262.5 |
| 5,854,059 A | 12/1998 | Kozaki et al. | ................ | 435/262 |
| 5,863,789 A | 1/1999 | Komatsu et al. | ............ | 435/262 |
| 5,945,331 A | 8/1999 | Kozaki et al. | ................ | 435/262 |
| 5,962,305 A | 10/1999 | Mihara et al. | ............ | 435/262.5 |
| 6,004,772 A | 12/1999 | Imamura et al. | ............... | 435/34 |
| 6,017,746 A | 1/2000 | Imamura et al. | ............ | 435/252.1 |
| 6,424,418 B2 | 7/2002 | Kawabata et al. | ............ | 356/445 |
| 6,472,191 B1 | 10/2002 | Yano et al. | ................... | 435/189 |
| 6,479,621 B2 | 11/2002 | Honma et al. | ................ | 528/361 |
| 6,586,562 B2 | 7/2003 | Honma et al. | ................ | 528/361 |
| 6,649,381 B1 | 11/2003 | Honma et al. | ................ | 435/135 |
| 6,660,516 B1 | 12/2003 | Imamura et al. | ......... | 435/252.8 |
| 6,686,439 B2 | 2/2004 | Kenmoku et al. | ............ | 528/272 |
| 6,803,444 B2 | 10/2004 | Suzuki et al. | ................ | 528/361 |
| 6,808,854 B2 | 10/2004 | Imamura et al. | ............ | 430/110 |
| 6,828,074 B2 | 12/2004 | Yano et al. | ................ | 430/109.1 |
| 6,853,477 B2 | 2/2005 | Nomoto et al. | ............. | 359/296 |
| 6,855,472 B2 | 2/2005 | Imamura et al. | ......... | 430/109.4 |
| 6,858,367 B2 | 2/2005 | Yano et al. | ................... | 430/109 |
| 6,858,417 B2 | 2/2005 | Yano et al. | ................... | 435/189 |
| 6,861,496 B2 | 3/2005 | Kenmoku et al. | ........... | 528/272 |
| 6,861,550 B2 | 3/2005 | Honma et al. | ................. | 560/53 |
| 6,864,074 B2 | 3/2005 | Yano et al. | ................... | 435/189 |
| 6,867,023 B2 | 3/2005 | Honma et al. | ................ | 435/135 |
| 6,869,782 B2 | 3/2005 | Kenmoku et al. | ........... | 435/130 |
| 6,908,720 B2 | 6/2005 | Kenmoku et al. | ............. | 430/97 |
| 6,916,861 B2 | 7/2005 | Nomoto et al. | ............. | 523/160 |
| 6,951,745 B2 | 10/2005 | Nomoto et al. | ............. | 435/118 |
| 7,153,622 B2 | 12/2006 | Honma et al. | ................ | 430/105 |
| 7,169,598 B2 | 1/2007 | Honma et al. | ............ | 435/253.3 |
| 2003/0104302 A1 | 6/2003 | Honma et al. | ............ | 430/110.2 |
| 2003/0118931 A1 | 6/2003 | Yano et al. | ............. | 430/108.22 |
| 2003/0194443 A1 | 10/2003 | Yano et al. | ................... | 424/497 |
| 2004/0005638 A1 | 1/2004 | Honma et al. | ................. | 435/7.1 |
| 2005/0208635 A1 | 9/2005 | Nomoto et al. | ............. | 435/135 |
| 2006/0172394 A1 | 8/2006 | Kozaki et al. | ................ | 435/117 |
| 2006/0172399 A1 | 8/2006 | Nomoto et al. | ............. | 435/135 |
| 2006/0172400 A1 | 8/2006 | Nomoto et al. | ............. | 435/135 |
| 2006/0275811 A1 | 12/2006 | Hatakeyama et al. | .......... | 435/6 |
| 2007/0054315 A1 | 3/2007 | Imamura et al. | ............. | 435/7.1 |

FOREIGN PATENT DOCUMENTS

| | | |
|---|---|---|
| JP | 2001-8689 | 1/2001 |
| JP | 2003-11312 | 1/2003 |

OTHER PUBLICATIONS

Biodegradable Plastics Research Group, ed., Biodegradable Plastics Handbook, NTS Inc., 1995, pp. 178 to 197.

Hideki Abe, et al., "Biosynthesis from gluconate of a random copolyester consisting of 3-hydroxybutyrate and medium-chain-length 3-hydroxyalkanoates by *Pseudomonas* sp. 61-3", Int. J. Biol. Macromol., vol. 16, No. 3, 1994, pp. 115-119.

(Continued)

*Primary Examiner*—Christian L Fronda
(74) *Attorney, Agent, or Firm*—Fitzpatrick, Cella, Harper & Scinto

(57) ABSTRACT

A host-vector system which is equipped with a substrate supply system enzyme for polyhydroxyalkanoate synthase and which is suitable for evolutionary engineering modification of polyhydroxyalkanoate synthase. An isogenic strain line is produced by disrupting a polyhydroxyalkanoate synthase gene of a bacterium for producing polyhydroxyalkanoate.

2 Claims, 3 Drawing Sheets

OTHER PUBLICATIONS

A. A. Amara, et al., "In vivo evolution of the *Aeromonas punctata* polyhydroxyalkanoate (PHA) synthase: isolation and characterization of modified PHA synthases with enhanced activity", Applied Microbiology and Biotechnology, vol. 59, 2002, pp. 477-482.

John Davison, et al., "Vectors with restriction site banks V. pJRD215, a wide-host-range cosmid vector with multiple cloning sites", Gene, vol. 51, Nos. 2 and 3, 1987, pp. 275-280.

Katharina Fritzsche, et al., "An unusual bacterial polyester with a phenyl pendant group", Makromol. Chem., vol. 191, 1990, pp. 1957-1965.

Richard A. Gross, et al., "Cyanophenoxy-Containing Microbial Polyesters: Structural Analysis, Thermal Properties, Second Harmonic Generation and In-Vivo Biodegradability", Polymer International, vol. 39, No. 3, 1996, pp. 205-213.

Tomoyasu Kichise, et al., "Enhanced Accumulation and Changed Monomer Composition in Polyhydroxyalkanoate (PHA) Copolyester by In Vitro Evolution of *Aeromonas caviae* PHA Synthase", Applied and Environmental Microbiology, vol. 68, No. 5, 2002, pp. 2411-2419.

Ohyoung Kim, et al., "Bioengineering of poly(β-hydroxyalkanoates) for advanced material applications: incorporation of cyano and nitrophenoxy side chain substituents", Canadian Journal of Microbiology, vol. 41 (Suppl. 1), 1995, pp. 32-43.

Y. B. Kim, et al., "Preparation and Characterization of Poly(β-hydroxyalkanoates) Obtained from *Pseudomonas oleovorans* Grown with Mixtures of 5-Phenylvaleric Acid and *n*-Alkanoic Acids", Macromolecules, vol. 24, 1991, pp. 5256-5260.

Michael E. Kovach, et al., "Four new derivatives of the broad-host-range cloning vector pBBR1MCS, carrying different antibiotic-resistance cassettes", Gene, vol. 166, 1995, pp. 175-176.

Bruce A. Ramsay, et al. "Effect of Nitrogen Limitation on Long-Side-Chain Poly-β-Hydroxyalkanoate Synthesis by *Pseudomonas resinovorans*", Applied and Environmental Microbiology, vol. 58, No. 2, Feb. 1992, pp. 744-746.

Christine E. Seidman, et al., "Introduction of Plasmid DNA into Cells", Current Protocols in Molecular Biology, vol. 1, Supplement 37, 1994, pp. 1.8.1-1.8.6.

R. Simon, et al., "A Broad Host Range Mobilization System for in Vivo Genetic Engineering: Transposon Mutagenesis in Gram Negative Bacteria", Bio/technology, vol. 1, No. 9, Nov. 1983, pp. 784-791.

Kazuma Takase, et al., "Enhanced Synthesis of Poly(3-hydroxybutyrate) in Recombinant *Escherichia coli* by Means of Error-Prone PCR Mutagenesis, Saturation Mutagenesis, and In Vitro Recombination of the Type II Polyhydroxyalkanoate Synthase Gene", The Journal of Biochemistry, vol. 133, No. 1, 2003, pp. 139-145.

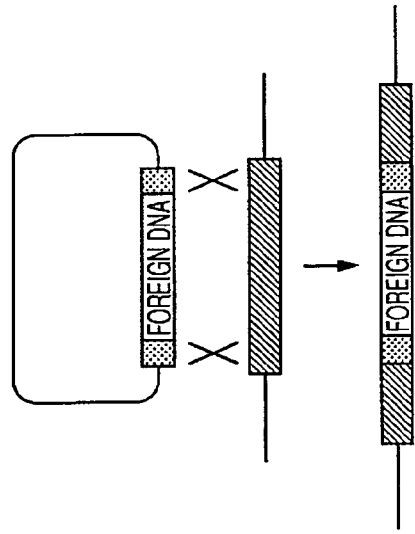
FIG. 5
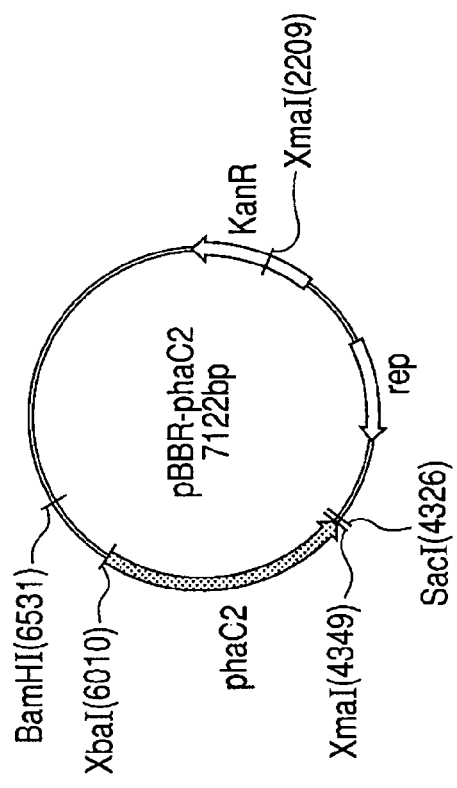
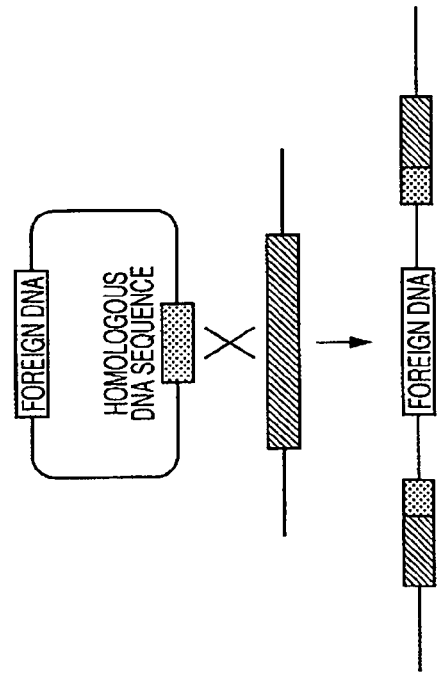
FIG. 6A
FIG. 6B

SEQUENCE LISTING

<160> NUMBER OF SEQ ID NOS: 25

<210> SEQ ID NO 1
<211> LENGTH: 2322
<212> TYPE: DNA
<213> ORGANISM: Pseudomonas sp. YN21

<400> SEQUENCE: 1

```
ggtcatgacc caactcccca ccggacatca agctgcacaa aagcctcgaa aaccctgacg      60
ctcaaatacg cgtccggcga ggaatacacc ctgcccgccg agttcctgcg cgtgcactct     120
ccttccgccg aggtccaggg ccacggcaaa cccatcctgc aatttggcaa gatcaacgta     180
ggactgagca agatagaacc cgccggtcag tacgcactga aactgacctt tgacgatggc     240
cacgacagcg gcctgttcac ctgggaatac ctctacgaac tggggcgacg tcatgacgcg     300
ctttgggacg attatcttgc cgagctaaaa gccgcaggaa aaacccgcga cccgaacgaa     360
tctgtcgtca agctgatgct ctagcctgcg cctcttgctc tttagagggc attttctaat     420
tccatctgtt tgaatgctcg gcttcagggt cgacgcctgg cccgcttgcg aaaaaaatta     480
aactcgggta accaatggac tggcaaggtc cctgcagtgc tctctgaatt aaaaaagcag     540
tgatgcagaa tcaaaggtca cccgagcagt agtacctggc aattgctgtg tgactacaca     600
gcaggaccaa ggtgctcgtc tcagggcaat ggagcgtcgt agatgagtaa caagagtaac     660
gatgagttga agtatcaagc ctctgaaaac accttggggc ttaatcctgt cgttgggctg     720
cgtggaaagg atctactggc ttctgctcga atggtgctta ggcaggccat caagcaaccg     780
gtgcacagcg tcaaacatgt cgcgcacttt ggtcttgaac tcaagaacgt actgctgggt     840
aaatccgggc tgcaaccgac cagcgatgac cgtcgcttcg ccgatccggc ctggagccag     900
aacccgctct ataaacgtta tttgcaaacc tacctggcgt ggcgcaagga actccacgac     960
tggatcgatg aaagtaacct cgcccccaag gatgtggcgc gtgggcactt cgtgatcaac    1020
ctcatgaccg aagccatggc gccgaccaac accgcggcca accggcggc agtcaaacgc     1080 tttttcgaaa ccggtggcaa aagcctgctc gacggcctct cgcacctggc caaggatctg    1140
gtacacaacg gcggcatgcc gagccaggtc aacatgggtg cattcgaggt cggcaagagc    1200
ctgggcgtga ccgaaggcgc ggtggtgttt cgcaacgatg tgctggaact gatccagtac    1260
aagccgacca ccgagcaggt atacgaacgc ccgctgctgg tggtgccgcc gcagatcaac    1320
aagttctacg ttttcgacct gagcccggac aagagcctgg cgcggttctg cctgcgcaac    1380
aacgtgcaaa cgttcatcgt cagctggcga atcccacca aggaacagcg agagtggggc    1440
ctgtcgacct acatcgaagc cctcaaggaa gcggttgatg tcgttaccgc gatcaccggc    1500
agcaaagacg tgaacatgct cggcgcctgc tccggcggca tcacttgcac cgcgctgctg    1560
ggccattacg cggcgattgg cgaaaacaag gtcaacgccc tgaccttgct ggtgagcgtg    1620
cttgatacca ccctcgacag cgatgttgcc ctgttcgtca atgaacagac ccttgaagcc    1680
gccaagcgcc actcgtacca ggccggcgta ctggaaggcc gcgacatggc gaaggtcttc    1740
gcctggatgc gccccaacga tctgatctgg aactactggg tcaacaatta cctgctaggc    1800
aacgaaccgc cggtgttcga catcctgttc tggaacaacg acaccacacg gttgcccgcg    1860
gcgttccacg gcgacctgat cgaactgttc aaaaataacc cactgattcg cccgaatgca    1920
ctggaagtgt gcggcacccc catcgacctc aagcaggtga cggccgacat cttttcccctg    1980 gccggcacca acgaccacat caccccgtgg aagtcctgct acaagtcggc gcaactgttt    2040
```

```
ggcggcaacg ttgaattcgt gctgtcgagc agcgggcata tccagagcat cctgaacccg    2100 cgggcaatc cgaaatcgcg ctacatgacc agcaccgaag tggcggaaaa tgccgatgaa     2160
tggcaagcga atgccaccaa gcataccgat tcctggtggc tgcactggca ggcctggcag    2220
gcccaacgct cgggcgagct gaaaaagtcc ccgacaaaac tgggcagcaa ggcgtatccg    2280
gcaggtgaag cggcgccagg cacgtacgtg cacgaacggt aa                       2322

<210> SEQ ID NO 2
<211> LENGTH: 1683
<212> TYPE: DNA
<213> ORGANISM: Pseudomonas sp. YN21

<400> SEQUENCE: 2
atgcgcgata aacctgcgag ggagtcacta cccacccccg ccaagttcat caacgcacaa    60
agtgcgatta ccggcctgcg tggccgggat ctggtttcga cttttgcgcag tgtcgccgcc  120 catggcctgc gccaccccgt gcacaccgcg cgacacgcct gaaactgggt ggtcaactg    180 ggacgcgtgt tgctgggcga caccctgcat cccaccaacc gcaagaccgt cgcttcgac   240 gatccggcgt ggagtctcaa tccctttat cgtcgcagcc tgcaggcgta cctgagctgg    300
cagaagcagg tcaagagctg gatcgacgaa agcaacatga gcccggatga ccgcgcccgt   360
gcgcacttcg cgttcgccct gctcaacgat gccgtgtcgc cgtccaacag cctgctcaat    420
ccgctggcga tcaaggaaat cttcaactcc ggcggcaaca gcctggtgcg cgggatcggc    480
catctggtcg atgacctctt gcacaacgat ggcttgcccc ggcaagtcac caggcatgca    540
ttcgaggttg gcaagaccgt cgccaccacc accggcgccg tggtgtttcg caacgagctg    600
ctggagctga tccaatacaa gccgatgagc gaaaagcagt attccaaacc gctgctggtg    660
gtgccgccac agatcaacaa gtactacatt tttgacctca gcccccataa cagcttcgtc    720
cagttcgcgc tcaagaacgg cctgcaaacc ttcgtcatca gctggcgcaa tccggatgta    780
cgtcaccgcg aatggggcct gtcgacctac gtcgaagcgg tggaagaagc catgaatgtc    840
tgccgggcaa tcaccggcgc gcgcgaggtc aacctgatgg gcgcctgcgc tggcgggctg    900
accattgctg ccctgcaggg ccacttgcaa gccaagcgac agctgcgccg cgtctccagc    960
gcgacgtacc tggtgagcct gctcgacagc caactggaca gcccggccac actcttcgcc    1020
gacgaacaga ccctggaggc ggccaagcgc cgctcctacc agaaaggtgt gctggaaggc   1080
cgcgacatgg ccaaggtttt cgcctggatg cgccccaacg atttgatctg gagctacttc    1140
gtcaacaatt acctgatggg caaggagccg ccggcgttcg acattctcta ctggaacaat    1200
gacaacacac gcctgccggc cgccctgcat ggtgacttgc tggacttctt caagcacaac    1260
ccgctgagcc atccgggtgg cctggaagtg tgcggcaccc cgatcgactt gcaaaaggtc    1320
accgtcgaca gtttcagcgt ggccggcatc aacgatcaca tcacgccgtg ggacgcggtg    1380
tatcgctcaa ccctgttgct cggtggcgag cgtcgctttg tcctggccaa cagcggtcat    1440
gtgcagagca ttctcaaccc gccgaacaat ccgaaagcca actacctcga aggtgcaaaa    1500
ctaagcagcg accccagggc ctggtactac gacgccaagc ccgtcgacgg tagctggtgg    1560
acgcaatggc tgggctggat tcaggagcgc tcgggcgcgc aaaaagaaac ccacatggcc    1620
ctcggcaatc agaattatcc accgatggag gcggcgcccg ggacttacgt gcgcgtgcgc    1680
tga                                                                   1683

<210> SEQ ID NO 3
```

```
<211> LENGTH: 42
<212> TYPE: DNA
<213> ORGANISM: Artificial Sequence
<220> FEATURE:
<223> OTHER INFORMATION: PCR primer, YC1-upN

<400> SEQUENCE: 3
attattcccg ggacccgcga cccgaacgaa tctgtcgtca ag          42

<210> SEQ ID NO 4
<211> LENGTH: 42
<212> TYPE: DNA
<213> ORGANISM: Artificial Sequence
<220> FEATURE:
<223> OTHER INFORMATION: PCR primer, YC1-2/3C

<400> SEQUENCE: 4
attatttcta gacaggctct tgccgacctc gaatgcaccc at          42

<210> SEQ ID NO 5
<211> LENGTH: 42
<212> TYPE: DNA
<213> ORGANISM: Artificial Sequence
<220> FEATURE:
<223> OTHER INFORMATION: PCR primer, YC2-2/3N

<400> SEQUENCE: 5
attatttcta gattgatctg gagctacttc gtcaacaatt ac          42

<210> SEQ ID NO 6
<211> LENGTH: 42
<212> TYPE: DNA
<213> ORGANISM: Artificial Sequence
<220> FEATURE:
<223> OTHER INFORMATION: PCR primer, YC2-Ct

<400> SEQUENCE: 6
attattcccg ggcgccgcct ccatcggtgg ataattctga tt          42

<210> SEQ ID NO 7
<211> LENGTH: 7253
<212> TYPE: DNA
<213> ORGANISM: Artificial Sequence
<220> FEATURE:
<223> OTHER INFORMATION: plasmid pEX-phaC

<400> SEQUENCE: 7
gacgaaaggg cctcgtgata cgcctatttt tataggttaa tgtcatgata ataatggttt     60
cttagacgtc aggtggcact tttcggggaa atgtgcgcgg aaccctatt tgtttatttt     120 tctaaataca ttcaaatatg tatccgctca tgagacaata accctgataa atgcttcaat    180
aatattgaaa aaggaagagt atgagtattc aacatttccg tgtcgccctt attcccttt    240 ttgcggcatt ttgccttcct gttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacgatg     540 gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
```

```
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttttaatt taaaaggatc taggtgaaga   1140
tccttttga taatctcatg accaaaatcc cttaacgtga gttttcgttc cactgagcgt   1200
cagacccgt agaaaagatc aaaggatctt cttgagatcc ttttttttctg cgcgtaatct   1260
gctgcttgca acaaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg ataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcaccccca ggctttacac tttatgcttc   2160
cggctcgtat gttgtgtgga attgtgagcg gataacaatt tcacacagga aacagctatg   2220
accatgatta cgccaagctc tagggataac agggtaatcc cgggcgccgc ctccatcggt   2280
ggataattct gattgccgag gccatgtggg gtttcttttt gcgcgcccga gcgctcctga   2340
atccagccca gccattgcgt ccaccagcta ccgtcgacgg gcttggcgtc gtagtaccag   2400
gccctggggt cgctgcttag ttttgcacct tcgaggtagt tggctttcgg attgttcggc   2460
gggttgagaa tgctctgcac atgaccgctg ttggccagga caaagcgacg ctcgccaccg   2520
agcaacaggg ttgagcgata caccgcgtcc cacggcgtga tgtgatcgtt gatgccggcc   2580
acgctgaaac tgtcgacggt gaccttttgc aagtcgatcg gggtgccgca cacttccagg   2640
ccacccggat ggctcagcgg gttgtgcttg aagaagtcca gcaagtcacc atgcagggcg   2700
gccggcaggc gtgtgttgtc attgttccag tagagaatgt cgaacgccgg cggctccttg   2760
cccatcaggt aattgttgac gaagtagctc cagatcaatc tagacaggct cttgccgacc   2820
tcgaatgcac ccatgttgac ctggctcggc atgccgccgt tgtgtaccag atccttggcc   2880
aggtgcgaga ggccgtcgag caggcttttg ccaccggttt cgaaaaagcg tttgactgcc   2940
gccgggttgg ccgcggtgtt ggtcggcgcc atgcttcgg tcatgaggtt gatcacgaag   3000
tgcccacgcg ccacatcctt ggggggcgagg ttactttcat cgatccagtc gtggagttcc   3060
```

```
ttgcgccacg ccaggtaggt ttgcaaataa cgtttataga gcgggttctg gctccaggcc    3120
ggatcggcga agcgacggtc atcgctggtc ggttgcagcc cggatttacc cagcagtacg    3180
ttcttgagtt caagaccaaa gtgcgcgaca tgtttgacgc tgtgcaccgg ttgcttgatg    3240
gcctgcctaa gcaccattcg agcagaagcc agtagatcct ttccacgcag cccaacgaca    3300
ggattaagcc ccaaggtgtt ttcagaggct tgatacttca actcatcgtt actcttgtta    3360
ctcatctacg acgctccatt gccctgagac gagcaccttg gtcctgctgt gtagtcacac    3420
agcaattgcc aggtactact gctcgggtga cctttgattc tgcatcactg ctttttttaat   3480
tcagagagca ctgcagggac cttgccagtc cattggttac ccgagtttaa tttttttcgc    3540
aagcgggcca ggcgtcgacc ctgaagccga gcattcaaac agatggaatt agaaaatgcc    3600
ctctaaagag caagaggcgc aggctagagc atcagcttga cgacagattc gttcgggtcg    3660
cgggtcccgg gtagggataa cagggtaatg agcttggcac tggccgtcgt tttacaacgt    3720
cgtgactggg aaaaccctgg cgttacccaa cttaatcgcc ttgcagcaca tccccctttc    3780
gccagctggc gtaatagcga agaggcccgc accgatcgcc cttcccaaca gttgcgcagc    3840
ctgaatggcg aatggcgagc ttggctgttt tggcggatga gaagagattt tcagcctgat    3900
acagattaaa tcagaacgca gaagcggtct gataaaacag aatttgcctg gcggcagtag    3960
cgcggtggtc ccacctgacc ccatgccgaa ctcagaagtg aaacgccgta gcgccgatgg    4020
tagtgtgggg tctccccatg cgagagtagg gaactgccag gcatcaaata aaacgaaagg    4080
ctcagtcgaa agactgggcc tttcgtttta tctgttgttt gtcggtgaac gctctcctga    4140
gtaggacaaa tccgccggga gcggatttga acgttgcgaa gcaacggccc ggagggtggc    4200
gggcaggacg cccgccataa actgccaggc atcaaattaa gcagaaggcc atcctgacgg    4260
atggcctttt tgcgtttcta caaactcttt ttgtttattt ttctaaatac attcaaatat    4320
gcatgcgcct gatgcggtat tttctcctta cgcatatcga catccgccct caccgccagg    4380
aacgcaaccg cagcctcatc acgccggcgc ttcttggccg cgcggattc aacccactcg     4440
gccagctcgt cggtgtagct cttttggcatc gtctctcgcc tgtcccctca gttcagtaat    4500
ttcctgcatt tgcctgtttc cagtcggtag atattccaca aaacagcagg gaagcagcgc    4560
ttttccgctg cataaccctg cttcggggtc attatagcga tttttttcggt atatccatcc    4620
tttttcgcac gatatacagg atttttgccaa agggttcgtg tagactttcc ttggtgtatc    4680
caacggcgtc agccgggcag gataggtgaa gtaggcccac ccgcgagcgg gtgttccttc    4740
ttcactgtcc cttattcgca cctggcggtg ctcaacggga atcctgctct gcgaggctgg    4800
ccggctaccg ccggcgtaac agatgagggc aagcggatgg ctgatgaaac caagccaacc    4860
aggaagggca gcccacctat caaggtgtac tgccttccag acgaacgaag agcgattgag    4920
gaaaaggcgg cggcggccgg catgagcctg tcggcctacc tgctggccgt cggccagggc    4980
tacaaaatca cgggcgtcgt ggactatgag cacgtccgcg agctggcccg catcaatggc    5040
gacctgggcc gcctgggcgg cctgctgaaa ctctggctca ccgacgaccc gcgcacggcg    5100
cggttcggtg atgccacgat cctcgccctg ctggcgaaga tcgactctag ctagaggatc    5160
gatccttttt aacccatcac atatacctgc cgttcactat tatttagtga aatgagatat    5220
tatgatatttt tctgaattgt gattaaaaag gcaactttat gcccatgcaa cagaaactat    5280
aaaaaataca gagaatgaaa agaaacagat agattttttta gttctttagg cccgtagtct    5340
gcaaatcctt ttatgatttt ctatcaaaca aagaggaaaa atagaccagt tgcaatccaa    5400
acgagagtct aatagaatga ggtcgaaaag taaatcgcgc gggtttgtta ctgataaagc    5460
```

```
aggcaagacc taaaatgtgt aaagggcaaa gtgtatactt tggcgtcacc ccttacatat   5520
tttaggtctt tttttattgt gcgtaactaa cttgccatct tcaaacagga gggctggaag   5580
aagcagaccg ctaacacagt acataaaaaa ggagacatga acgatgaaca tcaaaaagtt   5640
tgcaaaacaa gcaacagtat taaccttta c taccgcactg ctggcaggag cgcaactca    5700 agcgtttgcg aaagaaacga accaaaagcc atataaggaa acatacgca tttcccatat    5760 tacacgccat gatatgctgc aaatccctga acagcaaaaa aatgaaaaat atcaagttcc   5820
tgagttcgat tcgtccacaa ttaaaaatat ctcttctgca aaaggcctgg acgtttggga   5880
cagctggcca ttacaaaacg ctgacggcac tgtcgcaaac tatcacggct accacatcgt   5940
ctttgcatta gccggagatc ctaaaaatgc ggatgacaca tcgatttaca tgttctatca   6000
aaaagtcggc gaaacttcta ttgacagctg gaaaaacgct ggccgcgtct ttaaagacag   6060
cgacaaattc gatgcaaatg attctatcct aaaagaccaa acacaagaat ggtcaggttc   6120
agccacattt acatctgacg gaaaaatccg tttattctac actgatttct ccggtaaaca   6180
ttacggcaaa caaacactga caactgcaca agttaacgta tcagcatcag acagctcttt   6240
gaacatcaac ggtgtagagg attataaatc aatctttgac ggtgacggaa aaacgtatca   6300
aaatgtacag cagttcatcg atgaaggcaa ctacagctca ggcgacaacc atacgctgag   6360
agatcctcac tacgtagaag ataaaggcca caaatactta gtatttgaag caaacactgg   6420
aactgaagat ggctaccaag gcgaagaatc tttatttaac aaagcatact atggcaaaag   6480
cacatcattc ttccgtcaag aaagtcaaaa acttctgcaa agcgataaaa aacgcacggc   6540
tgagttagca acggcgctc tcggtatgat tgagctaaac gatgattaca cactgaaaaa    6600
agtgatgaaa ccgctgattg catctaacac agtaacagat gaaattgaac gcgcgaacgt   6660
ctttaaaatg aacggcaaat ggtatctgtt cactgactcc cgcggatcaa aaatgacgat   6720
tgacggcatt acgtctaacg atatttacat gcttggttat gtttctaatt ctttaactgg   6780
cccatacaag ccgctgaaca aaactggcct tgtgttaaaa atggatcttg atcctaacga   6840
tgtaaccttt acttactcac acttcgctgt acctcaagcg aaaggaaaca atgtcgtgat   6900
tacaagctat atgacaaaca gaggattcta cgcagacaaa caatcaacgt tgcgcctag   6960 cttcctgctg aacatcaaag gcaagaaaac atctgttgtc aaagacagca tccttgaaca   7020
aggacaatta acagttaaca ataaaaacg caaaagaaaa tgccgattat ggtgcactct   7080
cagtacaatc tgctctgatg ccgcatagtt aagccagccc cgacaccagc caacacccgc   7140
tgacgcgccc tgacgggctt gtctgctccc ggcatccgct tacagacaag ctgtgaccgt   7200
ctccgggagc tgcatgtgtc agaggttttc accgtcatca ccgaaacgcg cga          7253
```

<210> SEQ ID NO 8
<211> LENGTH: 42
<212> TYPE: DNA
<213> ORGANISM: Artificial Sequence
<220> FEATURE:
<223> OTHER INFORMATION: PCR primer, gen-f1

<400> SEQUENCE: 8

```
attatttcta gaaggacaga aatgcctcga cttcgctgct gc                       42
```

<210> SEQ ID NO 9
<211> LENGTH: 45
<212> TYPE: DNA
<213> ORGANISM: Artificial Sequence
<220> FEATURE:

<223> OTHER INFORMATION: PCR primer, gen-r1

<400> SEQUENCE: 9
attatttcta gattaggtgg cggtacttgg gtcgatatca aagtg        45

<210> SEQ ID NO 10
<211> LENGTH: 8093
<212> TYPE: DNA
<213> ORGANISM: Artificial Sequence
<220> FEATURE:
<223> OTHER INFORMATION: PHA synthase gene-targeting vector pPC12

<400> SEQUENCE: 10

| | | |
|---|---|---|
| gacgaaaggg cctcgtgata cgcctatttt tataggttaa tgtcatgata ataatggttt | 60 |
| cttagacgtc aggtggcact tttcggggaa atgtgcgcgg aaccccuatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attcccuttt | 240 |
| ttgcggcatt ttgccttcct gttttugctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga ccacgatgcc tgtagcaa tgcaacaac gttgcgcaaa ctattaactg | 780 |
| gcgaactact tactctagct cccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca acaaaaaaa ccaccgctac cagcggtggt ttgtttgccg gatcaagagc | 1320 |
| taccaactct ttttccgaag gtaactggct tcagcagagc gcagatacca atactgtcc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg gtcgggctga cgggggggtt | 1560 |
| cgtgcacaca gcccagcttg gagcgaacga cctacaccga actgagatac ctacagcgtg | 1620 |
| agctatgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg attttgtga tgctcgtcag | 1800 |
| gggggcggag cctatggaaa aacgccagca acgcggcctt tttacggttc ctggccttt | 1860 |
| gctggccttt tgctcacatg ttctttcctg cgttatcccc tgattctgtg ataaccgta | 1920 |

```
ttaccgcctt tgagtgagct gataccgctc gccgcagccg aacgaccgag cgcagcgagt      1980
cagtgagcga ggaagcggaa gagcgcccaa tacgcaaacc gcctctcccc gcgcgttggc      2040
cgattcatta atgcagctgg cacgacaggt ttcccgactg gaaagcgggc agtgagcgca      2100
acgcaattaa tgtgagttag ctcactcatt aggcacccca ggctttacac tttatgcttc      2160
cggctcgtat gttgtgtgga attgtgagcg gataacaatt tcacacagga aacagctatg      2220
accatgatta cgccaagctc tagggataac agggtaatcc cgggcgccgc ctccatcggt      2280
ggataattct gattgccgag ggccatgtgg gtttcttttt gcgcgcccga gcgctcctga      2340
atccagccca gccattgcgt ccaccagcta ccgtcgacgg gcttggcgtc gtagtaccag      2400
gccctggggt cgctgcttag ttttgcacct tcgaggtagt tggctttcgg attgttcggc      2460
gggttgagaa tgctctgcac atgaccgctg ttggccagga caaagcgacg ctcgccaccg      2520
agcaacaggg ttgagcgata caccgcgtcc cacggcgtga tgtgatcgtt gatgccggcc      2580
acgctgaaac tgtcgacggt gaccttttgc aagtcgatcg gggtgccgca cacttccagg      2640
ccacccggat ggctcagcgg gttgtgcttg aagaagtcca gcaagtcacc atgcagggcg      2700
gccggcaggc gtgtgttgtc attgttccag tagagaatgt cgaacgccgg cggctccttg      2760
cccatcaggt aattgttgac gaagtagctc cagatcaatc tagaaggaca gaaatgcctc      2820
gacttcgctg ctgcccaagg ttgccgggtg acgcacaccg tggaaacgga tgaaggcacg      2880
aacccagttg acataagcct gttcggttcg taaactgtaa tgcaagtagc gtatgcgctc      2940
acgcaactgg tccagaacct tgaccgaacg cagcggtggt aacggcgcag tggcggtttt      3000
catggcttgt tatgactgtt tttttgtaca gtctatgcct cgggcatcca agcagcaagc      3060
gcgttacgcc gtgggtcgat gtttgatgtt atggagcagc aacgatgtta cgcagcagca      3120
acgatgttac gcagcagggc agtcgcccta aacaaagtt aggtggctca agtatgggca      3180
tcattcgcac atgtaggctc ggccctgacc aagtcaaatc catgcgggct gctcttgatc      3240
ttttcggtcg tgagttcgga cgtagccca ctactccca acatcagccg gactccgatt      3300
acctcgggaa cttgctccgt agtaagacat tcatcgcgct tgctgccttc gaccaagaag      3360
cggttgttgg cgctctcgcg gcttacgttc tgcccaggtt tgagcagccg cgtagtgaga      3420
tctatatcta tgatctcgca gtctccggcg agcaccggag gcagggcatt gccaccgcgc      3480
tcatcaatct cctcaagcat gaggccaacg cgcttggtgc ttatgtgatc tacgtgcaag      3540
cagattacgg tgacgatccc gcagtggctc tctatacaaa gttgggcata cgggaagaag      3600
tgatgcactt tgatatcgac ccaagtaccg ccacctaatc tagacaggct cttgccgacc      3660
tcgaatgcac ccatgttgac ctggctcggc atgccgccgt tgtgtaccag atccttggcc      3720
aggtgcgaga ggccgtcgag caggcttttg ccaccggttt cgaaaaagcg tttgactgcc      3780
gccgggttgg ccgcggtgtt ggtcggcgcc atggcttcgg tcatgaggtt gatcacgaag      3840
tgcccacgcg ccacatcctt gggggcgagg ttactttcat cgatccagtc gtggagttcc      3900
ttgcgccacg ccaggtaggt ttgcaaataa cgtttataga gcgggttctg gctccaggcc      3960
ggatcggcga agcgacggtc atcgctggtc ggttgcagcc cggatttacc cagcagtacg      4020
ttcttgagtt caagaccaaa gtgcgcgaca tgtttgacgc tgtgcaccgg ttgcttgatg      4080
gcctgcctaa gcaccattcg agcagaagcc agtagatcct ttccacgcag cccaacgaca      4140
ggattaagcc ccaaggtgtt ttcagaggct tgatacttca actcatcgtt actcttgtta      4200
ctcatctacg acgctccatt gccctgagac gagcaccttg gtcctgctgt gtagtcacac      4260
```

```
agcaattgcc aggtactact gctcgggtga cctttgattc tgcatcactg cttttttaat    4320
tcagagagca ctgcagggac cttgccagtc cattggttac ccgagtttaa ttttttttcgc   4380 aagcgggcca ggcgtcgacc ctgaagccga gcattcaaac agatggaatt agaaaatgcc   4440
ctctaaagag caagaggcgc aggctagagc atcagcttga cgacagattc gttcgggtcg   4500
cgggtcccgg gtagggataa cagggtaatg agcttggcac tggccgtcgt tttacaacgt   4560
cgtgactggg aaaaccctgg cgttacccaa cttaatcgcc ttgcagcaca tccccctttc   4620
gccagctggc gtaatagcga gaggcccgca ccgatcgccc ttcccaaca gttgcgcagc    4680 ctgaatggcg aatggcgagc ttggctgttt tggcggatga gaagatttt cagcctgat    4740 acagattaaa tcagaacgca gaagcggtct gataaaacag aatttgcctg gcggcagtag  4800
cgcggtggtc ccacctgacc ccatgccgaa ctcagaagtg aaacgccgta gcgccgatgg  4860
tagtgtgggg tctccccatg cgagagtagg gaactgccag gcatcaaata aaacgaaagg  4920
ctcagtcgaa agactgggcc tttcgtttta tctgttgttt gtcggtgaac gctctcctga  4980
gtaggacaaa tccgccggga gcggatttga acgttgcgaa gcaacggccc ggagggtggc  5040
gggcaggacg cccgccataa actgccaggc atcaaattaa gcagaaggcc atcctgacgg  5100
atggcctttt tgcgtttcta caaactctt  ttgtttattt ttctaaatac attcaaatat   5160
gcatgcgcct gatgcggtat tttctcctta cgcatatcga catccgccct caccgccagg  5220
aacgcaaccg cagcctcatc acgccggcgc ttcttggccg cgcgggattc aacccactcg  5280
gccagctcgt cggtgtagct cttttggcatc gtctctcgcc tgtcccctca gttcagtaat  5340
ttcctgcatt tgcctgtttc cagtcggtag atattccaca aaacagcagg gaagcagcgc  5400 tttttccgctg cataaccctg cttcggggtc attatagcga ttttttcggt atatccatcc  5460
tttttcgcac gatatacagg attttgccaa agggttcgtg tagactttcc ttggtgtatc   5520
caacggcgtc agccgggcag gataggtgaa gtaggcccac ccgcgagcgg gtgttccttc   5580
ttcactgtcc cttattcgca cctggcggtg ctcaacggga atcctgctct gcgaggctgg  5640
ccggctaccg ccggcgtaac agatgagggc aagcggatgg ctgatgaaac caagccaacc  5700
aggaagggca gcccacctat caaggtgtac tgccttccag acgaacgaag agcgattgag  5760
gaaaaggcgg cggcggccgg catgagcctg tcggcctacc tgctggccgt cggccagggc  5820
tacaaaatca cgggcgtcgt ggactatgag cacgtccgcg agctggcccg catcaatggc  5880
gacctgggcc gcctgggcgg cctgctgaaa ctctggctca ccgacgaccc cgcgcacggcg 5940 cggttcggtg atgccacgat cctcgccctg ctggcgaaga tcgactctag ctagaggatc  6000
gatccttttt aacccatcac atatacctgc cgttcactat tatttagtga aatgagatat  6060
tatgatattt tctgaattgt gattaaaaag gcaactttat gcccatgcaa cagaaactat  6120
aaaaaataca gagaatgaaa agaaacagat agatttttta gttctttagg cccgtagtct  6180
gcaaatcctt ttatgatttt ctatcaaaca aagaggaaa atagaccagt tgcaatccaa   6240
acgagagtct aatagaatga ggtcgaaaag taaatcgcgc gggtttgtta ctgataaagc  6300
aggcaagacc taaaatgtgt aaagggcaaa gtgtatactt tggcgtcacc ccttacatat  6360
tttaggtctt tttttattgt gcgtaactaa cttgccatct tcaaacagga gggctggaag  6420
aagcagaccg ctaacacagt acataaaaaa ggagacatga acgatgaaca tcaaaaagtt  6480
tgcaaaacaa gcaacagtat taacctttac taccgcactg ctggcaggag gcgcaactca  6540
agcgtttgcg aaagaaacga accaaaagcc atataaggaa acatacgcca tttcccctat  6600
tacacgccat gatatgctgc aaatccctga acagcaaaaa aatgaaaaat atcaagttcc  6660
```

-continued

```
tgagttcgat tcgtccacaa ttaaaaatat ctcttctgca aaaggcctgg acgtttggga    6720
cagctggcca ttacaaaacg ctgacggcac tgtcgcaaac tatcacggct accacatcgt    6780
ctttgcatta gccggagatc ctaaaaatgc ggatgcacaa tcgatttaca tgttctatca    6840
aaaagtcggc gaaacttcta ttgcagctg gaaaaacgct ggccgcgtct ttaaagacag     6900
```
```
cgacaaattc gatgcaaatg attctatcct aaaagaccaa acacaagaat ggtcaggttc    6960
agccacattt acatctgacg gaaaaatccg tttattctac actgatttct ccggtaaaca    7020
ttacggcaaa caaacactga caactgcaca agttaacgta tcagcatcag acagctcttt    7080
gaacatcaac ggtgtagagg attataaatc aatctttgac ggtgacggaa aaacgtatca    7140
aaatgtacag cagttcatcg atgaaggcaa ctacagctca ggcgacaacc atacgctgag    7200
agatcctcac tacgtagaag ataaaggcca caaatactta gtatttgaag caaacactgg    7260
aactgaagat ggctaccaag gcgaagaatc tttatttaac aaagcatact atggcaaaag    7320
cacatcattc ttccgtcaag aaagtcaaaa acttctgcaa agcgataaaa aacgcacggc    7380
tgagttagca acggcgctc tcggtatgat tgagctaaac gatgattaca cactgaaaaa     7440
agtgatgaaa ccgctgattg catctaacac agtaacagat gaaattgaac gcgcgaacgt    7500
ctttaaaatg aacggcaaat ggtatctgtt cactgactcc gcggatcaa aaatgacgat     7560 tgacggcatt acgtctaacg atatttcat gcttggttat gtttctaatt ctttaactgg     7620
cccatacaag ccgctgaaca aaactggcct tgtgttaaaa atggatcttg atcctaacga    7680
tgtaaccttt acttactcac acttcgctgt acctcaagcg aaaggaaaca atgtcgtgat    7740
tacaagctat atgacaaaca gaggattcta cgcagacaaa caatcaacgt ttgcgcctag    7800
cttcctgctg aacatcaaag gcaagaaaac atctgttgtc aaagacagca tccttgaaca    7860
aggacaatta acagttaaca ataaaaaacg caaagaaaa tgccgattat ggtgcactct     7920
cagtacaatc tgctctgatg ccgcatagtt aagccagccc cgacaccgc caacaccgc      7980 tgacgcgccc tgacgggctt gtctgctccc ggcatccgct tacagacaag ctgtgaccgt    8040
ctccgggagc tgcatgtgtc agaggttttc accgtcatca ccgaaacgcg cga           8093
```

<210> SEQ ID NO 11
<211> LENGTH: 40
<212> TYPE: DNA
<213> ORGANISM: Artificial Sequence
<220> FEATURE:
<223> OTHER INFORMATION: PCR primer, YC1-upN-f1

<400> SEQUENCE: 11
aataatggat ccttccgccg aggtccaggg ccacggcaaa    40

<210> SEQ ID NO 12
<211> LENGTH: 30
<212> TYPE: DNA
<213> ORGANISM: Artificial Sequence
<220> FEATURE:
<223> OTHER INFORMATION: PCR primer, YC1-N-r1

<400> SEQUENCE: 12
ctagaacgct ccattgccct gagacgagca    30

<210> SEQ ID NO 13
<211> LENGTH: 42
<212> TYPE: DNA
<213> ORGANISM: Artificial Sequence
<220> FEATURE:

```
<223> OTHER INFORMATION: PCR primer, YC1-C-r1

<400> SEQUENCE: 13
attattgagc tcttaccgtt cgtgcacgta cgtgcctggc gc                              42

<210> SEQ ID NO 14
<211> LENGTH: 30
<212> TYPE: DNA
<213> ORGANISM: Artificial Sequence
<220> FEATURE:
<223> OTHER INFORMATION: PCR primer, pBBR/Bam-f1

<400> SEQUENCE: 14
aaaggccgta ggatccagct gaacggtctg                                           30

<210> SEQ ID NO 15
<211> LENGTH: 42
<212> TYPE: DNA
<213> ORGANISM: Artificial Sequence
<220> FEATURE:
<223> OTHER INFORMATION: PCR primer, pBBR/Sac-r1

<400> SEQUENCE: 15
gcccccgagc tcaccatggg caaatattat acgcaaggcg ac                             42

<210> SEQ ID NO 16
<211> LENGTH: 7119
<212> TYPE: DNA
<213> ORGANISM: Artificial Sequence
<220> FEATURE:
<223> OTHER INFORMATION: phaC1 expression vector pBBR-phaC1

<400> SEQUENCE: 16
ctcggtcggg ccgtctcttg ggcttgatcg gccttcttgc gcatctcacg cgctcctgcg          60
gcggcctgta gggcaggctc atacccctgc cgaaccgctt ttgtcagccg gtcggccacg         120
gcttccggcg tctcaacgcg cttttgagatt cccagctttt cggccaatcc ctgcggtgca        180
taggcgcgtg gctcgaccgc ttgcgggctg atggtgacgt ggcccactgg tggccgctcc        240
agggcctcgt agaacgcctg aatgcgcgtg tgacgtgcct tgctgccctc gatgcccgt         300 tgcagcccta gatcggccac agcggccgca aacgtggtct ggtcgcgggt catctgcgct        360
ttgttgccga tgaactcctt ggccgacagc ctgccgtcct gcgtcagcgg caccacgaac        420
gcggtcatgt gcgggctggt ttcgtcacgg tggatgctgg ccgtcacgat gcgatccgcc        480
ccgtacttgt ccgccagcca cttgtgcgcc ttctcgaaga acgccgcctg ctgttcttgg        540
ctggccgact ccaccattc cgggctggcc gtcatgacgt actcgaccgc caacacagcg         600
tccttgcgcc gcttctctgg cagcaactcg cgcagtcggc ccatcgcttc atcggtgctg        660
ctggccgccc agtgctcgtt ctctggcgtc ctgctggcgt cagcgttggg cgtctcgcgc        720
tcgcggtagg cgtgcttgag actggccgcc acgttgccca ttttcgccag cttcttgcat        780
cgcatgatcg cgtatgccgc catgcctgcc cctccctttt ggtgtccaac cggctcgacg        840
ggggcagcgc aaggcggtgc ctccggcggg ccactcaatg cttgagtata ctcactagac        900
tttgcttcgc aaagtcgtga ccgcctacgg cggctgcggc gccctacggg cttgctctcc        960
gggcttcgcc ctgcgcggtc gctgcgctcc cttgccagcc cgtggatatg tggacgatgg       1020
ccgcgagcgg ccaccggctg gctcgcttcg ctcggcccgt ggacaaccct gctggacaag       1080
ctgatggaca ggctgcgcct gcccacgagc ttgaccacag ggattgccca ccggctaccc       1140
agccttcgac cacataccca ccggctccaa ctgcgcggcc tgcggccttg ccccatcaat       1200
```

```
tttttttaatt ttctctgggg aaaagcctcc ggcctgcggc ctgcgcgctt cgcttgccgg    1260
ttggacacca agtggaaggc gggtcaaggc tcgcgcagcg accgcgcagc ggcttggcct    1320
tgacgcgcct ggaacgaccc aagcctatgc gagtgggggc agtcgaaggc gaagcccgcc    1380
cgcctgcccc ccgagacctg cagggggggg ggggcgctga ggtctgcctc gtgaagaagg    1440
tgttgctgac tcataccagg cctgaatcgc cccatcatcc agccagaaag tgagggagcc    1500
acggttgatg agagctttgt tgtaggtgga ccagttggtg attttgaact tttgctttgc    1560
cacggaacgg tctgcgttgt cgggaagatg cgtgatctga tccttcaact cagcaaaagt    1620
tcgatttatt caacaaagcc gccgtcccgt caagtcagcg taatgctctg ccagtgttac    1680
aaccaattaa ccaattctga ttagaaaaac tcatcgagca tcaaatgaaa ctgcaattta    1740
ttcatatcag gattatcaat accatatttt tgaaaagcc gtttctgtaa tgaaggagaa    1800
aactcaccga ggcagttcca taggatggca agatcctggt atcggtctgc gattccgact    1860
cgtccaacat caatacaacc tattaatttc ccctcgtcaa aataaggtt atcaagtgag    1920 aaatcaccat gagtgacgac tgaatccggt gagaatggca aaagcttatg catttctttc    1980
cagacttgtt caacaggcca gccattacgc tcgtcatcaa aatcactcgc atcaaccaaa    2040
ccgttattca ttcgtgattg cgcctgagcg agacgaaata cgcgatcgct gttaaaagga    2100
caattacaaa caggaatcga atgcaaccgg cgcaggaaca ctgccagcgc atcaacaata    2160
ttttcacctg aatcaggata ttcttctaat acctggaatg ctgttttccc ggggatcgca    2220
gtggtgagta accatgcatc atcaggagta cggataaaat gcttgatggt cggaagaggc    2280
ataaattccg tcagccagtt tagtctgacc atctcatctg taacatcatt ggcaacgcta    2340
cctttgccat gtttcagaaa caactctggc gcatcgggct tcccatacaa tcgatagatt    2400
gtcgcacctg attgcccgac attatcgcga gcccatttat acccatataa atcagcatcc    2460
atgttggaat ttaatcgcgg cctcgagcaa gacgtttccc gttgaatatg gctcataaca    2520 cccttgtat tactgtttat gtaagcagac agttttattg ttcatgatga tatatttta    2580 tcttgtgcaa tgtaacatca gagattttga gacacaacgt ggctttcccc cccccccctg    2640
caggtcccga gcctcacggc ggcgagtgcg ggggttccaa gggggcagcg ccaccttggg    2700
caaggccgaa ggccgcgcag tcgatcaaca agccccggag gggccacttt ttgccggagg    2760
gggagccgcg ccgaaggcgt gggggaaccc cgcaggggtg cccttctttg ggcaccaaag    2820
aactagatat agggcgaaat gcgaaagact taaaatcaa caacttaaaa aaggggggta    2880
cgcaacagct cattgcggca ccccccgcaa tagctcattg cgtaggttaa agaaaatctg    2940
taattgactg ccacttttac gcaacgcata attgttgtcg cgctgccgaa aagttgcagc    3000
tgattgcgca tggtgccgca accgtgcggc accctaccgc atggagataa gcatggccac    3060
gcagtccaga gaaatcggca ttcaagccaa gaacaagccc ggtcactggg tgcaaacgga    3120
acgcaaagcg catgaggcgt gggccgggct tattgcgagg aaacccacgg cggcaatgct    3180
gctgcatcac ctcgtggcgc agatgggcca ccagaacgcc gtggtggtca gccagaagac    3240
actttccaag ctcatcggac gttctttgcg gacggtccaa tacgcagtca aggacttggt    3300
ggccgagcgc tggatctccg tcgtgaagct caacggcccc ggcaccgtgt cggcctacgt    3360
ggtcaatgac cgcgtggcgt ggggccagcc ccgcgaccag ttgcgcctgt cggtgttcag    3420
tgccgccgtg gtggttgatc acgacgacca ggacgaatcg ctgttggggc atggcgacct    3480
gcgccgcatc ccgaccctgt atccgggcga gcagcaacta ccgaccggcc ccggcgagga    3540
```

```
gccgcccagc cagcccggca ttccgggcat ggaaccagac ctgccagcct tgaccgaaac   3600
ggaggaatgg gaacggcgcg ggcagcagcg cctgccgatg cccgatgagc cgtgttttct   3660
ggacgatggc gagccgttgg agccgccgac acgggtcacg ctgccgcgcc ggtagcactt   3720
gggttgcgca gcaacccgta agtgcgctgt tccagactat cggctgtagc cgcctcgccg   3780
ccctatacct tgtctgcctc cccgcgttgc gtcgcggtgc atggagccgg gccacctcga   3840
cctgaatgga agcggcggc acctcgctaa cggattcacc gttttatca ggctctggga   3900 ggcagaataa atgatcatat cgtcaattat tacctccacg gggagagcct gagcaaactg   3960
gcctcaggca tttgagaagc acacggtcac actgcttccg gtagtcaata aaccggtaaa   4020
ccagcaatag acataagcgg ctatttaacg accctgccct gaaccgacga ccgggtcgaa   4080
tttgctttcg aatttctgcc attcatccgc ttattatact tattcaggcg tagcaccagg   4140
cgtttaaggg caccaataac tgccttaaaa aaattacgcc ccgccctgcc actcatcgca   4200
gtactgttgt aattcattaa gcattctgcc gacatggaag ccatcacaga cggcatgatg   4260
aacctgaatc gccagcggca tcagcacctt gtcgccttgc gtataatatt tgcccatggt   4320
gagctcttac cgttcgtgca cgtacgtgcc tggcgccgct tcacctgccg gatacgcctt   4380
gctgcccagt tttgtcgggg acttttttcag ctcgcccgag cgttgggcct gccaggcctg   4440
ccagtgcagc caccaggaat cggtatgctt ggtggcattc gcttgccatt catcggcatt   4500
ttccgccact tcggtgctgg tcatgtagcg cgatttcgga ttgcccggcg ggttcaggat   4560
gctctggata tgcccgctgc tcgacagcac gaattcaacg ttgccgccaa acagttgcgc   4620
cgacttgtag caggacttcc acggggtgat gtggtcgttg gtgccggcca gggaaaagat   4680
gtcggccgtc acctgcttga ggtcgatggg ggtgccgcac acttccagtg cattcgggcg   4740
aatcagtggg ttatttttga acagttcgat caggtcgccg tggaacgccg cgggcaaccg   4800
tgtggtgtcg ttgttccaga acaggatgtc gaacaccggc ggttcgttgc ctagcaggta   4860
attgttgacc cagtagttcc agatcagatc gttggggcgc atccaggcga agaccttcgc   4920
catgtcgcgg ccttccagta cgccggcctg gtacgagtgg cgcttggcgg cttcaagggt   4980
ctgttcattg acgaacaggg caacatcgct gtcgagggtg gtatcaagca cgctcaccag   5040
caaggtcagg gcgttgacct tgttttcgcc aatcgccgcg taatggccca gcagcgcggt   5100
gcaagtgatg ccgccggagc aggcgccgag catgttcacg tctttgctgc cggtgatcgc   5160
ggtaacgaca tcaaccgctt ccttgagggc ttcgatgtag gtcgacaggc cccactctcg   5220
ctgttccttg gtgggatttc gccagctgac gatgaacgtt tgcacgttgt tgcgcaggca   5280
gaaccgcgcc aggctcttgt ccgggctcag gtcgaaaacg tagaacttgt tgatctgcgg   5340
cggcaccacc agcagcgggc gttcgtatac ctgctcggtg gtcggcttgt actggatcag   5400
ttccagcaca tcgttgcgaa acaccaccgc gccttcggtc acgcccaggc tcttgccgac   5460
ctcgaatgca cccatgttga cctggctcgg catgccgccg ttgtgtacca gatccttggc   5520
caggtgcgag aggccgtcga gcaggctttt gccaccggtt tcgaaaaagc gtttgactgc   5580
cgccgggttg gccgcggtgt tggtcggcgc catggcttcg gtcatgaggt tgatcacgaa   5640
gtgcccacgc gccacatcct tggggcgag gttactttca tcgatccagt cgtggagttc   5700
cttgcgccac gccaggtagg tttgcaaata acgtttatag agcgggttct ggctccaggc   5760
cggatcggcg aagcgacggt catcgctggt cggttgcagc ccggatttac ccagcagtac   5820
gttcttgagt tcaagaccaa agtgcgcgac atgtttgacg ctgtgcaccg gttgcttgat   5880
ggcctgccta agcaccattc gagcagaagc cagtagatcc tttccacgca gcccaacgac   5940
```

| | |
|---|---|
| aggattaagc cccaaggtgt tttcagaggc ttgatacttc aactcatcgt tactcttgtt | 6000 |
| actcatctag aacgctccat tgccctgaga cgagcacctt ggtcctgctg tgtagtcaca | 6060 |
| cagcaattgc caggtactac tgctcgggtg acctttgatt ctgcatcact gcttttttaa | 6120 |
| ttcagagagc actgcaggga ccttgccagt ccattggtta cccgagttta atttttttcg | 6180 |
| caagcgggcc aggcgtcgac cctgaagccg agcattcaaa cagatggaat tagaaaatgc | 6240 |
| cctctaaaga gcaagaggcg caggctagag catcagcttg acgacagatt cgttcgggtc | 6300 |
| gcgggttttt cctgcggctt ttagctcggc aagataatcg tcccaaagcg cgtcatgacg | 6360 |
| tcgccccagt tcgtagaggt attcccaggt gaacaggccg ctgtcgtggc catcgtcaaa | 6420 |
| ggtcagtttc agtgcgtact gaccggcggg ttctatcttg ctcagtccta cgttgatctt | 6480 |
| gccaaattgc aggatgggtt tgccgtggcc ctggacctcg gcggaaggat ccagctgaac | 6540 |
| ggtctggtta taggtacatt gagcaactga ctgaaatgcc tcaaaatgtt ctttacgatg | 6600 |
| ccattgggat atatcaacgg tggtatatcc agtgattttt ttctccatttt tagcttcctt | 6660 |
| agctcctgaa aatctcgata actcaaaaaa tacgcccggt agtgatctta tttcattatg | 6720 |
| gtgaaagttg gaacctctta cgtgccgatc aacgtctcat tttcgccaaa agttggccca | 6780 |
| gggcttcccg gtatcaacag ggacaccagg atttattttat tctgcgaagt gatcttccgt | 6840 |
| cacaggtatt tattcggcgc aaagggcctc gtgatacgcc tatttttata ggttaatgtc | 6900 |
| atgataataa tggtttctta gacgtcaggt ggcactttte ggggaaatgt gcgcggcccgc | 6960 |
| gttcctgctg gcgctgggcc tgtttctggc gctggacttc ccgctgttcc gtcagcagct | 7020 |
| tttcgcccac ggccttgatg atcgcggcgg ccttggcctg catatcccga ttcaacggcc | 7080 |
| ccagggcgtc cagaacgggc ttcaggcgct cccgaaggt | 7119 |

<210> SEQ ID NO 17
<211> LENGTH: 45
<212> TYPE: DNA
<213> ORGANISM: Artificial Sequence
<220> FEATURE:
<223> OTHER INFORMATION: PCR primer, YC2-N-f1

<400> SEQUENCE: 17
aataattcta gatgcgcgat aaacctgcga gggagtcact accca     45

<210> SEQ ID NO 18
<211> LENGTH: 41
<212> TYPE: DNA
<213> ORGANISM: Artificial Sequence
<220> FEATURE:
<223> OTHER INFORMATION: PCR primer, YC2-C-r1

<400> SEQUENCE: 18
atcatagagc tctcagcgca cgcgcacgta agtcccgggc g     41

<210> SEQ ID NO 19
<211> LENGTH: 7122
<212> TYPE: DNA
<213> ORGANISM: Artificial Sequence
<220> FEATURE:
<223> OTHER INFORMATION: phaC2 expression vector pBBR-phaC2

<400> SEQUENCE: 19

| | |
|---|---|
| ctcggtcggg ccgtctcttg ggcttgatcg gccttcttgc gcatctcacg cgctcctgcg | 60 |
| gcggcctgta gggcaggctc ataccctgc cgaaccgctt ttgtcagccg gtcggccacg | 120 |

```
gcttccggcg tctcaacgcg ctttgagatt cccagctttt cggccaatcc ctgcggtgca    180
taggcgcgtg gctcgaccgc ttgcgggctg atggtgacgt ggcccactgg tggccgctcc    240
agggcctcgt agaacgcctg aatgcgcgtg tgacgtgcct tgctgccctc gatgccccgt    300
tgcagcccta gatcggccac agcggccgca aacgtggtct ggtcgcgggt catctgcgct    360
ttgttgccga tgaactcctt ggccgacagc ctgccgtcct gcgtcagcgg caccacgaac    420
gcggtcatgt gcgggctggt ttcgtcacgg tggatgctgg ccgtcacgat gcgatccgcc    480
ccgtacttgt ccgccagcca cttgtgcgcc ttctcgaaga cgccgcctg ctgttcttgg     540
ctggccgact tccaccattc cgggctggcc gtcatgacgt actcgaccgc caacacagcg    600
tccttgcgcc gcttctctgg cagcaactcg cgcagtcggc ccatcgcttc atcggtgctg    660
ctggccgcc agtgctcgtt ctctggcgtc tgctggcgt cagcgttggg cgtctcgcgc      720
tcgcggtagg cgtgcttgag actggccgcc acgttgccca ttttcgccag cttcttgcat    780
cgcatgatcg cgtatgccgc catgcctgcc cctcccttt ggtgtccaac cggctcgacg     840
ggggcagcgc aaggcggtgc ctccggcggg ccactcaatg cttgagtata ctcactagac    900
tttgcttcgc aaagtcgtga ccgcctacgg cggctgcggc gccctacggg cttgctctcc    960
gggcttcgcc ctgcgcggtc gctgcgctcc cttgccagcc cgtggatatg tggacgatgg    1020
ccgcgagcgg ccaccggctg gctcgcttcg ctcggcccgt ggacaaccct gctggacaag    1080
ctgatggaca ggctgcgcct gcccacgagc ttgaccacag ggattgccca ccggctaccc    1140
agccttcgac cacatacccca ccggctccaa ctgcgcggcc tgcggccttg ccccatcaat   1200
tttttaatt ttctctgggg aaaagcctcc ggcctgcggc ctgcgcgctt cgcttgccgg     1260
ttggacacca agtggaaggc gggtcaaggc tcgcgcagcg accgcgcagc ggcttggcct    1320
tgacgcgcct ggaacgaccc aagcctatgc gagtgggggc agtcgaaggc gaagcccgcc    1380
cgcctgcccc ccgagacctg caggggggggg ggggcgctga ggtctgcctc gtgaagaagg    1440
tgttgctgac tcataccagg cctgaatcgc cccatcatcc agccagaaag tgagggagcc    1500
acggttgatg agagctttgt tgtaggtgga ccagttggtg attttgaact tttgctttgc    1560
cacggaacgg tctgcgttgt cgggaagatg cgtgatctga tccttcaact cagcaaaagt    1620
tcgatttatt caacaaagcc gccgtcccgt caagtcagcg taatgctctg ccagtgttac    1680
aaccaattaa ccaattctga ttagaaaaac tcatcgagca tcaaatgaaa ctgcaattta    1740
ttcatatcag gattatcaat accatatttt tgaaaagcc gtttctgtaa tgaaggagaa     1800
aactcaccga ggcagttcca taggatggca agatcctggt atcggtctgc gattccgact    1860
cgtccaacat caatacaacc tattaatttc ccctcgtcaa aaataaggtt atcaagtgag    1920
aaatcaccat gagtgacgac tgaatccggt gagaatggca aaagcttatg catttctttc    1980
cagacttgtt caacaggcca gccattacgc tcgtcatcaa aatcactcgc atcaaccaaa    2040
ccgttattca ttcgtgattg cgcctgagcg agacgaaata cgcgatcgct gttaaaagga    2100
caattacaaa caggaatcga atgcaaccgg cgcaggaaca ctgccagcgc atcaacaata    2160
ttttcacctg aatcaggata ttcttctaat acctggaatg ctgttttccc ggggatcgca    2220
gtggtgagta accatgcatc atcaggagta cggataaaat gcttgatggt cggaagaggc    2280
ataaattccg tcagccagtt tagtctgacc atctcatctg taacatcatt ggcaacgcta    2340
cctttgccat gtttcagaaa caactctggc gcatcgggct tcccatacaa tcgatagatt    2400
gtcgcacctg attgcccgac attatcgcga gcccatttat acccatataa atcagcatcc    2460
atgttggaat ttaatcgcgg cctcgagcaa gacgtttccc gttgaatatg gctcataaca    2520
```

```
cccccttgtat tactgtttat gtaagcagac agttttattg ttcatgatga tatattttta    2580
tcttgtgcaa tgtaacatca gagattttga dacacaacgt ggctttcccc ccccccctg      2640 caggtcccga gcctcacggc ggcgagtgcg ggggttccaa gggggcagcg ccaccttggg     2700
caaggccgaa ggccgcgcag tcgatcaaca agccccggag gggccacttt tgccggagg      2760 gggagccgcg ccgaaggcgt gggggaaccc cgcaggggtg cccttctttg gcaccaaag     2820 aactagatat agggcgaaat gcgaaagact taaaaatcaa caacttaaaa aagggggta     2880 cgcaacagct cattgcggca ccccccgcaa tagctcattg cgtaggttaa agaaaatctg     2940
taattgactg ccacttttac gcaacgcata attgttgtcg cgctgccgaa aagttgcagc    3000
tgattgcgca tggtgccgca accgtgcggc accctaccgc atggagataa gcatggccac    3060
gcagtccaga gaaatcggca ttcaagccaa gaacaagccc ggtcactggg tgcaaacgga    3120
acgcaaagcg catgaggcgt gggccgggct tattgcgagg aaacccacgg cggcaatgct    3180
gctgcatcac ctcgtggcgc agatgggcca ccagaacgcc gtggtggtca gccagaagac    3240
actttccaag ctcatcggac gttctttgcg gacggtccaa tacgcagtca aggacttggt    3300
ggccgagcgc tggatctccg tcgtgaagct caacggcccc ggcaccgtgt cggcctacgt    3360
ggtcaatgac cgcgtggcgt ggggccagcc ccgcgaccag ttgcgcctgt cggtgttcag    3420
tgccgccgtg gtggttgatc acgacgacca ggacgaatcg ctgttggggc atggcgacct    3480
gcgccgcatc ccgaccctgt atccgggcga gcagcaacta ccgaccggcc ccggcgagga    3540 gccgccagc cagcccggca ttccgggcat ggaaccagac ctgccagcct tgaccgaaac     3600
ggaggaatgg gaacggcgcg ggcagcagcg cctgccgatg cccgatgagc cgtgttttct    3660
ggacgatggc gagccgttgg agccgccgac acgggtcacg ctgccgcgcc ggtagcactt    3720
gggttgcgca gcaacccgta agtgcgctgt tccagactat cggctgtagc cgcctcgccg    3780
ccctatacct tgtctgcctc cccgcgttgc gtcgcggtgc atggagccgg ccacctcga    3840 cctgaatgga agccggcggc acctcgctaa cggattcacc gttttttatca ggctctggga   3900 ggcagaataa atgatcatat cgtcaattat tacctccacg gggagagcct gagcaaactg    3960
gcctcaggca tttgagaagc acacggtcac actgcttccg gtagtcaata aaccggtaaa   4020
ccagcaatag acataagcgg ctatttaacg accctgccct gaaccgacga ccgggtcgaa    4080
tttgctttcg aatttctgcc attcatccgc ttattatact tattcaggcg tagcaccagg   4140
cgtttaaggg caccaataac tgccttaaaa aaattacgcc ccgccctgcc actcatcgca    4200
gtactgttgt aattcattaa gcattctgcc gacatggaag ccatcacaga cggcatgatg    4260
aacctgaatc gccagcggca tcagcacctt gtcgccttgc gtataatatt tgcccatggt   4320
gagctctcag cgcacgcgca cgtaagtccc gggcgccgcc tccatcggtg gataattctg    4380
attgccgagg ccatgtgggg ttttttttg cgcgcccgag cgctcctgaa tccagcccag    4440
ccattgcgtc caccagctac cgtcgacggg cttggcgtcg tagtaccagg ccctggggtc    4500
gctgcttagt tttgcacctt cgaggtagtt ggctttcgga ttgttcggcg ggttgagaat    4560
gctctgcaca tgaccgctgt tggccaggac aaagcgacgc tcgccaccga gcaacagggt    4620
tgagcgatac accgcgtccc acggcgtgat gtgatcgttg atgccggcca cgctgaaact    4680
gtcgacggtg acctttgca agtcgatcgg ggtgccgcac acttccaggc cacccggatg     4740
gctcagcggg ttgtgcttga agaagtccag caagtcacca tgcagggcgg ccggcaggcg    4800
tgtgttgtca ttgttccagt agagaatgtc gaacgccggc ggctccttgc ccatcaggta    4860
```

```
attgttgacg aagtagctcc agatcaaatc gttggggcgc atccaggcga aaaccttggc    4920
catgtcgcgg ccttccagca cacctttctg gtaggagcgg cgcttggccg cctccagggt    4980
ctgttcgtcg gcgaagagtg tggccgggct gtccagttgg ctgtcgagca ggctcaccag    5040
gtacgtcgcg ctggagacgc ggcgcagctg tcgcttggct tgcaagtggc cctgcagggc    5100
agcaatggtc agcccgccag cgcaggcgcc catcaggttg acctcgcgcg cgccggtgat    5160
tgcccggcag acattcatgg cttcttccac cgcttcgacg taggtcgaca ggccccattc    5220
gcggtgacgt acatccggat tgcgccagct gatgacgaag gtttgcaggc cgttcttgag    5280
cgcgaactgg acgaagctgt tatgggggct gaggtcaaaa atgtagtact tgttgatctg    5340
tggcggcacc accagcagcg gtttggaata ctgcttttcg ctcatcggct tgtattggat    5400
cagctccagc agctcgttgc gaaacaccac ggcgccggtg gtggtggcga cggtcttgcc    5460
aacctcgaat gcatgcctgg tgacttgccg gggcaagcca tcgttgtgca agaggtcatc    5520
gaccagatgg ccgatcccgc gcaccaggct gttgccgccg gagttgaaga tttccttgat    5580
cgccagcgga ttgagcaggc tgttggacgg cgacacggca tcgttgagca gggcgaacgc    5640
gaagtgcgca cgggcgcggt catccgggct catgttgctt tcgtcgatcc agctcttgac    5700
ctgcttctgc cagctcaggt acgcctgcag gctgcgacga taaaagggat tgagactcca    5760
cgccggatcg tcgaagcgac ggtcttgcgg gttggtggga tgcagggtgt cgcccagcaa    5820
cacgcgtccc agttgaccac ccagtttcaa ggcgtgtcgc gcggtgtgca cggggtggcg    5880
caggccatgg gcggcgacac tgcgcaaagt cgaaaccaga tcccggccac gcaggccggt    5940
aatcgcactt tgtgcgttga tgaacttggc ggggtgggt agtgactccc tcgcaggttt    6000
atcgcgcatc tagaacgctc cattgccctg agacgagcac cttggtcctg ctgtgtagtc    6060
acacagcaat tgccaggtac tactgctcgg gtgacctttg attctgcatc actgcttttt    6120
taattcagag agcactgcag ggaccttgcc agtccattgg ttacccgagt ttaattttt    6180
tcgcaagcgg gccaggcgtc gaccctgaag ccgagcattc aaacagatgg aattagaaaa    6240
tgccctctaa agagcaagag gcgcaggcta gagcatcagc ttgacgacag attcgttcgg    6300
gtcgcgggtt tttcctgcgg ctttagctc ggcaagataa tcgtcccaaa gcgcgtcatg    6360
acgtcgcccc agttcgtaga ggtattccca ggtgaacagg ccgctgtcgt ggccatcgtc    6420
aaaggtcagt ttcagtgcgt actgaccggc gggttctatc ttgctcagtc ctacgttgat    6480
cttgccaaat tgcaggatgg gtttgccgtg ccctggacc tcggcggaag gatccagctg    6540
aacggtctgg ttataggtac attgagcaac tgactgaaat gcctcaaaat gttctttacg    6600
atgccattgg gatatatcaa cggtggtata tccagtgatt tttttctcca ttttagcttc    6660
cttagctcct gaaaatctcg ataactcaaa aaatacgccc ggtagtgatc ttatttcatt    6720
atggtgaaag ttggaacctc ttacgtgccg atcaacgtct cattttcgcc aaaagttggc    6780
ccagggcttc ccggtatcaa cagggacacc aggatttatt tattctgcga agtgatcttc    6840
cgtcacaggt atttattcgg cgcaaagggc ctcgtgatac gcctattttt ataggttaat    6900
gtcatgataa taatggtttc ttagacgtca ggtggcactt tcggggaaa tgtgcgcgcc    6960
cgcgttcctg ctggcgctgg gcctgtttct ggcgctggac ttcccgctgt tccgtcagca    7020
gcttttcgcc cacggccttg atgatcgcgg cggccttggc ctgcatatcc cgattcaacg    7080
gccccagggc gtccagaacg ggcttcaggc gctcccgaag gt    7122
```

<210> SEQ ID NO 20
<211> LENGTH: 254

```
<212> TYPE: DNA
<213> ORGANISM: Artificial Sequence
<220> FEATURE:
<223> OTHER INFORMATION: Partial sequence for phaC gene targeting

<400> SEQUENCE: 20
cgtggaaagg atctactggc ttctgctcga atggtgctta ggcaggccat caagcaaccg      60
gtgcacagcg tcaaacatgt cgcgcacttt ggtcttgaac tcaagaacgt actgctgggt     120
aaatccgggc tgcaaccgac cagcgatgac cgtcgcttcg ccgatccggc tggagccag     180 aacccgctct ataaacgtta tttgcaaacc tacctggcgt ggcgcaagga actccacgac     240
tggatcgatg aaag                                                       254

<210> SEQ ID NO 21
<211> LENGTH: 236
<212> TYPE: DNA
<213> ORGANISM: Artificial Sequence
<220> FEATURE:
<223> OTHER INFORMATION: Partial sequence for phaC gene targeting

<400> SEQUENCE: 21
gatgtggcgc gtgggcactt cgtgatcaac ctcatgaccg aagccatggc gccgaccaac      60
accgcggcca acccggcggc agtcaaacgc tttttcgaaa ccggtggcaa aagcctgctc     120
gacggcctct cgcacctggc caaggatctg gtacacaacg cggcatgcc gagccaggtc      180 aacatgggtg cattcgaggt cggcaagagc ctgggcgtga ccgaaggcgc ggtggt         236

<210> SEQ ID NO 22
<211> LENGTH: 239
<212> TYPE: DNA
<213> ORGANISM: Artificial Sequence
<220> FEATURE:
<223> OTHER INFORMATION: Partial sequence for phaC gene targeting

<400> SEQUENCE: 22
gattcgcccg aatgcactgg aagtgtgcgg caccccatc gacctcaagc aggtgacggc       60
cgacatcttt tccctggccg gcaccaacga ccacatcacc ccgtggaagt cctgctacaa     120
gtcggcgcaa ctgtttggcg gcaacgttga attcgtgctg tcgagcagcg gcatatcca     180 gagcatcctg aacccgccgg gcaatccgaa atcgcgctac atgaccagca ccgaagtgg      239

<210> SEQ ID NO 23
<211> LENGTH: 1272
<212> TYPE: DNA
<213> ORGANISM: Artificial Sequence
<220> FEATURE:
<223> OTHER INFORMATION: Partial sequence for phaC gene targeting

<400> SEQUENCE: 23
atcgtcgcag cctgcaggcg tacctgagct ggcagaagca ggtcaagagc tggatcgacg      60
aaagcaacat gagcccggat gaccgcgccc gtgcgcactt cgcgttcgcc ctgctcaacg     120
atgccgtgtc gccgtccaac agcctgctca atccgctggc gatcaaggaa atcttcaact     180
ccggcggcaa cagcctggtg gcgcgggatcg gccatctggt cgatgacctc ttgcacaacg     240
atggcttgcc ccggcaagtc accaggcatg cattcgaggt tggcaagacc gtcgccacca     300
ccaccggcgc cgtggtgttt cgcaacgagc tgctggagct gatccaatac aagccgatga     360
gcgaaaagca gtattccaaa ccgctgctgg tggtgccgcc acagatcaac aagtactaca     420
tttttgacct cagcccccat aacagcttcg tccagttcgc gctcaagaac ggcctgcaaa     480
```

```
ccttcgtcat cagctggcgc aatccggatg tacgtcaccg cgaatggggc ctgtcgacct      540
acgtcgaagc ggtggaagaa gccatgaatg tctgccgggc aatcaccggc gcgcgcgagg      600
tcaacctgat gggcgcctgc gctggcgggc tgaccattgc tgccctgcag ggccacttgc      660
aagccaagcg acagctgcgc cgcgtctcca gcgcgacgta cctggtgagc ctgctcgaca      720
gccaactgga cagcccggcc acactcttcg ccgacgaaca gacctggag gcggccaagc      780 gccgctccta ccagaaaggt gtgctggaag gccgcgacat ggccaaggtt ttcgcctgga      840
tgcgccccaa cgatttgatc tggagctact tcgtcaacaa ttacctgatg ggcaaggagc      900
cgccggcgtt cgacattctc tactggaaca atgacaacac acgcctgccg gccgccctgc      960
atggtgactt gctggacttc ttcaagcaca acccgctgag ccatccgggt ggcctggaag     1020
tgtgcggcac cccgatcgac ttgcaaaagg tcaccgtcga cagtttcagc gtggccggca     1080
tcaacgatca catcacgccg tgggacgcgg tgtatcgctc aaccctgttg ctcggtggcg     1140
agcgtcgctt tgtcctggcc aacagcggtc atgtgcagag cattctcaac ccgccgaaca     1200
atccgaaagc caactacctc gaaggtgcaa aactaagcag cgaccccagg gcctggtact     1260
acgacgccaa gc                                                         1272

<210> SEQ ID NO 24
<211> LENGTH: 357
<212> TYPE: DNA
<213> ORGANISM: Artificial Sequence
<220> FEATURE:
<223> OTHER INFORMATION: Partial sequence for phaC gene targeting

<400> SEQUENCE: 24
gcctgcgcca ccccgtgcac accgcgcgac acgccttgaa actgggtggt caactgggac       60
gcgtgttgct gggcgacacc ctgcatccca ccaacccgca agaccgtcgc ttcgacgatc      120
cggcgtggag tctcaatccc ttttatcgtc gcagcctgca ggcgtacctg agctggcaga      180
agcaggtcaa gagctggatc gacgaaagca acatgagccc ggatgaccgc gcccgtgcgc      240
acttcgcgtt cgccctgctc aacgatgccg tgtcgccgtc caacagcctg ctcaatccgc      300
tggcgatcaa ggaaatcttc aactccggcg gcaacagcct ggtgcgcggg atcggcc       357

<210> SEQ ID NO 25
<211> LENGTH: 348
<212> TYPE: DNA
<213> ORGANISM: Artificial Sequence
<220> FEATURE:
<223> OTHER INFORMATION: Partial sequence for phaC gene targeting

<400> SEQUENCE: 25
cacaacccgc tgagccatcc gggtggcctg gaagtgtgcg gcaccccgat cgacttgcaa       60
aaggtcaccg tcgacagttt cagcgtggcc ggcatcaacg atcacatcac gccgtgggac      120
gcggtgtatc gctcaaccct gttgctcggt ggcgagcgtc gctttgtcct ggccaacagc      180
ggtcatgtgc agagcattct caacccgccg aacaatccga aagccaacta cctcgaaggt      240
gcaaaactaa gcagcgaccc cagggcctgg tactacgacg ccaagcccgt cgacggtagc      300
tggtggacgc aatggctggg ctggattcag gagcgctcgg gcgcgcaa                   348
```

ISOGENIC STRAIN LINE OF BACTERIUM FOR PRODUCING POLYHYDROXYALKANOATE IN WHICH POLYHYDROXYALKANOATE SYNTHASE GENE IS DISRUPTED AND METHOD FOR PRODUCING POLYHYDROXYALKANOATE USING THE SAME

BACKGROUND OF THE INVENTION

1. Field of the Invention

The present invention relates to an isogenic strain line of a bacterium for producing polyhydroxyalkanoate in which a gene encoding polyhydroxyalkanoate synthase is disrupted; a gene targeting vector for disrupting a gene encoding polyhydroxyalkanoate synthase of a bacterium for producing polyhydroxyalkanoate; and a process for disrupting a gene encoding polyhydroxyalkanoate synthase of a bacterium for producing polyhydroxyalkanoate, using the aforementioned gene targeting vector. The present invention also relates to a method for producing polyhydroxyalkanoate comprising expressing a recombinant polyhydroxyalkanoate synthase in an isogenic strain line of a bacterium for producing polyhydroxyalkanoate in which a gene encoding polyhydroxyalkanoate synthase is disrupted.

2. Related Background Art

Until now, it has been reported that many microbes produce and accumulate in the body poly-3-hydroxy butyrate (PHB) or other poly-3-hydroxyalkanoate (PHA) ("Biodegradable plastic handbook", edited by the biodegradable plastic study group, NTS Inc. P178-197 (1995)). These polymers, like conventional plastics, can be used for producing various products by melt processing and the like. Furthermore, these polymers have an advantage of being completely degraded by microbes in the nature and do not cause pollution by remaining in the natural environment, unlike many conventional synthetic polymers, because they are biodegradable. They are also superior in biocompatibility, and would be expected to have applications as soft material for medical use and the like. Recently in particular, it is expected that unusual PHA in which substituent groups other than alkyl group are introduced in the side chain would be very useful considering expanding application of microbially produced PHA, for example an application as a functional polymer. Examples of such substituent groups include groups containing an aromatic ring (phenyl group, phenoxy group, benzoyl group and the like), unsaturated hydrocarbons, ester group, aryl group, cyano group, halogenated hydrocarbons, epoxides, thioethers and the like.

It has been known that microbially produced PHA can have various compositions and structures, depending upon the species of microbes for use in production thereof, the composition of the medium, the culture condition and the like. Various researches have been carried out on such PHA producing microbes, and the biosynthetic pathway of PHA has been relatively well investigated. Up until now, polyhydroxyalkanoate synthase is classified into three classes by substrate specificity and subunit composition.

Polyhydroxyalkanoate synthase which belongs to "the first class" is found in *Ralstonia eutropha*, *Aeromonas punctata* and the like and uses, as a substrate, thioester conjugate of 3-hydroxyalkanoate with short carbon chain length of C3-C5 and coenzyme CoA. Polyhydroxyalkanoate synthase in this class is composed of a single subunit of molecular weight 61-73 kDa.

Polyhydroxyalkanoate synthase which belongs to "the second class" is found in *Pseudomonas oleovolan* and *Pseudomonas aeruginosa* and uses, as a substrate, thioester conjugate of 3-hydroxyalkanoate with medium carbon chain length of C6-C14 and coenzyme CoA. Polyhydroxyalkanoate synthase in this class is composed of a single subunit of molecular weight 61-73 kDa, and in general there are two genes (phaC1 and phaC2) of Polyhydroxyalkanoate synthase, forming, together with the polyhydroxyalkanoate depolymerase gene (phaZ), a cluster of phaC1-phaZ-phaC2.

Polyhydroxyalkanoate synthase which belongs to "the third class" is found in *Allochromatium vinosum* and *Ectothiorhodospira shaposhnikovii* and the like, and the substrate specificity is similar to that of the first class polyhydroxyalkanoate synthase and uses thioester conjugate of 3-hydroxyalkanoate with short carbon chain length of C3-C5 and coenzyme CoA. Polyhydroxyalkanoate synthase that belongs to this class is composed of 2 different kinds of subunits of about 40 kDa.

Now, targeting the improvement of PHA productivity and the development of microbes capable of producing novel PHA, studies are carried out to modify polyhydroxyalkanoate synthase using the evolutionary engineering approach. In APPLIED AND ENVIRONMENTAL MICROBIOLOGY, 68,2411(2002), an evolutionary engineering modification was applied to the *Aeromonas caviae* derived polyhydroxyalkanoate synthase gene, which belonged to "the first class", and *Escherichia coli* was transformed with this gene together with the genes of (R)-specific enoyl-CoA hydratase (phaJ) and granuleassociated protein (ohaP), and the transformants were screened. As the result, it was disclosed that the productivity of PHA, which was composed of random copolymerization of 3-hydroxy butyric acid (PHB) and 3-hydroxyhexanoic acid, was improved and the unit ratio of 3-hydroxyhexanoic acid was increased. Also, in Applied Microbiology and Biotechnology, 59.477 (2002), random mutations were introduced to the *Aeromonas punctata* derived polyhydroxyalkanoate synthase gene, which belongs to "the first class", and *Escherichia coli* was transformed with this gene together with the genes of β-ketothiolase (phaA) and acetoacetyl-CoA reductase (phaB) derived from *Ralstonia eutropha*, and the transformants were screened. As the result, it was disclosed that mutated enzyme having a higher activity than wild type enzyme could be obtained, the weight average molecular weight could be increased, and intracellular accumulation of PHA could be increased.

Also, in The Journal of Biochemistry 133, 139 (2003), an evolutionary engineering modification was applied to the *Pseudomonas* sp. 61-3 derived polyhydroxyalkanoate synthase gene, which belonged to "the second class", and *Escherichia coli* was transformed with this gene together with the genes of β-ketothiolase (phaA) and acetoacetyl-CoA reductase (phaB) derived from *Ralstonia eutropha*, and the transformants were screened for PHB synthetic capability. As the result, it was disclosed that polyhydroxyalkanoate synthase which belonged to the second class could be modified to the synthase having the substrate specificity closed to that of the first class.

Non-Patent Document 1: "Biodegradable plastic handbook", edited by the biodegradable plastic study group, NTS Inc. P178-197 (1995)

Non-Patent Document 2: APPLIED AND ENVIRONMENTAL MICROBIOLOGY, 68, 2411 (2002)

Non-Patent Document 3: Applied Microbiology and Biotechnology, 59,477 (2002)

Non-Patent Document 4: The Journal of Biochemistry 133, 139 (2003)

SUMMARY OF THE INVENTION

To obtain PHA (in particular unusual PHA), which is expected to be a functional polymer, cheaply, and in large quantity stably, it is necessary to improve the productivity by increasing the activity of polyhydroxyalkanoate synthase of the microbe. To develop microbes capable of producing novel unusual PHA, it is also necessary to modify the substrate specificity of polyhydroxyalkanoate synthase of the microbe. Up until now, it is known that the majority of the microbes capable of producing unusual PHA contain the gene of polyhydroxyalkanoate synthase which belongs to the second class. Therefore, to achieve the objective described above, it is necessary that the gene of polyhydroxyalkanoate synthase, which belongs to the second class, is subjected to the evolutionary engineering modification. However, this is not done at this time because no host-vector system is constructed yet which is equipped with enzymes for substrate supply system for synthase belonging to the second class. Here, "substrate supply system for synthase belonging to the second class" is defined as an entire group of enzymes which catalyze biochemical conversions that the polymer materials undergo by a microbe, when the microbe capable of producing unusual PHA is cultured in the medium containing polymer materials (normally fatty acids with unusual substituents). The group of enzymes include the entire group or a part of the group consisting of acyl-CoA synthetase, acyl-CoA dehydrogenase, (L)-enoyl-CoA hydratase, 3-hydroxyacyl-CoA dehydrogenase, 3-ketoacyl-CoA thiolase, (R)-enoyl-CoA hydratase, 3-hydroxyacyl-CoA epimerase, ketoacyl-CoA reductase and the like.

A first object of the present invention is to provide an isogenic strain line of a bacterium for producing polyhydroxyalkanoate in which a gene encoding polyhydroxyalkanoate synthase is disrupted, wherein the bacterium for producing polyhydroxyalkanoate is a host having the aforementioned enzymes for substrate supply system which is useful for carrying out the evolutionary engineering modification of the polyhydroxyalkanoate synthase gene belonging to the second class. Further, in the past, Ralstonia eutropha PHB-4, Pseudomonas putida GPp104 (Japanese Patent Application Laid-Open No. 2001-008689), Pseudomonas cichorii YN2 ml (Japanese Patent Application Laid-Open No. 2003-011312) and the like have been known as the deletion strains of the polyhydroxyalkanoate synthase. To carry out the evolutionary engineering modification of polyhydroxyalkanoate synthase with an objective of improving the productivity of unusual PHA in particular, it is necessary to use an isogenic strain line of the microbial polyhydroxyalkanoate producer having the enzymes for substrate supply system that can utilize alkanes or alkanoic acids on which unusual substituents are introduced in the side chains. However, since the aforementioned conventional deletion strains of polyhydroxyalkanoate synthase are not necessarily equipped with such a substrate supply system, they cannot be utilized. The first object of the present invention is to provide, in particular, an isogenic strain line of a bacterium for producing polyhydroxyalkanoate Pseudomonas species YN21 strain in which a gene encoding polyhydroxyalkanoate synthase is disrupted. Pseudomonas species YN21 strain has been isolated by the present inventors as the strain having the enzymes of the substrate supply system with wide substrate specificity.

The general method for obtaining such a strain is to carry out screening the pool of randomly mutagenized bacteria, which requires tedious experimental manipulations, and thus a simpler method is desired to obtain a strain in which the polyhydroxyalkanoate synthase gene is disrupted. A second object of the present invention is to provide a simple process for obtaining an isogenic strain line of a bacterium for producing polyhydroxyalkanoate in which a polyhydroxyalkanoate synthase gene is disrupted.

Further, a third object of the present invention is to provide a method for producing polyhydroxyalkanoate by using a transformant, which is obtained by transforming an isogenic strain line of the bacterium for producing polyhydroxyalkanoate, in which a polyhydroxyalkanoate synthase gene is disrupted, with a recombinant polyhydroxyalkanoate synthase gene.

The present inventors have conducted extensive studies to isolate the PHA synthase gene from Pseudomonas species YN21 strain that is one of the unusual PHA producing microbes, and this lead to the discovery that the polyhydroxyalkanoate synthase genes (phaC1 and phaC2) of this strain and the polyhydroxyalkanoate depolymerase gene (phaZ) are forming a cluster of phaC1-phaZ-phaC2. Based on the result of the data base search on the homology of the base sequences of the phaC1 and phaC2 genes, a gene targeting vector was designed/constructed which by using DNAs with a base sequence specific to phaC1 and phaC2, can induce gene-disruption in phaC1 and phaC2 either separately or simultaneously.

By using the gene targeting vector thus constructed, an isogenic strain line of Pseudomonas sp. YN21 strain was newly obtained in which the gene encoding polyhydroxyalkanoate synthase was disrupted. Also, it was found that by using the gene targeting vector thus constructed, the polyhydroxyalkanoate synthase gene of the other polyhydroxyalkanoate producing bacteria containing polyhydroxyalkanoate synthase belonging to the second class was easily disrupted. Further, to complete the present invention, it was discovered that expressing a recombinant polyhydroxyalkanoate synthase in the strain, in which the polyhydroxyalkanoate synthase gene was disrupted, was useful to improve the productivity of polyhydroxyalkanoate relative to that of the wild type strain, and to synthesize PHA with a different composition from that of the wild type strain because of the difference in the substrate specificity of synthase.

According to the first aspect of the present invention, there if provided an isogenic strain line of a bacterium for producing polyhydroxyalkanoate in which a gene encoding polyhydroxyalkanoate synthase is disrupted.

According to the second aspect of the present invention, there if provided a method for producing polyhydroxyalkanoate, comprising culturing a recombinant transformant, obtained by transforming a recombinant polyhydroxyalkanoate synthase gene in the isogenic strain line of a bacterium for producing polyhydroxyalkanoate in which a gene encoding polyhydroxyalkanoate synthase is disrupted according to the first aspect of the present invention, and collecting polyhydroxyalkanoate from the culture broth.

According to the third aspect of the present invention, there is provided Pseudomonas sp. PC12 strain (FERM BP-08570) which is an isogenic strain line of Pseudomonas species YN21 strain (FERM BP-08569) and in which a gene encoding polyhydroxyalkanoate synthase is disrupted.

According to the fourth aspect of the present invention, there id provided a method for producing polyhydroxyalkanoate, comprising culturing a recombinant transformant, obtained by transforming a recombinant polyhydroxyalkanoate synthase gene in the isogenic strain line of a bacterium for producing polyhydroxyalkanoate in which a gene encoding polyhydroxyalkanoate synthase is disrupted according to the third aspect of the present invention, and collecting polyhydroxyalkanoate from the culture broth.

According to the fifth aspect of the present invention, there is provided a targeting vector for a polyhydroxyalkanoate synthase gene, comprising (1) a DNA selected from the group consisting of
(a) a DNA comprising a base sequence shown in SEQ ID NO: 1 or a part thereof and
(b) a DNA that hybridizes with a DNA consisting of a base sequence complementary to the DNA comprising a base sequence shown in SEQ ID NO: 1 under stringent conditions or a part thereof, and/or (2) a DNA for homologous recombination selected from the group consisting of (c) a DNA comprising a base sequence shown in SEQ ID NO: 2 or a part thereof and
(d) a DNA that hybridizes with a DNA consisting of a base sequence complementary to the DNA comprising a base sequence shown in SEQ ID NO: 2 under stringent conditions or a part thereof,
(3) a portion for disrupting a polyhydroxyalkanoate synthase gene, and
(4) a vector, wherein these materials of the above items (1) and/or (2), and (3) to (4) are operably linked.

According to the sixth aspect of the present invention, there is provided a host cell transformed by the gene targeting vector according to the fifth aspect of the present invention.

According to the seventh aspect of the present invention, there is provided a method for producing an isogenic strain of a bacterium for producing polyhydroxyalkanoate, wherein a homologous recombination of the gene targeting vector with a polyhydroxyalkanoate synthase gene in a chromosome of the bacterium for producing polyhydroxyalkanoate is caused by conjugal transfer between the host cell according to the sixth aspect of the present invention and the bacterium for producing polyhydroxyalkanoate so that the gene coding for the polyhydroxyalkanoate synthase is disrupted.

According to the eighth aspect of the present invention, there is provided a method for producing an isogenic strain of a bacterium for producing polyhydroxyalkanoate, wherein the gene coding for the polyhydroxyalkanoate synthase is disrupted by homologous recombination between a DNA coding for the targeting vector according to the fifth aspect of the present invention and the polyhydroxyalkanoate synthase gene on the chromosomal DNA of the bacterium for producing polyhydroxyalkanoate.

According to the ninth aspect of the present invention, there is provided a targeting vector for polyhydroxyalkanoate synthase gene directed to a bacterium for producing polyhydroxyalkanoate, comprising:
(1) a DNA selected from the group consisting of
(a) a DNA containing the base sequence shown in SEQ ID NO: 1 or a part thereof and
(b) a DNA hybridizing under stringent conditions with a DNA which is complementary to the DNA containing the base sequence shown in SEQ ID NO: 1 or a part thereof,
(2) A DNA selected from the group consisting of
(c) a DNA containing the base sequence shown in SEQ ID NO: 2 or a portion thereof and
(d) a DNA hybridizing under stringent conditions with a DNA which is complementary to the DNA containing the base sequence shown in SEQ ID NO: 2 or a portion thereof,
(2) a foreign DNA,
(3) a replication gene incompatible with the replication gene of the bacterium for producing polyhydroxyalkanoate,
(4) a conjugative transfer origin gene, and
(5) a vector,
wherein these materials of the above items (1) and/or (2), and (3) to (5) are operably linked.

The foreign DNA is preferably a gentamicin resistant gene or a kanamycin resistant gene.

According to the tenth aspect of the present invention, there is provided a host cell transformed by the gene targeting vector according to the ninth aspect of the present invention.

According to the eleventh aspect of the present invention, there is provided a method for producing an isogenic strain of a bacterium for producing polyhydroxyalkanoate, wherein a homologous recombination of the gene targeting vector with a polyhydroxyalkanoate synthase gene in a chromosome of the bacterium for producing polyhydroxyalkanoate is caused by conjugal transfer between the host cell according to the tenth aspect of the present invention and the bacterium for producing polyhydroxyalkanoate so that the gene coding for the polyhydroxyalkanoate synthase is disrupted.

According to the twelfth aspect of the present invention, there is provided a method for producing an isogenic strain of a bacterium for producing polyhydroxyalkanoate, wherein the gene coding for the polyhydroxyalkanoate synthase is disrupted by homologous recombination between a DNA coding for the targeting vector according to the ninth aspect of the present invention and the polyhydroxyalkanoate synthase gene on the chromosomal DNA of the bacterium for producing polyhydroxyalkanoate.

According to the thirteenth aspect of the present invention, there is provided a polyhydroxyalkanoate synthase gene targeting vector for a bacterium for producing polyhydroxyalkanoate, comprising:
(1) a DNA selected from the group consisting of
(a) a DNA containing the base sequence shown in SEQ ID NO: 1 or a portion thereof and
(b) a DNA hybridizing under stringent conditions with a DNA which is complementary to the DNA containing the base sequence shown in SEQ ID NO: 1 or a portion thereof,
(2) a DNA selected from the group consisting of
(c) a DNA containing the base sequence shown in SEQ ID NO: 2 or a portion thereof and
(d) a DNA hybridizing under stringent conditions with a DNA which is complementary to the DNA containing the base sequence shown in SEQ ID NO: 2 or a portion thereof,
(3) a replication gene incompatible with the replication gene of the bacterium for producing polyhydroxyalkanoate,
(4) a susceptibility gene,
(5) a conjugatibve transfer origin gene,
(6) a foreign DNA inserted between the DNA of the above item (1) and the DNA of the above item (2), and
(7) a vector,
wherein these materials of the above items (1) to (7) are operably linked.

The susceptibility gene is preferably a levansucrase gene.

Alternatively, the foreign DNA is preferably a gentamicin resistant gene or a kanamycin resistant gene.

According to the fourteenth aspect of the present invention, there is provided a host cell transformed by the gene targeting vector according to the thirteenth aspect of the present invention.

According to the fifteenth aspect of the present invention, there is provided a method for producing an isogenic strain of a bacterium for producing polyhydroxyalkanoate, wherein a homologous recombination of the gene targeting vector with a polyhydroxyalkanoate synthase gene in a chromosome of the bacterium for producing polyhydroxyalkanoate is caused by conjugal transfer between the host cell according to the fourteenth aspect of the present invention and the bacterium for producing polyhydroxyalkanoate so that the gene coding for the polyhydroxyalkanoate synthase is disrupted.

According to the sixteenth aspect of the present invention, there is provided a method for producing an isogenic strain of a bacterium for producing polyhydroxyalkanoate, wherein the gene coding for the polyhydroxyalkanoate synthase is disrupted by homologous recombination between a DNA coding for the targeting vector according to the thirteenth aspect of the present invention and the polyhydroxyalkanoate synthase gene on the chromosomal DNA of the bacterium for producing polyhydroxyalkanoate.

Since the isogenic strain line of the microbial polyhydroxyalkanoate producer of the present invention, in which a gene encoding polyhydroxyalkanoate synthase is disrupted, cannot synthesize polyhydroxyalkanoate because polyhydroxyalkanoate synthase is disrupted. However, having enzymes for the substrate supply system, the isogenic strain line can synthesize polyhydroxyalkanoate again by using this microbe as a host and transforming with the polyhydroxyalkanoate synthase gene using a suitable expression vector. At this time by changing appropriately the variety of the expression vector and the expression promoter, it is possible to control the amount and the timing of the expression of the synthase. Further, by transforming with polyhydroxyalkanoate synthase having different substrate specificity, it becomes possible to produce polyhydroxyalkanoate with a new composition. These are favorable properties for carrying out evolutionary engineering modification of polyhydroxyalkanoate synthase.

Further, the polyhydroxyalkanoate synthase gene targeting vector of the present invention can disrupt specifically not only polyhydroxyalkanoate synthase of Pseudomonas species YN21 strain but also other polyhydroxyalkanoate synthase of the polyhydroxyalkanoate producing bacteria containing polyhydroxyalkanoate synthase belonging to the second class, and thus this vector is useful.

Still further, since the method of the present invention for producing an isogenic strain line of the bacterium for producing polyhydroxyalkanoate, in which a gene encoding polyhydroxyalkanoate synthase is disrupted, can disrupt the gene encoding polyhydroxyalkanoate synthase selectively and with high efficiency by homologous recombination of the polyhydroxyalkanoate synthase gene on the chromosome of the bacterium for producing polyhydroxyalkanoate using the aforementioned gene targeting vector and produce expediently the isogenic strain line of the polyhydroxyalkanoate producing bacteria.

Even still further, the method of the present invention for producing polyhydroxyalkanoate makes it possible to change the amount of production of polyhydroxyalkanoate and composition of produced PHA by changing the amount of expression of polyhydroxyalkanoate synthase and/or the substrate specificity.

BRIEF DESCRIPTION OF THE DRAWINGS

FIG. 5 is the restriction map of plasmid pBBR-phaC2 constructed in Embodiment 4; and FIGS. 6A and 6B illustrate the methods of selective gene disruption by gene disruption by insetion and gene disruption by replacement.

DETAILED DESCRIPTION OF THE PREFERRED EMBODIMENTS

Figure 1:
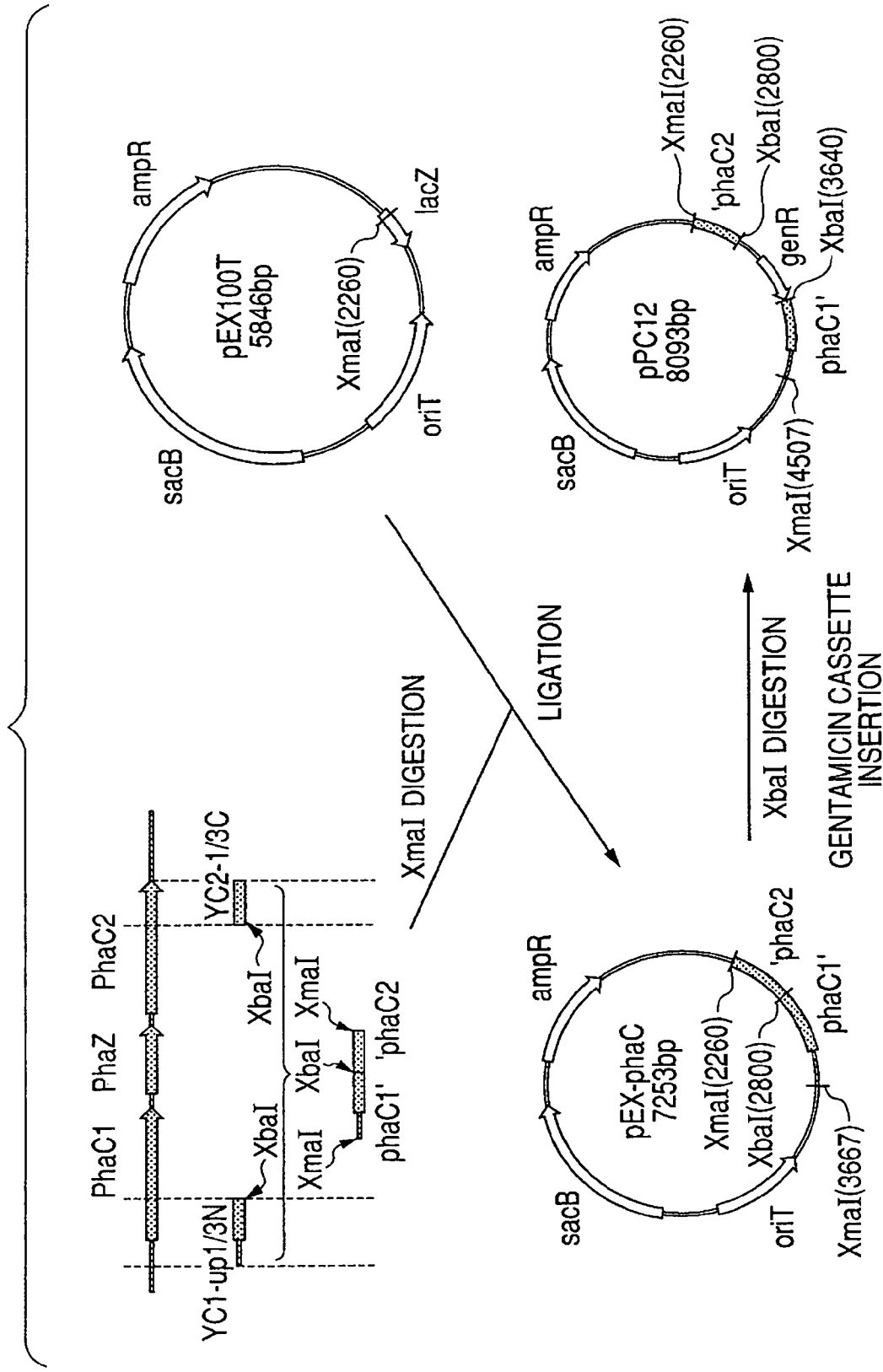
FIG. 1 illustrates the procedure for construction of the polyhydroxyalkanoate synthase gene targeting vector exemplified in Embodiment 1.

The bacterium for producing polyhydroxyalkanoate provided by the present invention is not particularly limited but can be, a microbial polyhydroxyalkanoate producer, among the microbes known to produce polyhydroxyalkanoate, containing the polyhydroxyalkanoate synthase gene on the chromosome which is homologous enough to phaC1' and phaC2', wherein phaC1' is an abbreviations of the DNA shown in (a) or (b) below or a part thereof, and phaC2' is an abbreviation of the DNA shown in (c) or (d) below or a part thereof:

(a) a DNA comprising a base sequence shown in SEQ ID NO: 1;

(b) a DNA that hybridizes with a DNA consisting of a base sequence complementary to the DNA comprising a base sequence shown in SEQ ID NO: 1 under stringent conditions, (c) a DNA comprising a base sequence shown in SEQ ID NO: 2;

(d) a DNA that hybridizes with a DNA consisting of a base sequence complementary to the DNA comprising the base sequence shown in SEQ ID NO: 2 under stringent conditions, so that both of phaC1' and phaC2' can undergo homologous recombination with the polyhydroxyalkanoate depolymerase gene under a physiological condition, that is in the microbe cells, and the polyhydroxyalkanoate synthase gene can be disrupted. Such microbes include *Pseudomonas oleovorans* (Makromol. Chem., 191, 1957-1965 (1990) and Macromolecules, 24, 5256-5260 (1991), *Pseudomonas putida* (Can. J. Microbiol., 41, 32-43 (1995) and Polymer International, 39, 205-213 (1996)), *Pseudomonas resinovorans* (Appl. Environ. Microbiol. 58 (2), 746 (1992)), *Pseudomonas* sp. 61-3 strain (Int. J. Biol. Macromol., 16 (3), 119 (1994)), *Pseudomonas cichorii* YN2 strain (FERM BP-7375), *Pseudomonas cichorii* H45 strain (FERM BP-7374), *Pseudomonas jessenii* P161 strain (FERM BP-7376) and the like, but not limited to these as long as it has the homology described above, and polyhydroxyalkanoate producing bacteria that will be discovered in the future may also be included in the present invention.

The present inventors searched a microbe capable of producing PHA containing 3-hydroxyphaenylvalerate monomer unit using phenyl valeric acid as a substrate. As a result, a microbial strain having the desired capability was successfully isolated from soil and designated as YN21 strain.

The search using the bacterial characteristics described below, based on Bergey's Manual of Systematic Bacteriology, Volume 1 (1984) and Bergey's Manual of Determinative Bacteriology, ninth edition (1994), revealed that YN21 strain belongs to the genus *Pseudomonas*. Thus, this strain was designated as *Pseudomonas* species YN21.

The microbe that the present inventors isolated from soil as a microbial producer of polyhydroxyalkanoate with unusual substituent groups, *Pseudomonas* sp. YN21, is believed to comprise substrate supply system enzymes for synthesizing polyhydoxyalkanoate from alkanoic acid having unusual substituents that is added to the medium, is useful for producing a host to carry out the evolutionary engineering modifications of polyhydroxyalkanoate synthase and is suitably provided especially for the present invention. The YN21 strain is deposited as the deposit No. "FERM BP-08569" in Patent Microorganism Depository Center, National Institute of Advanced Industrial Science and Technology, (Chuoh No. 6, 1-1 Higashi 1-chome, Tsukuba-City, Ibaragi-Prefecture). The bacterial characteristics of YN21 strain are listed below.

<The Bacterial Characteristics of YN21 Strain>
1) Morphological Characteristics
Size and shape: bacillus, 0.8 μm×1.5-2.0 μm
Polymorphism of cell: no
Motility: yes
Spore formation: no
Gram staining: −
Appearance of colony: round, smooth periphery, low convex, smooth surface, lustrous, semitransparent
2) Physiological Characteristics
Catalase activity: +
Oxidase activity: +
O/F test: oxidative
Nitrate reduction test: +
Indole production: −
Arginine dehydrolase: +
Esculin hydrolysis: −
Gelatin hydrolysis: −
Fluorescent dye production in King's B agar: +
Accumulation of poly-β-hydroxy butyric acid: −
Hydrolysis of Tween 80: +
Growth at 41° C.: −
Reduction of gluconic acid: −
Levan production: −
Putrefaction of potato: −
Tobacco hypersensitivity: −
Sucrose: −
Casein: −
Tyrosinase: +
Hydrogen sulfide: −
Pectin: −
Lecithinase: −
Litmus milk: B
Starch: −
3) Substrate utilization
Glucose: +
L-arabinose: +
D-mannose: +
D-mannitol: −
Maltose: −
Gluconic acid: +
D-xylose: (+)
Raffinose: −
Salicin: −
Glycerin: +
D-cellobiose: −
D-melezitose: −
Lactose: −
Galactose: +
D-sorbitol: −
α-methyl-D-glucoside: −
D-ribose: (+)
Sucrose: −
Inositol: −
D-fructose: +
L-rhamnose: −
D-arabinose: −
Dulcitol: −
Melibiose: −
Adonitol: −
Starch: −
Erythritol: −
Trehalose: −
Betaine: +
DL-lactic acid: +
D-tartaric acid: −
L-tartaric acid: (+)
Meso-tartaric acid: +
n-capric acid: +
L-malic acid: (+)
Citric acid: +
D-Saccharate: +
Levulinic acid: +
Mesaconic acid: −
Malonic acid: +
Succinic acid: +
Acetic acid: +
Propionic acid: +
n-butyric acid: +
Formic acid: −
Glutaric acid: +
D-quinic acid: +
Sebacic acid: +
p-hydroxybenzoic acid: +
Anthranilic acid: −
Pelargonic acid: +
Glyceric acid: +
γ-aminobutyric acid: +
L-leucine: +
L-serine: +
Histidine: +
L-isoleucine: +
L-arginine: +
β-alanine: +
L-tyrosine: +
L-valine: +
Homoserine: −
Sarcosine: +
Triacetin: +
Trigonelline: +
5-phenylvaleric acid: +
3-hydroxybutyric acid: +
L-asparagine: +

YN21 strain can be differentiated from an existing strain, Pseudomonas cichorii YN2 (FERM BP-7375), in physiological characteristics and substrate utilization such as nitrate reduction, indole production, glucose acidification, ariginine dehydrolase activity, D-mannose utilization and the like. Further, YN21 strain is different in characteristics from other existing strains: Pseudomonas cichorii H45 strain (FERM BP-7374) in nitrate reduction, arginine dehydrolase activity, L-arabinose utilization and D-mannitol utilization; Pseudomonas jessenii P161 strain (FERM BP-7376) in D-mannitol utilization; and Pseudomonas putida P91 strain (FERM BP-7373) in nitrate reduction, L-arabinose utilization, and D-mannose utilization.

The bacterium for producing polyhydroxyalkanoate of the present invention, in which a gene encoding polyhydroxyalkanoate synthase is disrupted, can be obtained by subjecting a bacterium for producing polyhydroxyalkanoate to: a mutagenic treatment resulting in change in the base sequence of the gene encoding polyhydroxyalkanoate synthase; integration of a transposon to the base sequence of the gene encoding the enzyme; and a change by the genetic engineering so that the gene encoding the enzyme is not expressed, for example antisense gene inhibition; and also selective gene disruption.

Chemical mutagens useful for inducing mutation include alkylating agents, for example, N-methyl-N'-nitro-N-nitrosoguanidine (NTG), ethyl methanesulfonate (EMS), diethyl sulfate (DES) and the like. Chemicals, which deaminate DNA bases, such as hydroxylamine and nitrite, are also useful. Ionizing radiation (γ- and X-ray) and ultraviolet (UV) irradiation are physical mutagens useful for inducing mutations.

To obtain a strain, in which the polyhydroxyalkanoate synthase gene is disrupted, from a randomly mutagenized strain, following steps may be carried out. The mutagenized strain is cultured on agar plates containing alkanoic acid which can be used as a constituent unit of PHA, and the intracellular PHA is fluorescently strained with Nile red or the like to primarily screen the bacteria incapable of synthesizing PHA. Next, the clones thus obtained were homogenized, and by measuring the polyhydroxyalkanoate synthase activity in the homogenates, the strains, in which the polyhydroxyalkanoate synthase gene is disrupted, are obtained. The polyhydroxyalkanoate synthase activity may be estimated, for example, by mixing thioester conjugate of 3-hydroxyalkanoic acid and CoA, which can be a substrate of polyhydroxyalkanoate synthase, with an enzyme solution containing polyhydroxyalkanoate synthase and by measuring the rate of dissociation of CoA by a publicly known method.

To obtain an isogenic strain line of a bacterium for producing polyhydroxyalkanoate, in which a gene encoding polyhydroxyalkanoate synthase is disrupted by a selective gene disruption method, the homologous recombination using a linear DNA may be used. However, the isogenic strain line of the bacterium for producing polyhydroxyalkanoate, in which the gene is disrupted, can be obtained with less damage to the bacteria and with better efficiency by using, in particular, the vector targeting the polyhydroxyalkanoate synthase gene, which is disclosed as one of the invention related to the present application.

In general, the selective gene disruption method to the target site on the chromosome by homologous recombination is used for studying the function of the gene and for selective disruption of the gene which is involved in undesired characteristics for growing microbes for practical use. The two disruption method, the gene insertion disruption method and the gene replacement disruption method, have been used (FIGS. 6A and 6B). These methods are based on a basic principle that an external desired gene included in the DNA of the external target gene is integrated into the target DNA sequence of the endogenous genomic DNA by artificially inducing genetic homologous recombination, which could occur naturally in the living body of organisms, between the endogenous genomic DNA present in a chromosome of the organism and external targeting DNA (targeting vector).

The gene targeting vector herein means a DNA construct used for disrupting by homologous recombination the gene coding for the target DNA (polyhydroxyalkanoate synthase) in the endogenous genomic DNA of the bacterium for producing polyhydroxyalkanoate. Here, "disrupting gene" means the change in DNA sequence described below introduced into a part of the endogenous genome by homologous recombination between the targeting DNA and the endogenous genomic DNA.

(1) A deletion of a part of the DNA sequence of the target DNA
(2) A replacement of a part of the DNA sequence of the target DNA with an foreign DNA
(3) An insertion of an foreign DNA into the DNA sequence of the target DNA The change in the DNA sequence achieved by the gene insertion disruption method is the change by the (3). The change in the DNA sequence achieved by the gene replacement disruption method is the change by the (1), (2) or (3). By these changes, the gene encoding polyhydroxyalkanoate synthase in the endogenous genomic DNA of the bacterium for producing polyhydroxyalkanoate practically loses the function, and transcription/translation of the polyhydroxyalkanoate synthase gene or biosynthesis of polyhydroxyalknoate synthase protein with activity can be prevented.

Since there are two genes of polyhydroxyalkanoate synthase (phaC1 and phaC2) forming a cluster of phaC1-phaZ-phaC2 with the polyhydroxyalkanoate depolymerase gene (phaZ), the isogenic strain line of the bacterium for producing polyhydroxyalkanoate of the present invention, in which the gene coding the polyhydroxyalkanoate synthase is disrupted, may be produced with either of the aforementioned gene insertion disruption method and gene replacement disruption method by disrupting phaC1 and phaC2 individually, but only the aforementioned gene replacement disruption method, but not the aforementioned gene insertion disruption method, can be used to disrupt phaC1 and phaC2 at the same time.

Targeting vectors with different basic structures described below used herein to disrupt the polyhydroxyalkanoate synthase gene, are selected according to whether the disruption is carried out by the gene insertion disruption method or the gene replacement disruption method, and also whether phaC1 and phaC2 are disrupted individually or both at the same time.

The polyhydroxyalkanoate synthase gene targeting vector with the following basic structure of (I) or (III) is used to disrupt phaC1 and phaC2 at the same time by the gene replacement disruption method. That is, (I) a gene targeting vector including:
a DNA shown by the following (a) or (b) for homologous recombination or a part thereof:
(a) a DNA comprising a base sequence shown in SEQ ID NO: 1, or
(b) a DNA that hybridizes with a DNA consisting of a base sequence complementary to the DNA comprising a base sequence shown in SEQ ID NO: 1 under stringent conditions,
and a DNA shown by the following (c) or (d) or a part thereof:
(c) a DNA comprising a base sequence shown in SEQ ID NO: 2;
(d) a DNA that hybridizes with a DNA consisting of a base sequence complementary to the DNA comprising a base sequence shown in SEQ ID NO: 2 under stringent conditions,
a region for disrupting the desired gene;
and vector, wherein these are functionally linked with each other to form a basic structure.

(III) a gene targeting vector including:
a DNA shown by the following (a) or (b) or a part thereof:
(a) a DNA comprising a base sequence shown in SEQ ID NO: 1, or
(b) a DNA that hybridizes with a DNA consisting of a base sequence complementary to the DNA comprising a base sequence shown in SEQ ID NO: 1 under stringent conditions,
and a DNA shown by the following (c) or (d) or a part thereof:
(c) a DNA comprising a base sequence shown in SEQ ID NO: 2, or
(d) a DNA that hybridizes with a DNA consisting of a base sequence complementary to the DNA comprising a base sequence shown in SEQ ID NO: 2 under stringent conditions, wherein a desired foreign DNA that is exogenous to the endogenous genomic DNA of the bacterium for producing polyhydroxyalkanoate is inserted between "the DNA shown in (a) or (b) or a part thereof" and "the DNA shown in (c) or (d) or a part thereof" forming a basic structure.

The gene targeting vector with the following basic structure of (I'), (II') or (III') is used as the polyhydroxyalkanoate synthase gene targeting vector to disrupt phaC1 and phaC2 individually by the gene replacement disruption method.

That is, (I') a gene targeting vector including: a DNA shown by the following in (a) or (b) or a part thereof for homologous recombination:
(a) a DNA comprising a base sequence shown in SEQ ID NO: 1, or
(b) a DNA that hybridizes with a DNA consisting of a base sequence complementary to the DNA comprising a base sequence shown in SEQ ID NO: 1 under stringent conditions,
a region for disrupting the desired gene; and a vector, wherein these are functionally linked with each other to form a basic structure.

(I") a gene targeting vector including: DNA shown in (c) or (d) below or a part thereof for homologous recombination:
(c) a DNA comprising a base sequence shown in SEQ ID NO: 2, or
(d) a DNA that hybridizes with a DNA consisting of a base sequence complementary to the DNA comprising a base sequence shown in SEQ ID NO: 2 under stringent conditions,
a region for disrupting the desired gene; and a vector, wherein these are functionally linked with each other to form a basic structure.

(III') a gene targeting vector including DNA shown in (a) or (b) below or a part thereof:
(a) a DNA comprising a base sequence shown in SEQ ID NO: 1, or
(b) a DNA that hybridizes with a DNA consisting of a base sequence complementary to the DNA comprising a base sequence shown in SEQ ID NO: 1 under stringent conditions,
wherein a desired foreign DNA that is exogenous to the endogenous genomic DNA of the bacterium for producing polyhydroxyalkanoate is inserted in a part of "the DNA shown in (a) or (b) or a part thereof" forming a basic structure.

(III") a gene targeting vector including a DNA shown by the following (c) or (d) below or a part thereof:
(c) a DNA comprises a base sequence shown in SEQ ID NO: 2, or
(d) a DNA that hybridizes with the DNA consisting of a base sequence complementary to the DNA comprising a base sequence shown in SEQ ID NO: 2 under stringent conditions,
wherein a desired foreign DNA that is exogenous to the endogenous genomic DNA of the bacterium for producing polyhydroxyalkanoate is inserted in a part of "the DNA shown in (c) or (d) or a part thereof" forming a basic structure.

The gene targeting vector with the following basic structure of (I'), (I"), (II) or (II') is used as the polyhydroxyalkanoate synthase gene targeting vector to disrupt phaC1 and phaC2 individually by the gene insertion disruption method.

That is, (I') a gene targeting vector including a DNA shown by the following (a) or (b) or a part thereof for homologous recombination;
(a) a DNA comprising a base sequence shown in SEQ ID NO: 1, or
(b) a DNA that hybridizes with a DNA consisting of a base sequence complementary to the DNA comprising a base sequence shown in SEQ ID NO: 1 under stringent conditions,
a region for disrupting the desired gene; and a vector, wherein these are functionally linked with each other to form a basic structure.

(I") a gene targeting vector including a DNA shown by the following (c) or (d) or a part thereof for homologous recombination:
(c) a DNA comprising a base sequence shown in SEQ ID NO: 2, or
(d) a DNA that hybridizes with a DNA consisting of a base sequence complementary to the DNA comprising a base sequence shown in SEQ ID NO: 2 under stringent conditions,
a region for disrupting the desired gene; and a vector, wherein these are functionally linked with each other to form a basic structure.

(II) a gene targeting vector including a DNA shown by the following (a) or (b) or a part thereof:
(a) a DNA comprising a base sequence shown in SEQ ID NO: 1;
(b) a DNA that hybridizes with a DNA consisting of a base sequence complementary to the DNA comprising a base sequence shown in SEQ ID NO: 1 under stringent conditions,
and a desired foreign DNA that is exogenous to the endogenous genomic DNA.

(II') a gene targeting vector including a DNA shown by the following (c) or (d) or a part thereof:
(c) a DNA comprising a base sequence shown in SEQ ID NO: 2, or
(d) a DNA that hybridizes with a DNA consisting of a base sequence complementary to the DNA comprising a base sequence shown in SEQ ID NO: 2 under stringent conditions, and a desired foreign DNA that is exogenous to the endogenous genomic DNA.

Here, in the basic structure (I), (I'), (I"), (II), (II'), (III), (III') and (III") the DNA that "hybridizes under stringent conditions" is the DNA described below. That is, it is the DNA (1) which forms a DNA-DNA hybrid with the DNA comprising the base sequence shown in SEQ ID NO: 1 or 2 under a high ionic concentration [including, for example, 6×SSC (900 mM of sodium chloride, 90 mM sodium citrate) and the like] and at the temperature of 65° C. and (2) in which the hybrid is maintained after washing under a low ionic concentration [including, for example, 0.1×SSC (15 mM of sodium chloride, 1.5 mM of sodium citrate) and the like] and at the temperature of 65° C. for 30 min. In particular, for example, included are DNAs which have the base sequence shown in SEQ ID NO: 1 or 2, in which a part is deleted, replaced or added to the extent that the disrupting function to the desired gene is not impaired. Such DNA may be natural cloned DNA, natural cloned DNA with artificially introduced base deletion, replacement or addition, or artificially synthesized DNA. Further, in the basic structure (I), (I'), (I"), (II), (II'), (III), (III') and (III"), "DNA shown as (a) or (b), or a part thereof" or "DNA shown as (c) or (d), or a part thereof" are not necessary to encode a protein having polyhydroxyalkanoate synthase activity but may have enough homology so that it can perform homologous recombination with the polyhydroxyalkanoate synthase gene on the chromosome under the physiological condition, that is in the cell of the microbe, and by this recombination the polyhydroxyalkanoate synthase gene is disrupted. Such homology may be preferably 90% or above, and more preferably 95% or above. Still further, if the DNA, which is used for producing a strain of the microbe in which polyhydroxyalkanoate synthase gene is disrupted, is large enough so that the DNA can undergo homologous recombination with the polyhydroxyalkanoate synthase gene on the chromosome and disrupt the same by doing so, the DNA may be a part of the DNA of the present invention. Here, a part means that the length is preferably 50 bases or longer, or more preferably 100 base or longer while keeping the capability of disrupting the desired gene.

Particular examples of "a part" of DNA shown in (a) or (b) that is placed in the gene targeting vector include SEQ ID NO: 20, SEQ ID NO: 21, SEQ ID NO: 22, SEQ ID NO: 23, SEQ ID NO: 24 and SEQ ID NO: 25.

The vector in the basic structure (I) is not particularly limited, and general vectors with wide host range may be used and include, for example, pJRD215 (Davidson et al., Gene, 51, 275-280 (1987)) and pBBR1MCS series (Kovach et al., Gene, 166, 175-176 (1995)) and the like.

In the gene targeting vectors of the basic structure (I), (III), the "DNA shown in (a) or (b) or a part thereof" and "DNA shown in (c) or (d) or a part thereof" must be integrated into a mobile vector in the same direction. When the length of the "DNA shown in (a) or (b), or a part thereof" is assumed to be 1, the length of the "DNA shown in (c) or (d), or a part thereof" that is integrated into the targeting vector is from 0.4 to 2.5, preferably from 0.5 to 2, more preferably from 0.8 to 1.25. The large difference of this number is not preferable because the yield of double homologous recombinants would be lower.

The "foreign DNA" in the basic structure (II), (II'), (III), (III') and (III") includes, for example, the marker gene, the reporter gene, the gene amplifying gene, the gene expression control DNA sequence, which can add characteristics that lead to a substantial functional disruption of the polyhydroxyalkanoate synthase gene by introducing deletion, replacement or insertion to the target DNA sequence in the endogenous genomic DNA, or DNA comprising one or more of these. Here, the "marker gene" includes any of the marker genes which are used normally in the art of the genetic engineering field. Examples include the resistant genes to antibiotics such as tetracycline, ampicillin, gentamicin or kanamycin. Further, examples of the "reporter gene" include the genes of luciferase, green fluorescent protein (GFP), β-lactamase and the like. Still further, examples of the "gene amplifying gene" include a DNA sequence containing desired primer binding sequences by which a specific gene amplification product of the disrupted strain can be obtained by the PCR method using the chromosome DNA as a template.

The foreign DNAs used in (II) and (II'), or (III') and (III") are preferably different.

In the gene targeting vector of the basic structure (III'), the site of insertion of the foreign DNA to the "DNA shown in (a) or (b) or a part thereof" is at between 1-9, preferably 2-8 and more preferably 4-6, when the length of the "DNA shown in (a) or (b) or a part thereof", which is integrated to this vector, is assumed to be 10. When the site of insertion of the foreign DNA is biased to one end of the DNA shown in (a) or (b), or a part thereof, the yield of double homologous recombinants is lowered, and thus this is not preferable.

In the gene targeting vector of the basic structure (III"), the site of insertion of the foreign DNA to the "DNA shown in (c) or (d) or a part thereof" is at between 1-9, preferably 2-8 and more preferably 4-6, when the length of the "DNA shown in (c) or (d) or a part thereof", which is integrated to this vector, is assumed to be 10. When the site of insertion of the foreign DNA is biased to one end of the DNA shown in (c) or (d), or a part thereof, the yield of double homologous recombinants is lowered, and thus this is not preferable.

When the Mob site containing the origin of conjugal transfer gene (OriT) is introduced to the gene targeting vector of the basic structure (II), (II'), (III), (III') and (III"), and *Escherichia coli* mobilizer strain, for example, S17-1 strain (ATCC 47055) is transformed by the vector and used as a plasmid supplying bacteria, the vector is introduced into the bacterium for producing polyhydroxyalkanoate more efficiently with less damage thereto and thus it is possible to obtain more easily and more efficiently the strains, in which the polyhydroxyalkanoate synthase gene is disrupted, and thus this method is more favorable. This is because, since *E. coli* mobilizer strain contains the tra gene, the mob$^+$, tra$^-$ gene targeting vector can be conjugatively transferred without the help of the helper plasmid (R. Simon et al. (1983) Bio-Technology 1: 784).

It is preferable for the gene targeting vector of the basic structure (III), (III') and (III") to contain a gene which leads plasmid recipient bacteria to death (susceptibility gene) under a certain condition. As a susceptibility gene, for example, the levansucrase (sacB) gene derived from *Baccilus subtilis* can be suitably used in the present invention, because many gram-negative bacteria with this gene are killed in the medium containing sucrose at 5 wt % or more (Gay et al. J. Bacteriol. 164, 918), and the present inventors have also confirmed that the gene functions in *Pseudomonas* species YN21 strain.

To construct the gene targeting vector of the basic structure (I), (I'), (I"), (II), (II'), (III), (III') and (III"), each DNA that is a composing element of the aforementioned basic structure may be integrated into the vector using normal technique of molecular biology. However, to construct in particular the gene targeting vector of the basic structure (II), (II'), (III), (III') and (III"), the utilization of a mobile vector, which contains a replication gene that is incompatible with the replication gene of the bacterium for producing polyhydroxyalkanoate, the origin of conjugative gene and susceptibility gene, would be useful because the polyhydroxyalkanoate synthase gene targeting vector of the present invention can be produced with fewer steps. Such mobile vectors include, for example, pEX100T (ATCC 87436), pJQ200 (ATCC 77482), pDMS197 (ATCC 87694), pRE107 (ATCC 87691) and the like and can be used suitably for construction of the polyhydroxyalkanoate synthase gene targeting vector of the present invention.

For example, to construct the gene targeting vector of the basic structure (III), the "DNA shown in aforementioned (a) or (b), or a part thereof", the "DNA shown in aforementioned (c) or (d), or a part thereof" and the selection marker may be integrated to the aforementioned mobile vector. There is no restriction in the order of integration for these but for example, the aforementioned mobile vector is treated with an appropriate restriction enzyme, and a DNA fragment thus obtained is mixed with the DNA shown in aforementioned (a) or (b) or a part thereof and the mixture is treated with DNA ligase. Next, a part of the vector or the DNA shown in aforementioned (a) or (b) or a part thereof integrated into the vector are cleaved by the treatment of a restriction enzyme that recognize the different site from the aforementioned restriction enzyme. The vector DNA fragment thus obtained is mixed with a DNA fragment that contains the aforementioned selection marker and is treated with DNA ligase to insert the selection marker to the vector. Further, in the steps of the construction, treatments known in the arts may be performed, such as addition of linkers, formation of blunt ends and the like as needed.

To disrupt the polyhydroxyalkanoate synthase gene of the bacterium for producing polyhydroxyalkanoate using the gene targeting vector of the basic structure (I), (I') or (I"), these gene targeting vectors are introduced into the bacterium for producing polyhydroxyalkanoate. The method for introducing the gene targeting vector can be appropriately selected from the well known methods to a person skilled in the arts such as contacting to competent cells, electroporation and the like.

Next, the first screening is carried out using characteristics, for example, incapable of growing on an agar plate containing a fatty acid as an only carbon source, and then the disruption of the polyhydroxyalkanoate synthase gene is confirmed on the clones thus obtained.

Disruption of the polyhydroxyalkanoate synthase gene of the bacterium for producing polyhydroxyalkanoate using the gene targeting vector of the basic structure (II), (II'), (III), (III') and (III") may be carried out in the same manner as the case of the gene targeting vector of the basic structure (I), (I') or (I"). First the aforementioned mobilizer strain of E. coli is transformed by this gene targeting vector. Next, the gene targeting vector is transferred into the bacterium for producing polyhydroxyalkanoate by using conjugal transfer between the transformed mobilizer E. coli and the bacterium for producing polyhydroxyalkanoate.

By selecting with the aforementioned selection marker, the strain may be obtained in which the polyhydroxyalkanoate synthase gene is disrupted as a result of homologous recombination between the gene targeting vector and the chromosome DNA. Further, since there are 2 homologous regions at the front and the end of the aforementioned selection marker in the chromosome of the host bacterium for producing polyhydroxyalkanoate and in the gene targeting vector, most of the homologous recombinants obtained at this stage are two kinds with structures having the sequence derived from the gene targeting vector inserted at the different site, and it is believed that the ratio is very low of the homologous recombinants having the crossing at the both of two homologous regions at the front and the end of the selection marker at the same time. However, the polyhydroxyalkanoate synthase gene is disrupted by the sequence derived from the gene targeting vector being inserted.

Next, in the case where the gene targeting vector of the basic structure (III), (III') or (III") is used, the selection based on the function of the susceptibility gene is carried out. By this selection, a variant strain may be obtained in which, among the sequences inserted into the chromosome of the recombinants selected by the aforementioned selection marker from the plasmid recipient bacteria, the mobile vector part derived from the gene targeting vector is deleted. This is achieved by the homologous recombination at the other homologous region which was not used at the homologous recombination of the previous step. Thus, at this step the two kinds of recombinants having different chromosomal structures at the previous step becomes the recombinant having the same chromosomal structure (the polyhydroxyalkanoate synthase gene is split by the selection marker).

Disruption of the polyhydroxyalkanoate synthase gene in the recombinants obtained using the targeting vector of the present invention for the polyhydroxyalkanoate synthase gene may be confirmed by the following methods: by determining the loss of polyhydroxyalkanoate synthase activity in the recombinant by the method described above; by Southern hybridization after digesting the chromosome DNA of the recombinant with a restriction enzyme; or by the PCR method using the chromosome DNA template and appropriate primers.

Since the targeting vector for polyhydroxyalkanoate synthase gene of the present invention replicates and amplifies autonomously in an appropriate host cells, copies of this vector can be produced by culturing the transformant which is obtained by introducing this vector to host cells and performing transformation. Such host cells that may be used without distinction include gram positive or gram negative bacteria, higher or lower cells, animal or plant cells, as long as the cell can be transformed by the targeting vector for polyhydroxyalkanoate synthase gene, and the vector can be stably maintained and replicate in the cell. To introduce the polyhydroxyalkanoate synthase gene targeting vector to the host cells, the method can be selected appropriately from those well known to a person skilled in the arts, such as contacting the polyhydroxyalkanoate synthase gene targeting vector to competent cells, electropopration and the like.

In the isogenic strain line of the bacterium for producing polyhydroxyalkanoate in which a gene encoding polyhydroxyalkanoate synthase is disrupted, the gene expression vector for expressing recombinant polyhydroxyalkanoate synthase is not limited as long as the vector can autonomously replicate in the cells of this isogenic strain line and express functional polyhydroxyalkanoate synthase. For example, the vector may include wide host range vectors such as pJRD215 (Davidson et al., Gene, 51, 275-280 (1987), ATCC 37533) and pBBR1MCS series (Kovach et al., Gene, 166, 175-176 (1995)), pBHR1, pLA2917 (ATCC 37355) and the like.

Cloning of polyhydroxyalkanoate synthase to these vectors may be carried out by conventional methods using a promoter, a ribosomal binding site, a DNA fragment containing the polyhydroxyalkanoate synthase gene and a transcription termination sequence.

Any promoter may be used as long as it is capable of expressing in the host, and for example, promoters derived from E. coli or phage, such as trp promoter, tac promoter, lac promoter, lpp promoter, tufB promoter, recA promoter, PL promoter, PR promoter, T7 promoter and the like, and promoters with constant and high expression such as ribosomal RNA promoter (rRP) and the like may be used. The method of introducing recombinant DNA to bacteria includes, for example, the method using calcium ion (Current Protocols in Molecular Biology, Vol 1, pp 1.8.1 1994) an the electroporation method (Current Protocols in Molecular Biology, Vol 1, pp 1.8.4 1994).

The medium containing needed components for growth of the transformant used is selected appropriately for normal culturing of the polyhydroxyalkanoate synthase gene disrupted strain transformed by the recombinant polyhydroxyalkanoate synthase gene used for the PHA production method of the present invention. Normal culturing includes, for example, preparing storage bacteria, growing bacteria to obtain the number required for PHA production and to maintain the active condition needed for PHA production and the like. For example, any kind of media may be used, such as general natural media (meat broth media, yeast extract and the like) and synthetic media supplemented with nutrient source, as long as they do not have bad effects on the growth and survival of the transformant.

Any culture method, such as liquid culture, solid culture and the like may be used as long as the transformant grows and PHA is produced. Further, batch culture, fed batch culture, semi-continuous culture, continuous culture and the like may be used without distinction. In liquid batch culture style, oxygen is supplied by shaking flask method and by mixed aeration method by a jar fermentor. Also, a multiple steps procedure may be adopted by connecting a multiplicity of these steps.

The composition and structure of PHA, in particular variety of unusual PHA having substituent groups in the side chain, that is produced by the strain in which the polyhydroxyalkanoate synthase gene is disrupted and which is transformed by the recombinant polyhydroxyalkanoate synthase gene, is determined by the nature of the isogenic strain line in which the polyhydroxyalkanoate synthase gene is not disrupted and by the substrate specificity of the recombinant polyhydroxyalkanoate synthase. When *Pseudomonas* species PC12 strain, which is an isogenic strain line of *Pseudomonas* species YN21 strain and in which the polyhydroxyalkanoate synthase gene is disrupted, is transformed by the polyhydroxyalkanoate synthase gene (phaC1 or phaC2) derived from *Pseudomonas* species YN21 strain, polyhydroxyalkanoate can be produced, in which polymer molecules contain at least one kind of polymer unit which is selected from the group consisting of polymer units with chemical formula from [1] to [16] shown below.

[Formula 1]

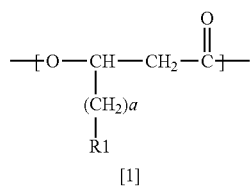

[1]

wherein the combination of R1 and a is at least one selected from the group consisting of polymer units described below:
(1) a polymer unit in which R1 is a hydrogen atom (H) and a is any one of integers from 1 to 10; (2) a polymer unit in which R1 is a halogen element and a is any one of integers from 1 to 10; (3) a polymer unit in which R1 is Formula 2

[Formula 2]

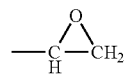

and a is any one of integers from 1 to 8.

[Formula 3]

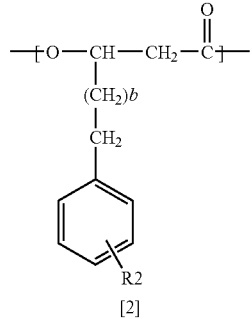

[2]

wherein R2 is a substitution group to the aromatic ring, and represents any one selected from the group consisting of hydrogen atom (H), halogen atom, CN group, $NO_2$ group, COOR' (R': any one of H, Na, and K) group, $CH_3$ group, $C_2H_5$ group, $C_3H_7$ group, $CH=CH_2$ group, $CF_3$ group, $C_2F_5$ group and $C_3F_7$ group, and b represents any one of integers from 0 to 7.

[Formula 4]

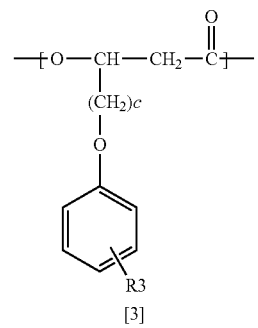

[3]

wherein R3 is a substitution group to the aromatic ring, and represents any one selected from the group consisting of hydrogen atom (H), halogen atom, CN group, $NO_2$ group, $CH_3$ group, $C_2H_5$ group, $C_3H_7$ group, $SCH_3$ group, $CF_3$ group, $C_2F_5$ group and $C_3F_7$ group, and b represents any one of integers from 0 to 7.

[Formula 5]

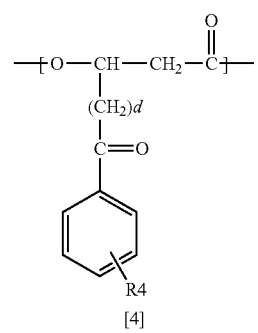

[4]

wherein R4 is a substitution group to the aromatic ring, and represents any one selected from the group consisting of hydrogen atom (H), halogen atom, CN group, $NO_2$ group, $CH_3$ group, $C_2H_5$ group, $C_3H_7$ group, $CF_3$ group, $C_2F_5$ group and $C_3F_7$ group, and d represents any one of integers from 0 to 7.

[Formula 6]

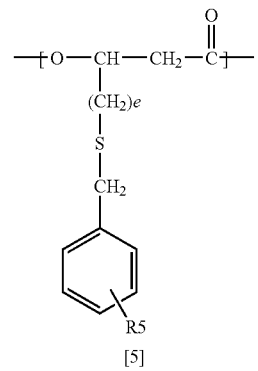

[5]

wherein R5 is a substitution group to the aromatic ring, and represents any one selected from the group consisting of hydrogen atom (H), halogen atom, CN group, $NO_2$ group, COOR' (R': any one of H, Na, K, CH$_3$ and C$_2$H$_5$) group, SO$_2$R" (R": any one of OH, ONa, OK, halogen atom, OCH$_3$ and OC$_2$H$_5$) group, CH$_3$ group, C$_2$H$_5$ group, C$_3$H$_7$ group, CH(CH$_3$)$_2$ group and C(CH$_3$)$_3$ group, and e represents any one of integers from 1 to 8.

[Formula 7]

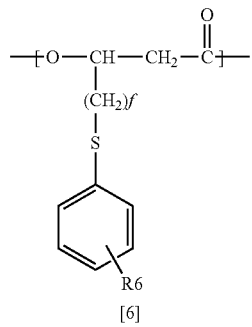

[6]

wherein R6 is a substitution group to the aromatic ring, and represents any one selected from the group consisting of hydrogen atom (H), halogen atom, CN group, NO$_2$ group, COOR' (R': any one of H, Na, K, CH$_3$ and C$_2$H$_5$) group, SO$_2$R" (R": any one of OH, ONa, OK, halogen atom, OCH$_3$ and OC$_2$H$_5$) group, CH$_3$ group, C$_2$H$_5$ group, C$_3$H$_7$ group, CH(CH$_3$)$_2$ group and C(CH$_3$)$_3$ and f represents any one of integers from 1 to 8.

[Formula 8]

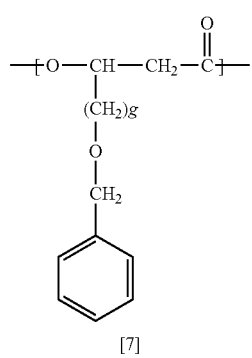

[7]

wherein g represents any one of integers from 1 to 8.

[Formula 9]

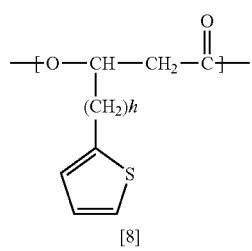

[8]

wherein h represents any one of integers from 1 to 8.

[Formula 10]

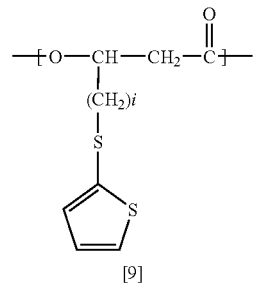

[9]

wherein i represents any one of integers from 1 to 8.

[Formula 11]

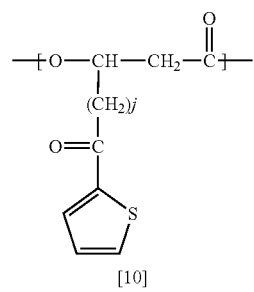

[10]

wherein j represents any one of integers from 1 to 8.

[Formula 12]

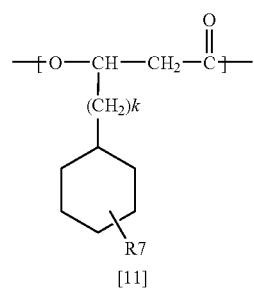

[11]

wherein R7 is a substitution group to cyclohexyl group, and represents any one selected from the group consisting of hydrogen atom (H), halogen atom, CN group, NO$_2$ group, CH$_3$ group, C$_2$H$_5$ group, C$_3$H$_7$ group, CF$_3$ group, C$_2$F$_5$ group and C$_3$F$_7$ group, and k represents any one of integers from 0 to 8.

[Formula 13]

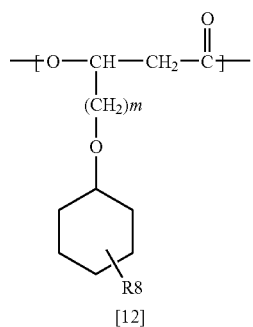

wherein R8 is a substitution group to cyclohexyloxy group, and represents any one selected from the group consisting of hydrogen atom (H), halogen atom, CN group, $NO_2$ group, $CH_3$ group, $C_2H_5$ group, $C_3H_7$ group, $CF_3$ group, $C_2F_5$ group and $C_3F_7$ group, and m represents any one of integers from 1 to 8.

[Formula 14]

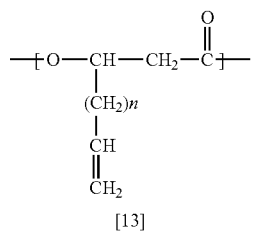

wherein n represents any one of integers from 1 to 8.

[Formula 15]

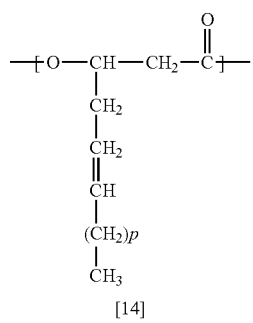

wherein p represents an integer from 3 or 5.

[Formula 16]

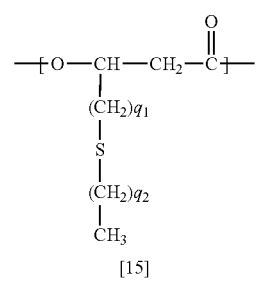

wherein $q_1$ represents any one of integers from 1 to 8 and $q_2$ represents any one of integers from 0 to 8.

[Formula 17]

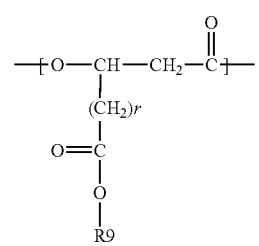

wherein R9 represents hydrogen atom (H), Na atom or K atom, and r represents any one of integers from 1 to 8.

In the case where PHA containing 3-hydroxyalkanoate as monomer units is produced, using the polyhydroxyalkanoate synthase gene disrupted strain transformed by the recombinant polyhydroxyalkanoate synthase gene, an inorganic medium and the like may be used which at least contains corresponding alkanoic acid or alkane as materials for PHA production, and a carbon source for the growth of the disrupted strain.

Medium components derived from natural sources, such as yeast extract, polypeptone, meat extract, casamino acid and the like, may be used as a carbon source for growth. Further, any compound may be used, such as sugars, organic acids which are involved in the TCA cycle (organic acids generated as intermediates in the TCA cycle, or generated after one or two steps of biochemical reactions from the TCA cycle) or salts thereof and the like as long as it can produce acetyl CoA without going through the β-oxidation cycle, and may be chosen depending on the utility as a substrate for the strain to be used.

Among these compounds, examples of sugars include: aldoses such as glycerolaldehyde, erythrol, arabinose, xylose, glucose, galactose, mannose and fructose; alditols such as glycerol, erythritol and xylitol; aldonic acids such as gluconic acid; uronic acids such as glucuronic acid, and galacturonic acid; disaccharides such as maltose, sucrose and lactose, and one or more of the compounds selected from the examples can be used favorably.

Further, examples of organic acid or a salt thereof include pyruvic acid, oxaloacetic acid, citric acid, isocitric acid, ketoglutaric acid, succinic acid, fumaric acid, malic acid, lactic acid, and one or more of the compounds selected from the examples can be used favorably.

Among these compounds, it is preferable to use sugars in particular, and among others it is more preferable to use at least one selected from the group consisting of glucose, fructose and mannose.

As a method to make the polyhydroxyalkanoate synthase gene disrupted strain transformed by the recombinant polyhydroxyalkanoate synthase gene produce and accumulate PHA, it has been observed that sometimes the productivity is improved by inducing expression of polyhydroxyalkanoate synthase, after sufficiently grown, and by culturing after adding a compound which becomes the substrate for the target unit. In particular, the multiple steps method, in which a multiplicity of the aforementioned processes are linked, may be adopted. For example, in this method, the bacteria may be grown in an inorganic medium containing from about 0.05 wt % to 5.0 wt % of D-glucose, and from about 0.01 wt % to 1.0 wt % of alkanoic acid or alkane from the late log phase to the steady state phase, and after collecting the bacteria by centrifugation or the like, further cultured in an inorganic medium containing from about 0.01 wt % to 1.0 wt % of alkanoic acid or alkane for inducing expression of polyhydroxyalkanoate synthase.

Any inorganic medium may be used in the aforementioned culture method as long as it contains components on which bacteria can grow, such as phosphate source (for example, phosphate salts and the like), nitrogen source (for example, ammonium salts, nitrate salts and the like) and the like, and for example, the inorganic medium may include MSB medium, E medium (J. Biol. Chem., 218, 97-106 (1956)), M9 medium and the like.

The composition of M9 medium used in the embodiments of the present invention is as follows:
$Na_2HPO_4$: 6.2 g
$KH_2PO_4$: 3.0 g
NaCl: 0.5 g
$NH_4Cl$: 1.0 g
(for 1 l of medium, pH 7.0)

Further, for better growth and PHA production, it is preferable to add following solution of minor components to the inorganic medium described above.
Minor Components Solution
Nitrilotriacetic acid: 1.5 g
$MgSO_4$: 3.0 g
$MnSO_4$: 0.5 g
NaCl: 1.0 g
$FeSO_4$: 0.1 g
$CaCl_2$: 0.1 g
$CoCl_2$: 0.1 g
$ZnSO_4$: 0.1 g
$CuSO_4$: 0.1 g
$AlK(SO_4)_2$: 0.1 g
$H_3BO_3$: 0.1 g
$Na_2MoO_4$: 0.1 g
$NiCl_2$: 0.1 g
(in 1 l)

Antibiotics such as kanamycin, ampicillin, tetracycline and the like may be added to the medium according to the antibiotics resistant gene integrated into the expression vector so that the expression vector may not be lost during the culturing. When culturing a microbe transformed by the expression vector having the inducible promoter, the inducer may be added to the medium. For example, isopropyl-β-D-thiogalactopyranoside (IPTG), indole acrylic acid (IAA) and the like may be added to the medium.

The culture temperature may be at any temperature as long as the polyhydroxyalkanoate synthase gene disrupted strain, which is transformed by the recombinant polyhydroxyalkanoate synthase gene, can grow well, for example, 15-40° C., preferably 20-35° C., more preferably from about 20° C. to 30° C. is suitable.

As a particular example, desired PHA, which contains very little or no contaminating monomer units that are not the target product, can be extracted by culturing the cells in an inorganic medium and the like containing from 0.05 wt % to about 5.0 wt % of D-glucose and from 0.01 wt % to about 1.0 wt % of alkanoic acid or alkane and by collecting the cells at the time from late log phase to steady state phase. Such PHA is in general composed of only R-bodies and an isotactic polymer. In place of D-glucose, the same amount of organic acids involved in the TCA cycle, east extract, and polypeptone may be given. Also, a combination of these may be used.

To obtain PHA from the culture broth in the present invention, a usual method may be applied. In the case where PHA is excreted into the culture broth, the extraction purification method from the culture medium is used, and in the case where PHA is accumulated in cells, the extraction purification method from cells is used. For example, to recover PHA from cells of cultured microbes, extraction with organic solvent such as chloroform and the like is in common and simplest, but in some cases, apart from chloroform, there are dioxane, tetrahydrofuran, acetonitrile and acetone that may be used. Further, in the environment where organic solvents are difficult to use, the method for collecting PHA may be used by removing the cell body components other than PHA by treatment with: a surface active agent such as SDS and the like; enzyme such as lysozyme and the like; and drug such as EDTA and the like.

Further, the culturing of the microbes of the present invention, production and accumulation in cells of PHA by the microbes of the present invention, as well as the recovery of PHA from cells in the present invention is not limited to the methods described above.

EXAMPLE

Example 1

Since the result of pre-investigation of the drug resistance of the bacterium for producing polyhydroxyalkanoate, *Pseudomonas* species YN21 strain (FERM BP-08569) revealed that it is resistant to ampicillin and chloramphenicol and sensitive to gentamicin, the polyhydroxyalkanoate synthase gene targeting vector was constructed using the gentamicin resistant gene as a marker. The gene disruption vector constructed is a circular plasmid DNA (pPC21(SEQ ID NO: 10)) containing the partial base sequence from the base number 331 to 1215 of the base sequence shown in SEQ ID NO: 1 and the partial base sequence from the base number 1040 to 1667 shown in SEQ ID NO: 2. Following is the description of the procedure. FIG. 1 illustrates the summary of the procedure.

1) Preparation of Genomic DNA

*Pseudomonas* species YN21 strain was cultured in M9 medium containing 0.5% (w/v) of polypeptone at 30° C. for 24 hr. After harvesting the cells from the culture broth, the genomic DNA of YN21 strain was prepared using Wizard Genomic DNA Purification System (manufactured by Promega Inc.)

2) Preparation of DNA Fragment for Insertion

PCR (polymerase chain reaction) was carried out using the genomic DNA of Y21 strain as a template and DNAs with the base sequences shown in YC1-upN (SEQ ID NO: 3) and YC1-2/3C (SEQ ID NO: 4) as primers. The following reaction mixture was prepared.

TABLE 1

| | |
|---|---|
| Template (genomic DNA derived from YN21) | 250 ng |
| Primer YC1-upN (SEQ ID NO: 3) | 250 pmol |
| Primer YC1-2/3C (SEQ ID NO: 4) | 250 pmol |
| 10-fold amplification buffer | 5 μl |
| dNTP | 400 μM |
| Taq polymerase (LA-Taq, manufactured by Takara Shuzo Co., Ltd.) | 2.5 U |
| Sterile distilled water | Appropriate amount |
| Total | 50 μl |

The PCR was carried out for 30 cycles of a series of treatments of: denaturation [98° C. for 20 sec]; annealing [65° C. for 20 sec]; elongation [72° C. for 1 min]. PCR products were confirmed by agarose gel electrophoresis (gel concentration: 1 wt %). As a result, a fragment of about 880 base pairs was amplified. The about 880 base pair PCR amplification product (YC1-up1/3N) was excised out from agarose gel and the DNA fragment was recovered using MinElute Gel Extraction Kit (manufactured by Qiagen Inc.). The about 880 base pair fragment (1) formed a DNA-DNA hybrid with the DNA containing a base sequence represented by SEQ ID NO: 1 under the high ionic concentration [6×SSC (900 mM of sodium chloride, 90 mM sodium citrate)] at the temperature of 65° C., and (2) the hybrid was maintained after washing under the low ionic concentration [0.1×SSC (15 mM of sodium chloride, 1.5 mM sodium citrate)] at the temperature of 65° C. for 30 min, confirming that the DNA hybridized under stringent conditions. Detection of DNA-DNA hybrid was carried out using an AlkPhos Direct Labelling and Detection System (manufactured by Amersham Bioscience Ltd.)

Next, PCR (polymerase chain reaction) was carried out using the genomic DNA of YN21 strain as a template and DNAs having the base sequences shown in YC2-2/3N (SEQ ID NO: 5) and YC2-Ct (SEQ ID NO: 6) as primers. The following reaction mixture was prepared.

TABLE 2

| | |
|---|---|
| Template (genomic DNA derived from YN21) | 250 ng |
| Primer YC2-2/3N (SEQ ID NO: 5) | 250 pmol |
| Primer YC2-Ct (SEQ ID NO: 6) | 250 pmol |
| 10-fold amplification buffer | 5 μl |
| dNTP | 400 μM |
| Taq polymerase (LA-Taq, manufactured by Takara Shuzo Co., Ltd.) | 2.5 U |
| Sterile distilled water | Appropriate amount |
| Total | 50 μl |

The PCR was carried out for 30 cycles of a series of treatments of: denaturation [98° C. for 20 sec]; annealing [65° C. for 20 sec]; elongation [72° C. for 1 min]. PCR products were confirmed by agarose gel electrophoresis (gel concentration: 1 wt %). As a result, a fragment of about 560 base pairs was amplified. The about 560 base pair PCR amplification product (YC2-1/3C) was excised out from agarose gel and the DNA fragment was recovered using MinElute Gel Extraction Kit (manufactured by Qiagen Inc.). The about 560 base pair fragment (1) formed a DNA-DNA hybrid with the DNA containing a base sequence represented by SEQ ID NO: 2 under the high ionic concentration [6×SSC (900 mM of sodium chloride, 90 mM sodium citrate)] at the temperature of 65° C., and (2) the hybrid was maintained after washing under the low ionic concentration [0.1×SSC (15 mM of sodium chloride, 1.5 mM sodium citrate)] at the temperature of 65° C. for 30 min, confirming that the DNA hybridized under stringent conditions. Detection of DNA-DNA hybrid was carried out using an AlkPhos Direct Labelling and Detection System (manufactured by Amersham Bioscience Ltd.)

The primers YC1-2/3C (SEQ ID NO: 4) and YC2-2/3N (SEQ ID NO: 5) contains the recognition sequence of restriction enzyme XbaI already, and by using this, the about 880 base pair PCR product (YC1-up1/3N) and the about 560 base pair PCR product (YC2-1/3C) were linked. First, each of YC1-up1/3N and YC2-1/3C was digested with XbaI. The digested fragments were purified using a spin column for nucleic acid purification (MicroSpin S-400HR, manufactured by Amersham BioScience Ltd.) and the both DNA fragments were ligated using a DNA Ligation Kit ver. 2 (manufactured by Takara Shuzo Co., Ltd.).

Following is the composition of the ligation mixture.

TABLE 3

| | |
|---|---|
| YC1-up1/3N, XbaI digested fragment (50 ng/μl) | 1 μl |
| YC2-1/3C, XbaI digested fragment (50 ng/μl) | 1 μl |
| Concatenation Buffer II (Attached to the kit) | 2 μl |
| Enzyme Solution I (Attached to the kit) | 4 μl |
| Total | 8 μl |

After incubating in a 16° C. incubator for 1 hr, the reaction mixture was desalted and purified by passing through a spin column for nucleic acid purification. PCR was carried out on 1 μl of this purified reaction mixture using DNAs with the base sequences shown in YC1-upN (SEQ ID NO: 3) and YC2-Ct (SEQ ID NO: 6) as primers. Following reaction mixture was prepared.

TABLE 4

| | |
|---|---|
| The aforementioned ligation reaction mixture | 1 μl |
| Primer YC1-upN (SEQ ID NO: 3) | 250 pmol |
| Primer YC2-Ct (SEQ ID NO: 6) | 250 pmol |
| 10-fold amplification buffer | 5 μl |
| dNTP | 400 μM |
| Taq polymerase (LA-Taq, manufactured by Takara Shuzo Co., Ltd.) | 2.5 U |
| Sterile distilled water | Appropriate amount |
| Total | 50 μl |

The PCR was carried out for 30 cycles of a series of treatments of: denaturation [98° C. for 20 sec]; annealing [68° C. for 20 sec]; elongation [72° C. for 1 min]. PCR products were confirmed by agarose gel electrophoresis (gel concentration: 1 wt %). As a result, a fragment of about 1440 base pairs was amplified. The about 1440 base pair PCR amplification product was excised out from agarose gel and the DNA fragment was recovered using MinElute Gel Extraction Kit (manufactured by Qiagen Inc.). The base sequence of the about 1440 base pair PCR product was analyzed using DNAs with the base sequences shown in YC1-upN (SEQ ID NO: 3), YC1-2/3C (SEQ ID NO: 4), YC2-2/3N (SEQ ID NO: 5) and YC2-Ct (SEQ ID NO: 6), and DNA with a complementary sequence to the base sequence shown in YC1-2/3C (SEQ ID NO: 4) and YC2-2/3N (SEQ ID NO: 5) as primers and with a Genetic Analyzer CEQ8000 (manufactured by Beckman Coulter Inc.). The amplified product was confirmed to be corresponding to the linked product of the partial base sequence from the base number 331 to 1215 of the (SEQ ID NO: 1) and the partial base sequence from the base number 1040 to 1667 of the (SEQ ID NO: 2). Each of the primer used for the PCR described above, YC1-upN (SEQ ID NO: 3) and YC2-Ct (SEQ ID NO: 6), contains the recognition sequence of a restriction enzyme XmaI. The about 1440 base pair PCR amplified product was digested with a restriction enzyme XmaI.

3) Preparation of Vector DNA Fragment pEX100T (ATCC No. 87436) was digested with a restriction enzyme XmaI to obtain an about 5.8 kb linear DNA fragment. Dephosphorylation of the 5' termini was carried out using Calf Intestine Alkaline Phosphatase (manufactured by Takara Shuzo Co., Ltd.).

4) Ligation

The XmaI digested fragment (insert DNA) of the about 1440 base pair prepared in 2) described above and the 5.8 kb XmaI digestion product (vector DNA) prepared in 3) described above were ligated using a DNA Ligation Kit Ver. 2 (Takara Shuzo Co., Ltd.) Following is the composition of the ligation reaction mixture.

TABLE 5

| Insert DNA (0.3 pmol/µl) | 1 µl |
| Vector DNA (0.03 pmol/µl) | 4 µl |
| Enzyme Solution I (Attached to the kit) | 5 µl |
| Total | 10 µl |

Figure 2:
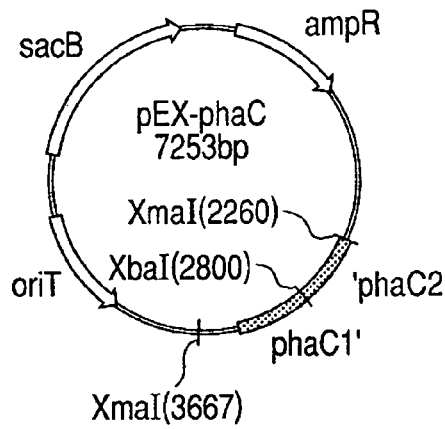
FIG. 2 is the restriction map of plasmid pEX-phaC constructed in Embodiment 1.

After the ligation mixture was incubated in a 16° C. incubator for 1 hr, *Escherichia coli* JM109 competent cells were transformed therewith. Colonies capable of growing on LB agar plate containing 100 µg/ml of ampicillin were selected, and as a result, plasmid pEX-phaC (SEQ ID NO: 7) was obtained. The restriction map of plasmid pEX-phaC is shown in FIG. 2.

5) Insertion of Gentamicin Cassette

After digesting plasmid pEX-phaC prepared in 4) described above with a restriction enzyme XbaI, 5' termini of the fragments were dephosphorylated using Calf Intestine Alkaline Phophatase (manufactured by Takara Shuzo Co., Ltd.). PCR was carried out using pDONR207 (manufactured by Invitrogen Inc.) as a template and DNAs with base sequences shown in gen-f1 (SEQ ID NO: 8) and gen-r1 (SEQ ID NO: 9) as primers. The following reaction mixture was prepared.

TABLE 6

| Template (pDONR207) | 250 ng |
| Primer gen-f1 (SEQ ID NO: 8) | 250 pmol |
| Primer gen-r1 (SEQ ID NO: 9) | 250 pmol |
| 10-fold amplification buffer | 5 µl |
| dNTP | 400 µM |
| Taq polymerase (LA-Taq, manufactured by Takara Shuzo Co., Ltd.) | 2.5 U |
| Sterile distilled water | Appropriate amount |
| Total | 50 µl |

The PCR was carried out for 30 cycles of a series of treatments of: denaturation [98° C. for 20 sec]; annealing [65° C. for 20 sec]; elongation [72° C. for 1 min]. PCR products were confirmed by agarose gel electrophoresis (gel concentration: 1 wt %). As a result, a fragment of about 850 base pair was amplified. The each primer used, gen-f1 (SEQ ID NO: 8) and gen-r1 (SEQ ID NO: 9), already contained a restriction enzyme XbaI recognition site and the about 850 base pair PCR product was digested with restriction enzyme XbaI. The aforementioned XbaI digestion product of the about 850 base pair (insert) and the XbaI digestion product of pEX-phaC (vector) were ligated. The composition of the ligation reaction mixture is shown below.

TABLE 7

| Insert DNA (0.3 pmol/ml) | 1 µl |
| Vector DNA DNA (0.03 pmol/ml) | 4 µl |
| Enzyme Solution I (Attached to the kit) | 5 µl |
| Total | 10 µl |

Figure 3:
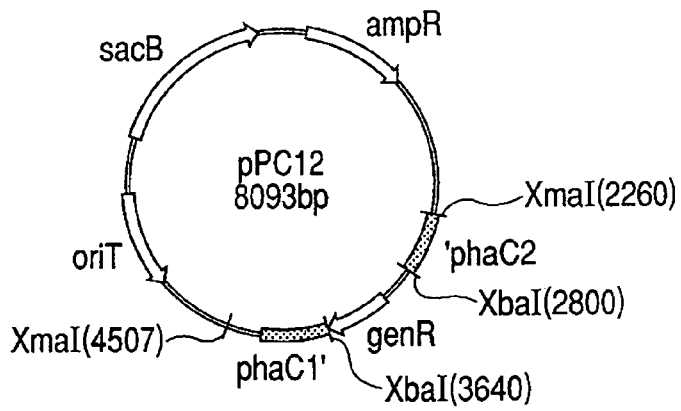
FIG. 3 is the restriction map of plasmid pPC12 (targeting vector for the polyhydroxyalkanoate synthase gene) constructed in Embodiment 1.

After incubating the ligation mixture in a 16° C. incubator for 1 hour, the competent *Escherichia coli* JM109 content cells were transformed therewith. The colonies capable of growing on a LB agar plate containing 15 µg/ml of gentamicin were selected. As a result plasmid pPC12 (SEQ ID NO: 10) was obtained. The restriction map of plasmid pPC12 (polyhydroxyalkanoate synthase gene targeting vector) is shown in FIG. 3.

Example 2

[Acquisition of *Pseudomonas* Species PC12 Strain (FERM BP-08570), the Isogenic Strain Line of the Bacterium for Producing Polyhydroxyalkanoate, in which the Polyhydroxyalkanoate Synthase Gene is Disrupted]

The mobilizing strain *Escherichia coli* S17-1 (ATCC No. 47055) was transformed by the electroporation method with the polyhydroxyalkanoate synthase gene targeting vector (plasmid pPC12, SEQ ID NO: 10) that is constructed in Example 1. The electroporation was carried out in the condition of 2.5 kV, 25 µF, 200Ω using a cell with 0.2 cm gap (Gene Pulser Cuvette 0.2 cm, BioRad Ltd.) and a commercially available electroporation device (Gene Pulser, manufactured by BioRad Inc.). The S17-1 strain transformed with pPC12, obtained as colonies capable of growing on LB agar plate containing 15 µg/ml of gentamicin, was cultured in 5 ml of LB liquid medium containing 100 µg/ml of ampicillin at 30° C. for 12 hr with shaking. Also, *Pseudomonas* species YN21 strain was cultured in 5 ml of LB liquid medium containing 100 µg/ml of ampicillin at 30° C. for 12 hr with shaking. 150 µl of culture broth of *E. coli* S17-1 strain transformed with pPC12 was inoculated to 150 ml of LB liquid medium containing 100 µg/ml ampicillin and cultured at 30° C. with shaking while monitoring absorption at 600 nm (sterilized LB liquid medium was used as a control) occasionally. Similarly, 150 µl of culture broth of YN21 strain was inoculated to 150 ml of LB liquid medium containing 100 µg/ml ampicillin and cultured at 30° C. with shaking while occasionally monitoring absorption at 600 nm (sterilized LB liquid medium was used as a control).

4.5 ml of the culture broth of pPC12 transformed *E. coli* S17-1 strain (absorption at 600 nm was 0.35) and 0.5 ml of the culture broth of YN21 strain (absorption at 600 nm was 0.39) were mixed and filtered using a nitrocellulose filter (pore size 0.45 µm, diameter 25 mm, Millipore made, white surfactant free HATF) to collect the bacteria. The nitrocellulose filter was placed on top of an LB agar plate, keeping the face up, on which the bacteria were collected, covered with a lid to prevent drying and incubated at 30° C. for 90 min. Bacteria on the filter was suspended in 1 ml of LB liquid medium containing 100 µg/ml of ampicillin by pipetting, and an appropriate amount of the suspension was plated on a LB agar plate containing 15 µg/ml of gentamicin and 10 µg/ml of chloramphenicol. Colonies emerged after culturing at 30° C. for 2 days was streaked on a LB agar plate containing 15 µg/ml of gentamicin, 10 μg/ml of chloramphenicol and sucrose 5% (w/v) and cultured at 30° C. for 2 days. A few colonies grown on the LB agar plate containing 15 μg/ml of gentamicin, 10 μg/ml of chloramphenicol and sucrose 5% (w/v) were cultured in M9 medium containing 15 μg/ml of gentamicin, 10 μg/ml of chloramphenicol and 0.5% (w/v) of polypeptone at 30° C. for 24 hr. After harvesting the bacteria from the culture broth, the genomic DNA was prepared using Wizard Genomic DNA Purification System (manufactured by Promega Inc.).

PCR was carried out using the prepared genomic DNA and the control YN21 genomic DNA as templates and DNAs with sequences shown in YC1-upN (SEQ ID NO: 3) and YC2-Ct (SEQ ID NO: 6) as primers. The following reaction mixture was prepared.

TABLE 8

| Template (genomic DNA) | 250 ng |
|---|---|
| Primer YC1-upN (SEQ ID NO: 3) | 250 pmol |
| Primer YC2-Ct (SEQ ID NO: 6) | 250 pmol |
| 10-fold amplification buffer | 5 μl |
| dNTP | 400 μM |
| Taq polymerase (LA-Taq, manufactured by Takara Shuzo Co., Ltd.) | 2.5 U |
| Sterile distilled water | Appropriate amount |
| Total | 50 μl |

The PCR was carried out for 30 cycles of a series of treatments of: denaturation [98° C. for 20 sec]; annealing [64° C. for 20 sec]; elongation [72° C. for 5 min]. PCR products were confirmed by agarose gel electrophoresis (gel concentration: 1 wt %). As a result, when the genomic DNA prepared from the newly obtained colonies was used as a template, about 2.2 kbp DNA fragment was amplified, and when the genomic DNA prepared from control YN21 strain was used as a template, about 4.8 kbp DNA fragment were amplified. This suggests that in the newly obtained clone, the two polyhydroxyalkanoate synthase genes phaC1 and phaC2 are fragmented to about 570 bp and about 540 bp, respectively, and both of them lost the function, and the DNA comprising the gentamicin resistant gene (850 bp) is inserted in between each of the fragments. Thus, PCR amplifies the whole DNA, including the upstream of the phaC1 gene about 220 bp, (220+560+850+540 bp).

Example 3

[Construction of the Expression Vector for the Polyhydroxyalkanoate Synthase Gene (phaC1) Gene]

6) Preparation of Insert DNA

PCR (polymerase chain reaction) was carried out using the genomic DNA of YN21 strain prepared in 1) of Example 1 as a template and DNAs having the base sequence shown in YC1-upN-f1 (SEQ ID NO: 11) and YC1-N-r1 (SEQ ID NO: 12) as primers. Following reaction mixture was prepared.

TABLE 9

| Template (genomic DNA derived from YN21) | 250 ng |
|---|---|
| Primer YC1-upN-f1 (SEQ ID NO: 11) | 250 pmol |
| Primer YC1-N-r1 (SEQ ID NO: 12) | 250 pmol |
| 10-fold amplification buffer | 5 μl |
| dNTP | 400 μM |
| Taq polymerase (LA-Taq, manufactured by Takara Shuzo Co., Ltd.) | 2.5 U |

TABLE 9-continued

| Sterile distilled water | Appropriate amount |
|---|---|
| Total | 50 μl |

The PCR was carried out for 30 cycles of a series of treatments of: denaturation [98° C. for 20 sec]; annealing [65° C. for 20 sec]; elongation [72° C. for 1 min]. PCR products were confirmed by agarose gel electrophoresis (gel concentration: 1 wt %). As a result, a fragment of about 530 base pairs was amplified. The about 530 base pair PCR amplification product was excised out from agarose gel and the DNA fragment was recovered using MinElute Gel Extraction Kit (manufactured by Qiagen Inc.).

PCR was carried out using the genomic DNA of YN21 strain as a template and the about 530 base pair DNA fragment recovered as above and YC1-C-r1 (SEQ ID NO: 13) as primers. Following reaction mixture was prepared.

TABLE 10

| Template (genomic DNA derived from YN21) | 250 ng |
|---|---|
| About 530 bp PCR product | 250 pmol |
| Primer YC1-C-r1 (SEQ ID NO: 13) | 250 pmol |
| 10-fold amplification buffer | 5 μl |
| dNTP | 400 μM |
| Taq polymerase (LA-Taq, manufactured by Takara Shuzo Co., Ltd.) | 2.5 U |
| Sterile distilled water | Appropriate amount |
| Total | 50 μl |

The PCR was carried out for 30 cycles of a series of treatments of: denaturation [98° C. for 20 sec]; annealing [68° C. for 20 sec]; elongation [72° C. for 3 min]. PCR products were confirmed by agarose gel electrophoresis (gel concentration: 1 wt %). As a result, a fragment of about 2.2 kbp was amplified. The about 2.2 kbp PCR amplification product was excised out from agarose gel and the DNA fragment was recovered using MinElute Gel Extraction Kit (Qiagen Inc.).

Each of the primer used, YC1-upN-f1 (SEQ ID NO: 11), YC1-N-r1 (SEQ ID NO: 12) and YC1-C-r1 (SEQ ID NO: 13) contains already the recognition site of restriction enzyme BamHI, XbaI, and SacI, respectively. The about 2.2 kb PCR product was digested with BamHI and SacI.

7) Preparation of Vector DNA Fragment

PCR was carried out using a broad host range vector pBBR122 (MoBiTech, GmbH) as a template and DNAs with the base sequences shown in pBBR/Bam-f1 (SEQ ID NO: 14) and pBBR/Sac-r1 (SEQ ID NO: 15) as primers. Following reaction mixture was prepared.

TABLE 11

| Template (pBBR122) | 250 ng |
|---|---|
| Primer pBBR/Bam-f1 (SEQ ID NO: 14) | 250 pmol |
| Primer pBBR/Sac-r1 (SEQ ID NO: 15) | 250 pmol |
| 10-fold amplification buffer | 5 μl |
| dNTP | 400 μM |
| Taq polymerase (LA-Taq, manufactured by Takara Shuzo Co., Ltd.) | 2.5 U |
| Sterile distilled water | Appropriate amount |
| Total | 50 μl |

The PCR was carried out for 30 cycles of a series of treatments of: denaturation [98° C. for 20 sec]; annealing [65° C. for 20 sec]; elongation [72° C. for 5 min]. PCR products were confirmed by agarose gel electrophoresis (gel concentration: 1 wt %). As a result, a fragment of about 5 kb was amplified. Each of the primer used, pBBR/Bam-f1 (SEQ ID NO: 14) and pBBR/Sac-r1 (SEQ ID NO: 15) contains already the recognition site of restriction enzyme BamHI and SacI, respectively. The about 5 kb PCR product was digested with BamHI and SacI, and then 5' termini of the fragments were dephosphorylated using Calf Intestine Alkaline Phophatase (manufactured by Takara Shuzo Co., Ltd.).

8) Ligation

The about 2.2 kbp Bam HI-SacI digestion product (insert) prepared in 6) above and the about 5 kb BamHI-SacI digest (vector) prepared in 7) above were ligated using DNA Ligation Kit Ver. 2 (manufactured by Takara Shuzo Co., Ltd.). The composition of the ligation reaction mixture is shown below.

TABLE 12

| | |
|---|---|
| Insert DNA (0.3 pmol/μl) | 1 μl |
| Vector DNA (0.03 pmol/μl) | 4 μl |
| Enzyme Solution I (Attached to the kit) | 5 μl |
| Total | 10 μl |

Figure 4:
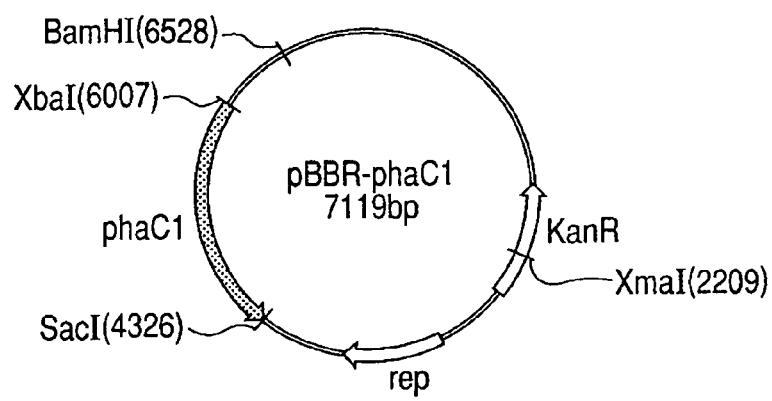
FIG. 4 is the restriction map of plasmid pBBR-phaC1 constructed in Embodiment 3.

After incubating the ligation mixture in a 16° C. incubator for 1 hour, the *Escherichia coli* JM109 competent cell was transformed therewith. The colonies capable of growing on a LB agar plate containing 30 μg/ml of kanamycin were selected. As a result the polyhydroxyalkanoate synthase gene (phaC1) expression vector (plasmid pBBR-phaC1 (SEQ ID NO: 16)) was obtained. The restriction map of plasmid pBBR-phaC1 is shown in FIG. 4.

Example 4

[Construction of the Expression Vector for the Polyhydroxyalkanoate Synthase Gene (phaC2)]

9) Preparation of Insert DNA

PCR (polymerase chain reaction) was carried out using the genomic DNA of YN21 strain prepared in 1) of Example 1 as a template and DNAs having the base sequence shown in YC2-N-f1 (SEQ ID NO: 17) and YC2-C-r1 (SEQ ID NO: 18) as primers. Following reaction mixture was prepared.

TABLE 13

| | |
|---|---|
| Template (genomic DNA derived from YN21) | 250 ng |
| Primer YC2-N-f1 (SEQ ID NO: 17) | 250 pmol |
| Primer YC2-C-r1 (SEQ ID NO: 18) | 250 pmol |
| 10-fold amplification buffer | 5 μl |
| dNTP | 400 μM |
| Taq polymerase (LA-Taq, manufactured by Takara Shuzo Co., Ltd.) | 2.5 U |
| Sterile distilled water | Appropriate amount |
| Total | 50 μl |

The PCR was carried out for 30 cycles of a series of treatments of: denaturation [98° C. for 20 sec]; annealing [63° C. for 20 sec]; elongation [72° C. for 2 min]. PCR products were confirmed by agarose gel electrophoresis (gel concentration: 1 wt %). As a result, a fragment of about 1.7 kbp was amplified. The about 1.7 kbp PCR amplification product was excised out from agarose gel and the DNA fragment was recovered using MinElute Gel Extraction Kit (manufactured by Qiagen Inc.). Each of the primer used, YC2-N-f1 (SEQ ID NO: 17) and YC2-C-r1 (SEQ ID NO: 18) contains already the recognition site of restriction enzymes XbaI and SacI, respectively. The about 1.7 kb PCR product was digested with XbaI and SacI.

10) Preparation of Vector DNA Fragment

After digesting the polyhydroxyalkanoate synthase gene (phaC1) expression vector (plasmid pBBR-phaC1(SEQ ID NO: 16)) prepared in Example 3 with restriction enzymes XbaI and SacI, 5' termini of the fragments were dephosphorylated using Calf Intestine Alkaline Phosphatase (manufactured by Takara Shuzo Co., Ltd.). The digestion products were fractionated by agarose gel electrophoresis (gel concentration: 1%), and the about 5.4 kbp DNA fragment was excised out from agarose gel and recovered using MinElute Gel Extraction Kit (manufactured by Qiagen Inc.).

11) Ligation

The about 1.7 kbp XbaI-SacI digestion product (insert) prepared in 9) above and the about 5.4 kb XbaI-SacI digestion (vector) prepared in 10) above were ligated using DNA Ligation Kit Ver. 2 (manufactured by Takara Shuzo Co., Ltd.). The composition of the ligation reaction mixture is shown below.

TABLE 14

| | |
|---|---|
| Insert DNA (0.3 pmol/μl) | 1 μl |
| Vector DNA (0.03 pmol/μl) | 4 μl |
| Enzyme Solution I (Attached to the kit) | 5 μl |
| Total | 10 μl |

After incubating the ligation mixture in a 16° C. incubator for 1 hour, the *Escherichia coli* JM109 competent cell was transformed therewith. The colonies capable of growing on a LB agar plate containing 30 μg/ml of kanamycin were selected. As a result the polyhydroxyalkanoate synthase gene (phaC2) expression vector (plasmid pBBR-phaC2 (SEQ ID NO: 19)) was obtained. The restriction map of plasmid pBBR-phaC2 is shown in FIG. 5.

Example 5

Using the polyhydroxyalkanoate synthase gene expression vectors pBBR-phaC1 and pBBR-phaC2 constructed in Example 3 and 4, *Pseudomonas* species PC12 strain obtained in Example 2 was transformed by the electroporation method. The electroporation was carried out in the condition of 1.5 kV, 25 μF, 800Ω using a cell with 0.2 cm gap (Gene Pulser Cuvette 0.2 cm, manufactured by BioRad Ltd.) and a commercially available electroporation device (Gene Pulser, manufactured by BioRad Inc.). Transformants (PC12/pBBR-phaC1 and PC12/pBBR-phaC2) capable of growing on a LB agar plate containing 30 μg/ml kanamycin were selected. PC12/pBBR-phaC1 and PC12/pBBR-phaC2 or as a control, PC12 strain, were inoculated to 200 ml of M9 medium containing 0.5% (w/v) polypeptone and 0.1% (v/v) nonanoic acid and cultured at 30° C. with shaking at a rate of 125 strokes/min. After 45 hr, the bacteria were recovered by centrifugation, washed once with cold methanol and freeze dried. This freeze dried pellet was suspended in 100 mL of chloroform, and PHA was extracted by stirring at 60° C. for 20 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA. The molecular weight of PHA thus obtained was measured by the gel permeation chromatography (GPC; Tosoh-HLC-8020, column: Polymer Laboratory PLgel Mixed-C (5 μm), solvent: chloroform, polystyrene conversion). PHA obtained was subjected to methanolysis by the normal procedure and then analyzed with a gas chromatography-mass spectroscopy analysis device (GC-MS, Shimadzu QP-5050, EI method) to identify the methyl ester of PHA monomer unit. These results are shown in Table 15.

TABLE 15

|  | Strain | |
| --- | --- | --- |
|  | PC12/pBBR-phaC1 | PC12/pBBR-phaC2 |
| Cell dry weight | 913 [mg/L] | 771 [mg/L] |
| Polymer dry weight | 429 [mg/L] | 231 [mg/L] |
| Polymer dry weight/Cell dry weight | 47% | 30% |
| Number average molecular weight | 29,000 | 52,000 |
| Weight average molecular weight |  |  |
| Monomer unit composition (area ratio) |  |  |
| 3-hydroxybutyric acid | 2.7% | 28.0% |
| 3-hydroxyvaleric acid | 1.3% | 3.5% |
| 3-hydroxyhexanoic acid | 0% | 0% |
| 3-hydroxyheptanoic acid | 18.0% | 18.5% |
| 3-hydroxyoctanoic acid | 0% | 0% |
| 3-hydroxynonanoic acid | 78% | 50.0% |
| 3-hydroxydecanoic acid | 0% | 0% |

In the control PC12 strain, only a trace amount of poly(3-hydroxybutiric acid) was detected. The result of Table 15 clearly indicates that the isogenic strain line of the bacterium for producing polyhydroxyalkanoate of the present invention, in which the polyhydroxyalkanoate synthase gene is disrupted, is useful as a host that is fully equipped with the substrate supply system enzymes for polyhydroxyalkanoate synthase. It is also useful for synthesizing PHA with variety of composition by the different substrate specificity of the recombinant polyhydroxyalkanoate synthase and carrying out evolutionary engineering modifications, because the substrate specificity of PhaC1 and PhaC2 appear to be different.

Example 6

Unusual PHA was Produced Using the Transformant PC12/pBBR-phaC1 obtained in Example 5.

PC12/pBBR-phaC1 and, as controls, PC12 strain and YN21 strain were inoculated separately in 200 ml of M9 medium containing 0.5% (w/v) of polypeptone and 12 mM phenylvaleric acid and cultured at 30° C. with shaking at a rate of 125 strokes/min. After 45 hr, the bacteria were recovered by centrifugation, washed once with cold methanol and freeze dried. This freeze dried pellet was suspended in 100 mL of chloroform, and PHA was extracted by stirring at 60° C. for 20 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA. The molecular weight of PHA thus obtained was measured by the gel permeation chromatography (GPC; Tosoh-HLC-8020, column: Polymer Laboratory PLgel Mixed-C (5 μm), solvent: chloroform, polystyrene conversion).

PHA obtained was subjected to methanolysis by the normal procedure and then analyzed with a gas chromatography-mass spectroscopy analysis device (GC-MS, Shimadzu QP-5050, EI method) to identify the methyl ester of PHA monomer unit. These results are shown in Table 16.

TABLE 16

|  | Strain | | |
| --- | --- | --- | --- |
|  | PC12/pBBR-phaC1 | PC12 | YN21 (Control) |
| Cell dry weight | 1.96 [g/L] | 1.72 [g/L] | 1.83 [g/L] |
| Polymer dry weight | 1.22 [g/L] | 0.02 [g/L] | 0.91 [g/L] |
| Polymer dry weight/Cell dry weight | 62% | 1% | 50% |
| Monomer unit composition (area ratio) |  |  |  |
| 3-hydroxybutyric acid | 1.2% | 100% | 1.1% |
| 3-hydroxy-5-phenylvaleric acid | 81.5% | 0% | 72.7% |
| 3-hydroxy-7-phenylheptanoic acid | 17.3% | 0% | 26.2% |

The result of Table 16 clearly indicates that the isogenic strain line of the bacterium for producing polyhydroxyalkanoate of the present invention, in which the polyhydroxyalkanoate synthase gene is disrupted, is useful as a host that is fully equipped with the substrate supply system enzymes for polyhydroxyalkanoate synthase, and by expressing PhaC1 (PC12/pBBR-phaC1), PHA can be synthesized again. In this case, the amount of PHA produced by PC12/pBBR-phaC1 strain was found to be increased more than that by YN21 strain. This was believed to be due to the increased amount of PhaC1 expression according to the increased copy number of the vector plasmid than the amount of polyhydroxyalkanoate synthase expression in YN21 strain.

Example 7

[Evolutionary Engineering Modification of Polyhydroxyalkanoate Synthase]

By carrying out Error-prone PCR using the polyhydroxyalkanoate synthase gene (phaC2) expression vector, plasmid pBBR-phaC2 (SEQ ID NO: 19) constructed in Example 4, as a template, a library of polyhydroxyalkanoate synthase gene in which random mutations were introduced (phaC2M) was produced. Mutations were introduced using GeneMorph PCR Mutagenesis Kit (manufactured by Stratagene Inc.).

12) Error-Prone PCR

PCR was carried out using a plasmid as a template and DNAs with the base sequences shown in YC2-N-f1 (SEQ ID NO: 17) and YC2-C-r1 (SEQ ID NO: 18) as primers. Following reaction mixture was prepared.

TABLE 17

| Template | 10 ng |
| --- | --- |
| Primer YC2-N-f1 (SEQ ID NO: 17) | 15 pmol |
| Primer YC2-C-r1 (SEQ ID NO: 18) | 15 pmol |
| 10-fold amplification buffer | 5 μl |
| DMSO | 5 (v/v)% |
| dNTP | 200 μM |
| Mutazyme (manufactured by Stratagene Inc.) | 2.5 U |
| Sterile distilled water | Appropriate amount |
| Total | 50 μl |

The PCR was carried out for 30 cycles of a series of treatments of: denaturation [96° C. for 30 sec]; annealing [60° C. for 30 sec]; elongation [72° C. for 3 min]. PCR products were confirmed by agarose gel electrophoresis (gel concentration: 1%). As a result, a fragment of about 1.7 kbp was amplified. From the amplification ratio, the mutation ratio was estimated to be 4.5 mutations per kb, based on a calculation according to the manual included in the GeneMorph PCR Mutagenesis Kit (manufactured by Stratagene Inc.). The about 1.7 kbp PCR amplification product was excised out from agarose gel and the DNA fragment was recovered using MinElute Gel Extraction Kit (manufactured by Qiagen Inc.). The primes used, YC2-N-f1 (SEQ ID NO: 17) and YC2-C-r1 (SEQ ID NO: 18) contained already the recognition sites of XbaI and SacI, respectively. The about 1.7 kb PCR product was digested with restriction enzymes XbaI and SacI.

13) Production of phaC2M Expression Vector

The about 1.7 kbp PCR product that was produced in 12) described above and digested with restriction enzymes Xba I and SacI and the vector DNA fragment that was produced in 10) of Example 4 were ligated to prepare the expression vector for mutagenized phaC2 library (pBBR-phaC2M).

14) Acquisition of a PHA Producer Strain with Improved Productivity

*Pseudomonas* species PC12 strain was transformed using the mutagenized phaC2 library expression vector (pBBR-phaC2M) by the electroporation method. The electroporation was carried out in the condition of 1.5 kV, 25 μF, 800Ω using a cell with 0.2 cm gap (Gene Pulser Cuvette 0.2 cm, manufactured by BioRad Ltd.) and a commercially available electroporation device (Gene Pulser, manufactured by BioRad Inc.). The transformants were inoculated to 200 ml of M9 medium containing 30 μg/ml of kanamycin, 0.5% (w/v) of polypeptone, 12 mM 5-phenylvaleric acid and cultured at 30° C. with shaking at a rate of 125 strokes/min. After 45 hr, the 15 ml of the culture broth was collected and intracellular PHA granules were stained with Nile red. The composition of staining solution is shown below.

TABLE 18

| Culture broth | 15 mL |
| 50 mg/mL Nile Red DMSO solution | 400 μl |
| Ethanol | 1 mL |
| Sterile distilled water | 3.6 mL |
| Total | 20 mL |

After keeping the staining solution on ice for 2 hours, cell sorting was carried out using a cell sorter (Epics Altra, Beckman Coulter Inc.) based on fluorescent intensity of Nile red. A group of cells with strong fluorescence of Nile red suggesting the high accumulation of intracellular PHA (upper about 0.005%) was recovered.

The recovered cell group was inoculated to 200 ml of M9 medium containing 30 μg/ml of kanamycin, 0.5% (w/v) of polypeptone and 12 mM 5-phenylvaleric acid and cultured at 30° C. with shaking at a rate of 125 strokes/min. After 45 hr, bacteria were recovered, and plasmid was extracted by the standard method.

The extracted plasmid was used as a template in the step 12) described above, and the steps from 12) to 14) described above were repeated for 5 rounds.

The cell group recovered in the last round was plated on a M9 agar plate containing 30 μg/ml of kanamycin, 0.5% (w/v) of polypeptone, 12 mM 5-phenylvaleric acid and 50 μg/ml Nile red, and incubated at 30° C. until single colonies were formed. A colony (PC12/pBBR-phaC2M01 strain) showing the most intense red fluorescent under ultra-violet irradiation was isolated.

From the transformant, PC12/pBBR-phaC2M01 strain, plasmid pBBR-phaC2M01 was extracted by the standard method. The plasmid thus obtained was digested with restriction enzymes, XbaI and SacI, and the about 1.7 kb DNA fragment (phaC2M01) was recovered.

The about 1.7 kb DNA fragment (phaC2M01) (1) formed a DNA-DNA hybrid with the DNA comprising the base sequence shown in SEQ ID NO: 2 by hybridizing under a high ionic concentration [6×SSC (900 mM of sodium chloride, 90 mM sodium citrate)] and at the temperature of 65° C., and (2) the hybrid was maintained after washing under a low ionic concentration [0.1×SSC (15 mM of sodium chloride, 1.5 mM of sodium citrate)] and at the temperature of 65° C. for 30 min, confirming that the DNA was hybridized under stringent conditions. Detection of DNA-DNA hybrid was carried out using an AlkPhos Direct Labelling and Detection System (manufactured by Amersham Bioscience Ltd.).

Example 8

Unusual PHA was Produced Using the Transformant PC12/pBBR-phaC2M01 Strain Obtained in Example 7.

PC12/pBBR-phaC2M01 strain and, as controls, PC12/pBBR-phaC2 strain and YN21 strain were inoculated separately in 200 ml of M9 medium containing 0.5% (w/v) of polypeptone and 12 mM phenylvaleric acid and cultured at 30° C. with shaking at a rate of 125 strokes/min. After 45 hr, the bacteria were recovered by centrifugation, washed once with cold methanol and freeze dried. This freeze dried pellet was suspended in 100 mL of chloroform, and PHA was extracted by stirring at 60° C. for 20 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA. The molecular weight of PHA thus obtained was measured by the gel permeation chromatography (GPC; Tosoh-HLC-8020, column: Polymer Laboratory PLgel Mixed-C (5 μm), solvent: chloroform, polystyrene conversion).

The PHA obtained was subjected to methanolysis by the normal procedure and then analyzed with a gas chromatography-mass spectroscopy analysis device (GC-MS, Shimadzu QP-5050, EI method) to identify the methyl ester of PHA monomer unit. These results are shown in Table 19.

TABLE 19

| | Strain | | |
|---|---|---|---|
| | PC12/ pBBR-phaC2M01 | PC12/ pBBR-phaC2 | YN21 (Control) |
| Cell dry weight | 2.12 [g/L] | 1.96 [g/L] | 1.83 [g/L] |
| Polymer dry weight | 1.55 [g/L] | 1.22 [g/L] | 0.91 [g/L] |
| Polymer dry weight/ Cell dry weight | 73% | 62% | 50% |
| Monomer unit composition (area ratio) | | | |
| 3-hydroxybutyric acid | 1.1% | 1.2% | 1.1% |
| 3-hydroxy-5-phenylvaleric acid | 83.4% | 81.5% | 72.7% |
| 3-hydroxy-7-phenylheptanoic acid | 15.5% | 17.3% | 26.2% |

The result of Table 19 clearly indicates that the isogenic strain line of the bacterium for producing polyhydroxyalkanoate of the present invention, in which the polyhydroxyalkanoate synthase gene is disrupted, is useful as a host that is fully equipped with the substrate supply system enzymes for polyhydroxyalkanoate synthase, and by expressing mutagenized PhaC2M01 (PC12/pBBR-phaC2M01 strain), PHA can be synthesized again. In this case, the amount of PHA produced by PC12/pBBR-phaC2M01 strain is increased more than that by YN21 strain or PC12/pBBR-phaC2 strain. This is believed to be due to the improved substrate affinity of polyhydroxyalkanoate synthase, catalytic reaction rate, or the stability of the enzyme in cytoplasm that was caused by the evolutionary engineering modification by repeating the random mutagenesis and the screening operations.

Example 9

PHA Production using PC12/pBBR-phaC2M01 Strain

Each of the media was prepared by adding an alkanoic acid shown in the next Table 20 to 50 ml of M9 medium containing 0.5% (w/v) of polypeptone and 0.5% (w/v) of glucose.

TABLE 20

| Medium identification number | Alkanoic acid added to the medium |
| --- | --- |
| S1 | 6 mM 7,8-epoxyoctanoic acid |
| S2 | 6 mM 4-phenoxy-n-butyric acid |
| S3 | 6 mM 5-(4-fluorobenzoyl)valeric acid |
| S4 | 6 mM 5-{[(4-fluorophenyl)methyl]sulfanyl}valeric acid |
| S5 | 6 mM 4-(phenylsulfanyl)butyric acid |
| S6 | 6 mM 5-phenylmethyloxyvaleric acid |
| S7 | 6 mM 5-(2-thienyl)valeric acid |
| S8 | 6 mM 5-(2-thienylsulfanyl)valeric acid |
| S9 | 6 mM 5-(2-thienoyl)valeric acid |
| S10 | 6 mM 4-cyclohexylbutyric acid |
| S11 | 6 mM 4-cyclohexyloxybutyric acid |
| S12 | 6 mM 10-undecenoic acid |
| S13 | 6 mM dodec-5-enoic acid |
| S14 | 6 mM 5-(methylthio)valeric acid |

PC12/pBBR-phaC2M01 strain or control YN21 strain was inoculated and cultured at 30° C. with shaking at a rate of 125 strokes/min for 96 hr. Each batch of the bacteria was recovered by centrifugation, washed once with cold methanol and freeze dried. This freeze dried pellet was suspended in 100 mL of chloroform, and PHA was extracted by stirring at 60° C. for 20 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA.

Monomer unit ratio of PHA thus obtained was measured by 1H-NMR (FT-NMR:BrunkerDP×400; resonance frequency: 400 MHz; nuclei: 1H; solvent: $CDCl_3$; reference: TMS/$CDCl_3$ in capillary; Measuring Temperature: room temperature) Result of polymer dry weight (PDW) and monomer unit ratio is shown in Table 21.

TABLE 21

| Medium identification number | PC12/pBBR-phaC2M01 strain | | YN21 strain | |
| --- | --- | --- | --- | --- |
| | PDW (g/L) | Monomer unit ratio (mol %) | PDW (g/L) | Monomer unit ratio (mol %) |
| S1 | 1.46 | 3-hydroxy-7,8-epoxyoctanoic acid 84% | 1.08 | 3-hydroxy-7,8-epoxyoctanoic acid 72% |
| S2 | 1.42 | 3-hydroxy-4-phenoxy-n-butyric acid 74% | 1.05 | 3-hydroxy-4-phenoxy-n-butyric acid 61% |
| S3 | 1.17 | 3-hydroxy-5-(4-fluorobenzoyl)valeric acid 65% | 0.87 | 3-hydroxy-5-(4-fluorobenzoyl)valeric acid 55% |
| S4 | 1.20 | 3-hydroxy-5-{[(4-fluorophenyl)methyl]sulfanyl} valeric acid 74% | 0.89 | 3-hydroxy-5-{[(4-fluorophenyl)methyl]sulfanyl} valeric acid 64% |
| S5 | 1.28 | 3-hydroxy-4-(phenylsulfanyl)butyric acid 75% | 0.95 | 3-hydroxy-4-(phenylsulfanyl)butyric acid 62% |
| S6 | 1.19 | 3-hydroxy-5-phenylmethyloxyvaleric acid 74% | 0.88 | 3-hydroxy-5-phenylmethyloxyvaleric acid 62% |
| S7 | 1.17 | 3-hydroxy-5-(2-thienyl)valeric acid 75% | 0.87 | 3-hydroxy-5-(2-thienyl)valeric acid 62% |
| S8 | 1.34 | 3-hydroxy-5-(2-thienylsulfanyl)valeric acid 74% | 0.99 | 3-hydroxy-5-(2-thienylsulfanyl)valeric acid 62% |

TABLE 21-continued

| Medium | PC12/pBBR-phaC2M01 strain | | YN21 strain | |
|---|---|---|---|---|
| identification number | PDW (g/L) | Monomer unit ratio (mol %) | PDW (g/L) | Monomer unit ratio (mol %) |
| S9 | 1.19 | 3-hydroxy-5-(2-thienoyl)valeric acid 64% | 0.88 | 3-hydroxy-5-(2-thienoyl)valeric acid 52% |
| S10 | 1.32 | 3-hydroxy-4-cyclohexylbutyric acid 74% | 0.98 | 3-hydroxy-4-cyclohexylbutyric acid 62% |
| S11 | 1.46 | 3-hydroxy-4-cyclohexyloxybutyric acid 64% | 1.08 | 3-hydroxy-4-cyclohexyloxybutyric acid 54% |
| S12 | 1.42 | 3-hydroxy-10-undecenoic acid 75% | 1.05 | 3-hydroxy-10-undecenoic acid 64% |
| S13 | 1.11 | 3-hydroxy-dodec-5-enoic acid 74% | 0.82 | 3-hydroxy-dodec-5-enoic acid 53% |
| S14 | 1.23 | 3-hydroxy-5-(methylthio)valeric acid 75% | 0.91 | 3-hydroxy-5-(methylthio)valeric acid 52% |

The result of Table 21 clearly indicates that the new microbial PHA producer, YN21 strain, is useful to produce PHA containing various monomer units. PC12 strain, which is an isogenic strain line of the microbial PHA producer YN21 strain and in which the polyhydroxyalkanoate synthase gene is disrupted, is useful as a host which is fully equipped with the substrate supply system enzymes for polyhydroxyalkanoate synthase, and by expressing mutagenized PhaC2M01 (PC12/pBBR-phaC2M01), PHA can be synthesized again. In this case, the amount of PHA produced by PC12/pBBR-phaC2M01 strain is greater than that by YN21 strain or PC12/pBBR-phaC2 strain. This is believed to be due to the improved substrate affinity of polyhydroxyalkanoate synthase, catalytic reaction rate, or the stability of the enzyme in cytoplasm that was caused by the evolutionary engineering modification by repeating the random mutagenesis and the screening operations. That is, PC12 strain of the present invention is useful as a host for PHA production by introducing PHA synthase, modified or of different species.

Example 10

M9 medium containing 0.5% of polypeptone, 0.1% of phenyl valeric acid, 0.3% of mineral solution and 1.2% of agar powder was sterilized by autoclaving. After cooling to 50° C., the medium was mixed with 0.1% of DMSO solution containing 0.05% of Nile red, distributed to sterilized Petri dish at 15 ml per dish and solidified to prepare agar medium.

The compositions of M9 medium and mineral solution are shown below.

[M9 medium]

$Na_2HPO_4$: 6.2 g, $KH_2PO_4$: 3.0 g, NaCl: 0.5 g, $NH_4Cl$: 1.0 g (in 1 L of medium, pH 7.0)

[Mineral Solution]

Nitrilotriacetic acid: 1.5 g, $MgSO_4$: 3.0 g, $MnSO_4$: 0.5 g, NaCl: 1.0 g, $FeSO_4$: 0.1 g, $CaCl_2$: 0.1 g, $CoCl_2$: 0.1 g, $ZnSO_4$: 0.1 g, $CuSO_4$: 0.1 g, $AlK(SO_4)_2$: 0.1 g, $H_3BO_3$: 0.1 g, $Na_2MoO_4$: 0.1 g, $NiCl_2$: 0.1 g (in 1 L, pH 7.0)

Next, 5 g of soil sample collected in the field was added to 10 ml of sterile distilled water and stirred for 1 min. 0.5 ml of this soil suspension was mixed with 4.5 ml of sterilized water and stirred to prepare 10 fold diluted solution. Similar operations were repeated to prepare 100 fold diluted solution, 1000 fold diluted solution and 10,000 fold diluted solution. The 10-10000 fold diluted sample solutions were inoculated to agar plates prepared earlier at 0.1 ml/plate and spread evenly over the surface of agar. The agar plates were transferred to incubator and cultured at 30° C. for 5 days. Among red colonies, which appeared to have produced PHA, strains with different shape of colony were isolated. More than 10 kinds of such wild type strains were isolated. Next, 50 ml of M9 medium containing 0.5% of polypeptone, 0.5% of glucose, 0.1% of phenyl valeric acid, 0.3% of mineral solution (pH 7.0) was inoculated with a wild type strain of bacteria described above from the stock agar culture and cultured in a 500 ml Sakaguchi flask at 30° C. with shaking at a rate of 125 strokes/min. Also, the medium described above was adjusted to pH 5.0 or pH 8.5, and was inoculated and cultured similarly. After 72 hr, the bacteria were recovered by centrifugation, washed once with cold methanol and freeze dried. This freeze dried pellet was suspended in 10 ml of ethyl acetate, and PHA was extracted by stirring at 35° C. for 15 hr. The extract solution was filtered through a membrane filter with a pore size of 0.45 μm and then concentrated with a rotary evaporator. The concentrated solution was re-precipitated in cold methanol, and only the precipitates were recovered and dried in vacuo to obtain PHA. PHA thus obtained was weighed to measure polymer dry weight (PDW). Monomer unit ratio of PHA was measured by 1H-NMR (FT-NMR: BrukerDP X 400; resonance frequency: 400 MHz; nuclei: 1H; solvent: $CDCl_3$; reference: TMS/CDCl3 in capillary; Measuring Temperature: room temperature). YN21 strain with PHA producing capability was obtained by comparing the polymer dry weight (PDW) and monomer unit ratio in each wild type strain and existing strain.

This application claims priority from Japanese Patent Application No. 2005-023976 filed Jan. 31, 2005, which is hereby incorporated by reference herein.

What is claimed is:

1. *Pseudomonas* sp. PC12 strain (FERM BP-08570).

2. A method of producing polyhydroxyalkanoate comprising culturing the PC12 strain of claim 1 transformed with a recombinant polyhydroxyalkanoate synthase gene and collecting polyhydroxyalkanoate from the culture broth.

* * * * *